United States Patent
Breslin et al.

(10) Patent No.: US 7,235,580 B2
(45) Date of Patent: Jun. 26, 2007

(54) MITOTIC KINESIN INHIBITORS

(75) Inventors: Michael J. Breslin, Drexel Hill, PA (US); Paul J. Coleman, Wallingford, PA (US); Christopher D. Cox, Harleysville, PA (US); George D. Hartman, Lansdale, PA (US); Brenda J. Mariano, Endicott, NY (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/531,495

(22) PCT Filed: Oct. 14, 2003

(86) PCT No.: PCT/US03/32405

§ 371 (c)(1),
(2), (4) Date: Apr. 15, 2005

(87) PCT Pub. No.: WO2004/037171

PCT Pub. Date: May 6, 2004

(65) Prior Publication Data

US 2006/0100191 A1    May 11, 2006

Related U.S. Application Data

(60) Provisional application No. 60/419,570, filed on Oct. 18, 2002, provisional application No. 60/479,712, filed on Jun. 19, 2003.

(51) Int. Cl.
*A61K 31/4025* (2006.01)
*A61K 31/4439* (2006.01)
*C07D 401/02* (2006.01)
*C07D 207/20* (2006.01)
*C07D 413/02* (2006.01)

(52) U.S. Cl. .................. 514/422; 514/423; 514/429; 548/524; 548/538; 548/565; 548/571; 548/577; 546/208

(58) Field of Classification Search ............. 514/422, 514/423, 429; 548/524, 538, 565, 571, 577; 546/208
See application file for complete search history.

(56) References Cited

U.S. PATENT DOCUMENTS

| 3,644,414 A | 2/1972 | Helsey et al. |
| 6,057,342 A | 5/2000 | Fevig et al. |
| 6,440,686 B1 | 8/2002 | Sakowicz |

OTHER PUBLICATIONS

Marcus et al. Journal of Biological Chemistry, 2005, 280, p. 11569.*
M. J. Breslin, et al., Database CALPUS on STN, DN:139:307756 (2003).
M. Bujard, et al., Tetrahedron Letters (40), pp. 8785-8788 (1999).
M.J.S. Carpes, et al., Synlett., No. 7, pp. 1037-1039 (2000).
C. Sonesson, et al., J. Org. Chem. 1996, vol. 61, p. 4756-4763.
N. Iwasawa, et al., J. Org. Chem. 1998, vol. 63, p. 3164-3165.
N. Iwasawa, et al., J. Org. Chem. 1997, vol. 62, p. 1918-1919.
R. Mison, et al., J. Chem. Research(S), 1989, 126-127.
A. Boukhari, et al., J. Cryst. Spect. Res., vol. 19, Iss. 3, 1989, p. 603-621.
N. Moss, et al., J. Med. Chem., vol. 36 (20) pp. 3005-3009 (1993).
M. Fraley, et al., Kinesin spindle protein (KSP) inhibitors. Part 2: The design, synthesis, and characterization of 2,4-diaryl-2,5-dihydropyrrole inhibitors of the mitotic kinesin KSP. Bioorganic & Medicinal Chemistry Letters (2006).
R. Garbaccio, et al., Kinesin spindle protein (KSP) inhibitors. Part 3: Synthesis and evaluation of phenolic 2,4-diaryl-2,5-dihydropyrroles with reduced hERG binding and employment of a phosphate prodrug strategy for aqueous solubility. Bioorganic & Medicinal Chemistry Letters (2006).

* cited by examiner

*Primary Examiner*—Joseph K. McKane
*Assistant Examiner*—Yong Chu
(74) *Attorney, Agent, or Firm*—Nicole M. Beeler; David A. Muthard

(57) ABSTRACT

The present invention relates to dihydropyrrole compounds that are useful for treating cellular proliferative diseases, for treating disorders associated with KSP kinesin activity, and for inhibiting KSP kinesin. The invention is also related to compositions which comprise these compounds, and methods of using them to treat cancer in mammals.

9 Claims, No Drawings

SEQUENCE LISTING

<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: Completely Synthetic Amino Acid Sequence

<400> SEQUENCE: 1
gcaacgatta atatggcgtc gcagccaaat tcgtctgcga ag            42

<210> SEQ ID NO 2
<211> LENGTH: 40
<212> TYPE: DNA
<213> ORGANISM: Artificial Sequence
<220> FEATURE:
<223> OTHER INFORMATION: Completely Synthetic Amino Acid Sequence

<400> SEQUENCE: 2
gatggtggtg atgctgattc acttcaggct tattcaatat            40

MITOTIC KINESIN INHIBITORS

PRIORITY CLAIM

This application is a §371 application of PCT/US03/032405 that was filed on Oct. 14, 2003, which claims priority from the U.S. Provisional Application No. 60/419,570, filed on Oct. 18, 2002, now expired and U.S. Provisional Application No. 60/479,712, filed on Jun. 19, 2003, now expired.

BACKGROUND OF THE INVENTION

This invention relates to 2,2-disubstituted 2,5-dihydropyrrole derivatives that are inhibitors of mitotic kinesins, in particular the mitotic kinesin KSP, and are useful in the treatment of cellular proliferative diseases, for example cancer, hyperplasias, restenosis, cardiac hypertrophy, immune disorders and inflammation.

Among the therapeutic agents used to treat cancer are the taxanes and vinca alkaloids. Taxanes and vinca alkaloids act on microtubules, which are present in a variety of cellular structures. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426], and a fragment of the KSP gene (TRIP5) has been described [Lee, et al., Mol Endocrinol., 9:243-54 (1995); GenBank accession number L40372]. Xenopus KSP homologs (Eg5), as well as Drosophila K-LP61 F/KRP 130 have been reported.

Certain quinazolinones have recently been described as being inhibitors of KSP (PCT Publ. WO 01/30768, May 3, 2001).

Mitotic kinesins are attractive targets for the discovery and development of novel mitotic chemotherapeutics. Accordingly, it is an object of the present invention to provide compounds, methods and compositions useful in the inhibition of KSP, a mitotic kinesin.

SUMMARY OF THE INVENTION

The present invention relates to dihydropyrrole derivatives, that are useful for treating cellular proliferative diseases, for treating disorders associated with KSP kinesin activity, and for inhibiting KSP kinesin. The compounds of the invention may be illustrated by the Formula I:

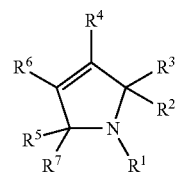

I

DETAILED DESCRIPTION OF THE INVENTION

The compounds of this invention are useful in the inhibition of mitotic kinesins and are illustrated by a compound of Formula I:

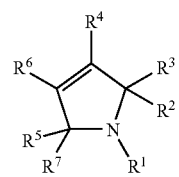

I or a pharmaceutically acceptable salt or stereoisomer thereof, wherein:

a is 0 or 1;
b is 0 or 1;
m is 0, 1, or 2;
n is 0 or 1;
r is 0 or 1;
s is 0 or 1;
$R^1$ is selected from:
1) $(C_1-C_6\text{-alkylene})_n(C=O)C_1-C_{10}$ alkyl,
2) $(C_1-C_6\text{-alkylene})_n(C=O)$aryl,
3) $(C_1-C_6\text{-alkylene})_n(C=O)C_2-C_{10}$ alkenyl,
4) $(C_1-C_6\text{-alkylene})_n(C=O)C_2-C_{10}$ alkynyl,
5) $(C_1-C_6\text{-alkylene})_n(C=O)C_3-C_8$ cycloalkyl,
6) $(C_1-C_6\text{-alkylene})_n(C=O)$heterocyclyl,
7) $(C_1-C_6\text{-alkylene})_n(C=O)NR^cR^{c'}$,
8) $(C_1-C_6\text{-alkylene})_nSO_2NR^cR^{c'}$,
9) $(C_1-C_6\text{-alkylene})_nSO_2C_1-C_{10}$ alkyl,
10) $(C_1-C_6\text{-alkylene})_nSO_2$-aryl,
11) $(C_1-C_6\text{-alkylene})_nSO_2$-heterocyclyl,
12) $(C_1-C_6\text{-alkylene})_nSO_2-C_3-C_8$ cycloalkyl,
13) $(C_1-C_6\text{-alkylene})_nP(=O)R^dR^{d'}$,
14) aryl;
15) heterocyclyl;
16) $C_1-C_{10}$ alkyl;
17) $(C_1-C_6\text{-alkylene})_n(C=O)O—C_1-C_{10}$ alkyl,
18) $(C_1-C_6\text{-alkylene})_n(C=O)O$-aryl,
19) $(C_1-C_6\text{-alkylene})_n(C=O)O—C_2-C_{10}$ alkenyl,
20) $(C_1-C_6\text{-alkylene})_n(C=O)O—C_2-C_{10}$ alkynyl,
21) $(C_1-C_6\text{-alkylene})_n(C=O)O—C_3-C_8$ cycloalkyl,
22) $(C_1-C_6\text{-alkylene})_n(C=O)O$-heterocyclyl, said alkyl, aryl, alkenyl, alkynyl, cycloalkyl, alkylene, heteroaryl and heterocyclyl is optionally substituted with one or more substituents selected from $R^{10}$;

$R^2$ and $R^6$ are independently selected from:
1) aryl,
2) $C_1-C_6$ aralkyl,
3) $C_3-C_8$ cycloalkyl, and
4) heterocyclyl, said aryl, cycloalkyl, aralkyl and heterocyclyl is optionally substituted with one or more substituents selected from $R^{10}$;

$R^3$ is selected from:
1) $C_1-C_{10}$ alkyl-O—$R^g$,
2) $C_2-C_{10}$ alkenyl-O—$R^g$,
3) $C_2-C_{10}$ alkynyl-O—$R^g$,
4) $(C_1-C_6\text{-alkylene})_nC_3-C_8$ cycloalkyl-O—$R^g$,
5) $C_1-C_{10}$ alkyl-$(C=O)_b$—$NR^fR^{f'}$,
6) $C_2-C_{10}$ alkenyl-$(C=O)_bNR^fR^{f'}$,
7) $C_2-C_{10}$ alkynyl-$(C=O)_bNR^fR^{f'}$,
8) $(C_1-C_6\text{-alkylene})_nC_3-C_8$ cycloalkyl-$(C=O)_bNR^fR^{f'}$,
9) $C_1-C_{10}$ alkyl-$S(O)_m$—$R^g$,
10) $C_2-C_{10}$ alkenyl-$S(O)_m$—$R^g$,
11) $C_2-C_{10}$ alkynyl-$S(O)_m$—$R^g$,
12) $(C_1-C_6\text{-alkylene})_nC_3-C_8$ cycloalkyl-$S(O)_m$—$R^g$, said alkyl, alkenyl, alkynyl and cycloalkyl are optionally substituted with one or more substituents selected from $R^{10}$;

$R^4$ is selected from:
1) H,
2) $C_1-C_{10}$ alkyl,
3) aryl,
4) $C_2-C_{10}$ alkenyl,
5) $C_2-C_{10}$ alkynyl,
6) $C_1-C_6$ perfluoroalkyl,
7) $C_1-C_6$ aralkyl,
8) $C_3-C_8$ cycloalkyl, and
9) heterocyclyl, said alkyl, aryl, alkenyl, alkynyl, cycloalkyl, aralkyl and heterocyclyl is optionally substituted with one or more substituents selected from $R^{10}$;

$R^5$ and $R^7$ are independently selected from:
1) H,
2) $C_1-C_{10}$ alkyl,
3) aryl,
4) $C_2-C_{10}$ alkenyl,
5) $C_2-C_{10}$ alkynyl,
6) $C_1-C_6$ perfluoroalkyl,
7) $C_1-C_6$ aralkyl,
8) $C_3-C_8$ cycloalkyl, and
9) heterocyclyl, said alkyl, aryl, alkenyl, alkynyl, cycloalkyl, aralkyl and heterocyclyl is optionally substituted with one or more substituents selected from $R^{10}$; or $R^5$ and $R^7$ are combined to form an oxo or a sulfoxo;

$R^{10}$ is independently selected from:
1) $(C=O)_aO_bC_1-C_{10}$ alkyl,
2) $(C=O)_aO_b$aryl,
3) $C_2-C_{10}$ alkenyl,
4) $C_2-C_{10}$ alkynyl,
5) $(C=O)_aO_b$ heterocyclyl,
6) $CO_2H$,
7) halo,
8) CN,
9) OH,
10) $O_bC_1-C_6$ perfluoroalkyl,
11) $O_a(C=O)_bNR^{12}R^{13}$,
12) $S(O)_mR^a$,
13) $S(O)_2NR^{12}R^{13}$,
14) oxo,
15) CHO,
16) $(N=O)R^{12}R^3$, or
17) $(C=O)_aO_bC_3-C_8$ cycloalkyl, said alkyl, aryl, alkenyl, alkynyl, heterocyclyl, and cycloalkyl optionally substituted with one, two or three substituents selected from $R^{11}$;

$R^{11}$ is selected from:
1) $(C=O)_rO_s(C_1-C_{10})$alkyl,
2) $O_r(C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_rO_s(C_3-C_6)$cycloalkyl,
10) $(C=O)_rO_s(C_0-C_6)$alkylene-aryl,
11) $(C=O)_rO_s(C_0-C_6)$alkylene-heterocyclyl,
12) $(C=O)_rO_s(C_0-C_6)$alkylene-$N(R^b)_2$,
13) $C(O)R^a$,
14) $(C_0-C_6)$alkylene-$CO_2R^a$,
15) C(O)H,
16) $(C_0-C_6)$alkylene-$CO_2H$, and
17) $C(O)N(R^b)_2$,
18) $S(O)_mR^a$, and
19) $S(O)_2N(R^b)_2$;

said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $NO_2$ and $N(R^b)_2$;

$R^{12}$ and $R^{13}$ are independently selected from:

1) H,
2) (C=O)O$_b$C$_1$-C$_{10}$ alkyl,
3) (C=O)O$_b$C$_3$-C$_8$ cycloalkyl,
4) (C=O)O$_b$aryl,
5) (C=O)O$_b$heterocyclyl,
6) C$_1$-C$_{10}$ alkyl,
7) aryl,
8) C$_2$-C$_{10}$ alkenyl,
9) C$_2$-C$_{10}$ alkynyl,
10) heterocyclyl,
11) C$_3$-C$_8$ cycloalkyl,
12) SO$_2$R$^a$, and
13) (C=O)NR$^b{}_2$, said alkyl, cycloalkyl, aryl, heterocylyl, alkenyl, and alkynyl is optionally substituted with one, two or three substituents selected from R$^{11}$, or R$^{12}$ and R$^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^a$ is independently selected from: (C$_1$-C$_6$)alkyl, (C$_3$-C$_6$)cycloalkyl, aryl, or heterocyclyl, optionally substituted with one, two or three substituents selected from R$^{11}$;

R$^b$ is independently selected from: H, (C$_1$-C$_6$)alkyl, aryl, heterocyclyl, (C$_3$-C$_6$)cycloalkyl, (C=O)OC$_1$-C$_6$ alkyl, (C=O)C$_1$-C$_6$ alkyl, (C=O)aryl, (C=O)heterocyclyl, (C=O)NR$^c$R$^{c'}$ or S(O)$_2$R$^a$, optionally substituted with one, two or three substituents selected from R$^{11}$;

R$^c$ and R$^{c'}$ are independently selected from: H, (C$_1$-C$_6$)alkyl, aryl, heterocyclyl and (C$_3$-C$_6$)cycloalkyl, optionally substituted with one, two or three substituents selected from R$^{11}$; or R$^c$ and R$^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^d$ and R$^{d'}$ are independently selected from: (C$_1$-C$_6$)alkyl, (C$_1$-C$_6$)alkoxy and NR$^b{}_2$, or R$^d$ and R$^{d'}$ can be taken together with the phosphorous to which they are attached to form a monocyclic heterocycle with 3-7 members the ring and optionally containing, in addition to the phosphorous, one or two additional heteroatoms selected from NR$^e$, O and S, said monocyclic heterocycle optionally substituted with one, two or three substituents selected from R$^{11}$; and R$^e$ is selected from: H and (C$_1$-C$_6$)alkyl, optionally substituted with one, two or three substituents selected from R$^{11}$;

R$^f$ and R$^{f'}$ are independently selected from: H, (C$_1$-C$_6$)alkyl, aryl, NH$_2$, OH, OR$^a$, —(C$_1$-C$_6$)alkyl-OH, —(C$_1$-C$_6$)alkyl-O—(C$_1$-C$_6$)alkyl, (C=O)OC$_1$-C$_6$ alkyl, (C=O)C$_1$-C$_6$ alkyl, (C=O)aryl, (C=O)heterocyclyl, (C=O)NR$^f$R$^{f'}$, S(O)$_2$R$^a$ and —(C$_1$-C$_6$)alkyl-N(R$^b$)$_2$, wherein the alkyl is optionally substituted with one, two or three substituents selected from R$^{11}$; or R$^f$ and R$^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^g$ is selected from: H, (C$_1$-C$_6$)alkyl, —(C$_1$-C$_6$)alkyl-OH, —(C$_1$-C$_6$)alkyl-O—(C$_1$-C$_6$)alkyl and —(C$_1$-C$_6$)alkyl-N(R$^b$)$_2$.

In an embodiment of the invention the compounds are illustrated by a compound of Formula I:

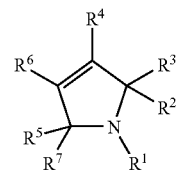

I or a pharmaceutically acceptable salt or stereoisomer thereof, wherein:
a is 0 or 1;
b is 0 or 1;
m is 0, 1, or 2;
n is 0 or 1;
r is 0 or 1;
s is 0 or 1;
R$^1$ is selected from:
1) (C$_1$-C$_6$-alkylene)$_n$(C=O)C$_1$-C$_{10}$ alkyl,
2) (C$_1$-C$_6$-alkylene)$_n$(C=O)aryl,
3) (C$_1$-C$_6$-alkylene)$_n$(C=O)C$_2$-C$_{10}$ alkenyl,
4) (C$_1$-C$_6$-alkylene)$_n$(C=O)C$_2$-C$_{10}$ alkynyl,
5) (C$_1$-C$_6$-alkylene)$_n$(C=O)C$_3$-C$_8$ cycloalkyl,
6) (C$_1$-C$_6$-alkylene)$_n$(C=O)heterocyclyl,
7) (C$_1$-C$_6$-alkylene)$_n$(C=O)NR$^c$R$^{c'}$,
8) (C$_1$-C$_6$-alkylene)$_n$SO$_2$NR$^c$R$^{c'}$,
9) (C$_1$-C$_6$-alkylene)$_n$SO$_2$C$_1$-C$_{10}$ alkyl,
10) (C$_1$-C$_6$-alkylene)$_n$SO$_2$-aryl,
11) (C$_1$-C$_6$-alkylene)$_n$SO$_2$-heterocyclyl,
12) (C$_1$-C$_6$-alkylene)$_n$SO$_2$—C$_3$-C$_8$ cycloalkyl,
13) (C$_1$-C$_6$-alkylene)$_n$P(=O)R$^d$R$^{d'}$,
14) aryl;
15) heterocyclyl;
16) C$_1$-C$_{10}$ alkyl;
17) (C$_1$-C$_6$-alkylene)$_n$(C=O)O—C$_1$-C$_{10}$ alkyl,
18) (C$_1$-C$_6$-alkylene)$_n$(C=O)O-aryl,
19) (C$_1$-C$_6$-alkylene)$_n$(C=O)O—C$_2$-C$_{10}$ alkenyl,
20) (C$_1$-C$_6$-alkylene)$_n$(C=O)O—C$_2$-C$_{10}$ alkynyl,
21) (C$_1$-C$_6$-alkylene)$_n$(C=O)O—C$_3$-C$_8$ cycloalkyl,
22) (C$_1$-C$_6$-alkylene)$_n$(C=O)O-heterocyclyl, said alkyl, aryl, alkenyl, alkynyl, cycloalkyl, alkylene, heteroaryl and heterocyclyl is optionally substituted with one or more substituents selected from R$^{10}$;

R$^2$ and R$^6$ are independently selected from:
1) aryl,
2) C$_1$-C$_6$ aralkyl,
3) C$_3$-C$_8$ cycloalkyl, and
4) heterocyclyl, said aryl, cycloalkyl, aralkyl and heterocyclyl is optionally substituted with one or more substituents selected from $R^{10}$;
$R^3$ is selected from:
1) $C_1$-$C_{10}$ alkyl-O—$R^g$,
2) $C_2$-$C_{10}$ alkenyl-O—$R^g$,
3) $C_2$-$C_{10}$ alkynyl-O—$R^g$,
4) $(C_1$-$C_6$-alkylene$)_n C_3$-$C_8$ cycloalkyl-O—$R^g$,
5) $C_1$-$C_{10}$ alkyl-(C=O)$_b$—NR$^f$R$^{f'}$,
6) $C_2$-$C_{10}$ alkenyl-(C=O)$_b$NR$^f$R$^{f'}$,
7) $C_2$-$C_{10}$ alkynyl-(C=O)$_b$NR$^f$R$^{f'}$,
8) $(C_1$-$C_6$-alkylene$)_n C_3$-$C_8$ cycloalkyl-(C=O)$_b$NR$^f$R$^{f'}$,
9) $C_1$-$C_{10}$ alkyl-S(O)$_m$—$R^g$,
10) $C_2$-$C_{10}$ alkenyl-S(O)$_m$—$R^g$,
11) $C_2$-$C_{10}$ alkynyl-S(O)$_m$—$R^g$,
12) $(C_1$-$C_6$-alkylene$)_n C_3$-$C_8$ cycloalkyl-S(O)$_m$—$R^g$, said alkyl, alkenyl, alkynyl and cycloalkyl are optionally substituted with one or more substituents selected from $R^{10}$;
$R^4$ is selected from:
1) H,
2) $C_1$-$C_{10}$ alkyl,
3) aryl,
4) $C_2$-$C_{10}$ alkenyl,
5) $C_2$-$C_{10}$ alkynyl,
6) $C_1$-$C_6$ perfluoroalkyl,
7) $C_1$-$C_6$ aralkyl,
8) $C_3$-$C_8$ cycloalkyl, and
9) heterocyclyl, said alkyl, aryl, alkenyl, alkynyl, cycloalkyl, aralkyl and heterocyclyl is optionally substituted with one or more substituents selected from $R^{10}$;
$R^5$ and $R^7$ are independently selected from:
1) H,
2) $C_1$-$C_{10}$ alkyl,
3) aryl,
4) $C_2$-$C_{10}$ alkenyl,
5) $C_2$-$C_{10}$ alkynyl,
6) $C_1$-$C_6$ perfluoroalkyl,
7) $C_1$-$C_6$ aralkyl,
8) $C_3$-$C_8$ cycloalkyl, and
9) heterocyclyl, said alkyl, aryl, alkenyl, alkynyl, cycloalkyl, aralkyl and heterocyclyl is optionally substituted with one or more substituents selected from $R^{10}$; or
$R^5$ and $R^7$ are combined to form an oxo or a sulfoxo;
$R^{10}$ is independently selected from:
1) (C=O)$_a$O$_b$C$_1$-C$_{10}$ alkyl,
2) (C=O)$_a$O$_b$aryl,
3) $C_2$-$C_{10}$ alkenyl,
4) $C_2$-$C_{10}$ alkynyl,
5) (C=O)$_a$O$_b$ heterocyclyl,
6) $CO_2H$,
7) halo,
8) CN,
9) OH,
10) O$_b$C$_1$-C$_6$ perfluoroalkyl,
11) O$_a$(C=O)$_b$NR$^{12}$R$^{13}$,
12) S(O)$_m$R$^a$,
13) S(O)$_2$NR$^{12}$R$^{13}$,
14) oxo,
15) CHO,
16) (N=O)R$^{12}$R$^{13}$, or
17) (C=O)$_a$O$_b$C$_3$-$C_8$ cycloalkyl, said alkyl, aryl, alkenyl, alkynyl, heterocyclyl, and cycloalkyl optionally substituted with one, two or three substituents selected from $R^{11}$;

$R^{11}$ is selected from:
1) (C=O)$_r$O$_s$(C$_1$-C$_{10}$)alkyl,
2) O$_r$(C$_1$-C$_3$)perfluoroalkyl,
3) oxo,
4) OH,
5) halo,
6) CN,
7) (C$_2$-C$_{10}$)alkenyl,
8) (C$_2$-C$_{10}$)alkyl,
9) (C=O)$_r$O$_s$(C$_3$-C$_6$)cycloalkyl,
10) (C=O)$_r$O$_s$(C$_0$-C$_6$)alkylene-aryl,
11) (C=O)$_r$O$_s$(C$_0$-C$_6$)alkylene-heterocyclyl,
12) (C=O)$_r$O$_s$(C$_0$-C$_6$)alkylene-N(R$^b$)$_2$,
13) C(O)R$^a$,
14) (C$_0$-C$_6$)alkylene-CO$_2$R$^a$,
15) C(O)H,
16) (C$_0$-C$_6$)alkylene-CO$_2$H, and
17) C(O)N(R$^b$)$_2$,
18) S(O)$_m$R$^a$, and
19) S(O)$_2$N(R$^b$)$_2$;

said alkyl, alkenyl, alkynyl, cycloalkyl, aryl, alkylene and heterocyclyl is optionally substituted with up to three substituents selected from $R^b$, OH, (C$_1$-C$_6$)alkoxy, halogen, CO$_2$H, CN, O(C=O)C$_1$-C$_6$ alkyl, oxo, and N(R$^b$)$_2$;
$R^{12}$ and $R^{13}$ are independently selected from:
1) H,
2) (C=O)O$_b$C$_1$-C$_{10}$ alkyl,
3) (C=O)O$_b$C$_3$-C$_8$ cycloalkyl,
4) (C=O)O$_b$aryl,
5) (C=O)O$_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) SO$_2$R$^a$, and
13) (C=O)NR$^b{}_2$, said alkyl, cycloalkyl, aryl, heterocylyl, alkenyl, and alkynyl is optionally substituted with one, two or three substituents selected from $R^{11}$, or $R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^a$ is independently selected from: (C$_1$-C$_6$)alkyl, (C$_3$-C$_6$) cycloalkyl, aryl, or heterocyclyl, optionally substituted with one, two or three substituents selected from $R^{11}$;

$R^b$ is independently selected from: H, (C$_1$-C$_6$)alkyl, aryl, heterocyclyl, (C$_3$-C$_6$)cycloalkyl, (C=O)OC$_1$-C$_6$ alkyl, (C=O)C$_1$-C$_6$ alkyl, (C=O)aryl, (C=O)heterocyclyl, (C=O)NR$^f$R$^{f'}$ or S(O)$_2$R$^a$, optionally substituted with one, two or three substituents selected from $R^{11}$;

$R^c$ and $R^{c'}$ are independently selected from: H, (C$_1$-C$_6$)alkyl, aryl, heterocyclyl and (C$_3$-C$_6$)cycloalkyl, optionally substituted with one, two or three substituents selected from $R^{11}$; or $R^c$ and $R^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^d$ and $R^{d'}$ are independently selected from: $(C_1$-$C_6)$alkyl, $(C_1$-$C_6)$alkoxy and $NR^b{}_2$, or $R^d$ and $R^{d'}$ can be taken together with the phosphorous to which they are attached to form a monocyclic heterocycle with 3-7 members the ring and optionally containing, in addition to the phosphorous, one or two additional heteroatoms selected from $NR^e$, O and S, said monocyclic heterocycle optionally substituted with one, two or three substituents selected from $R^{11}$; and $R^e$ is selected from: H and $(C_1$-$C_6)$alkyl, optionally substituted with one, two or three substituents selected from $R^{11}$;

$R^f$ and $R^{f'}$ are independently selected from: H, $(C_1$-$C_6)$alkyl, —$(C_1$-$C_6)$alkyl-OH, —$(C_1$-$C_6)$alkyl-O—$(C_1$-$C_6)$alkyl and —$(C_1$-$C_6)$alkyl-N$(R^b)_2$, or $R^f$ and $R^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^g$ is selected from: H, $(C_1$-$C_6)$alkyl, —$(C_1$-$C_6)$alkyl-OH, —$(C_1$-$C_6)$alkyl-O—$(C_1$-$C_6)$alkyl and —$(C_1$-$C_6)$alkyl-N$(R^b)_2$.

Another embodiment of the present invention is illustrated by a compound of Formula II:

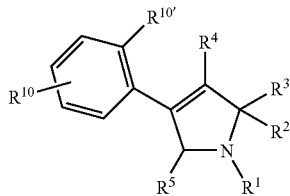

II or a pharmaceutically acceptable salt or stereoisomer thereof, wherein
a is 0 or 1;
b is 0 or 1;
m is 0, 1, or 2;
r is 0 or 1;
s is 0 or 1;
$R^1$ is selected from:
  1) (C=O)$C_1$-$C_{10}$ alkyl,
  2) (C=O)aryl,
  3) (C=O)$C_2$-$C_{10}$ alkenyl,
  4) (C=O)$C_2$-$C_{10}$ alkynyl,
  5) (C=O)$C_3$-$C_8$ cycloalkyl,
  6) (C=O)heterocyclyl,
  7) (C=O)NR$^c$R$^{c'}$,
  8) SO$_2$NR$^c$R$^{c'}$,
  9) SO$_2$C$_1$-C$_{10}$alkyl,
  10) SO$_2$-aryl,
  11) SO$_2$-heterocyclyl,
  12) SO$_2$—C$_3$-C$_8$ cycloalkyl, and
  13) P(=O)R$^d$R$^{d'}$, said alkyl, aryl, alkenyl, alkynyl, cycloalkyl, heteroaryl and heterocyclyl is optionally substituted with one or more substituents selected from $R^{10}$;
$R^2$ is selected from:
  1) aryl,
  2) $C_1$-$C_6$ aralkyl,
  3) $C_3$-$C_8$ cycloalkyl, and
  4) heterocyclyl, said aryl, cycloalkyl, aralkyl and heterocyclyl is optionally substituted with one or more substituents selected from $R^{10}$;
$R^3$ is selected from:
  1) $C_1$-$C_{10}$ alkyl-O—$R^g$,
  2) $C_3$-$C_8$ cycloalkyl-O—$R^g$,
  3) $C_1$-$C_{10}$alkyl-NR$^f$R$^{f'}$,
  4) $C_3$-$C_8$ cycloalkyl-NR$^f$R$^{f'}$, said alkyl and cycloalkyl are optionally substituted with one or more substituents selected from $R^{10}$;
$R^4$ and $R^5$ are independently selected from:
  1) H,
  2) $C_1$-$C_{10}$ alkyl,
  3) aryl,
  4) $C_2$-$C_{10}$ alkenyl,
  5) $C_2$-$C_{10}$ alkynyl,
  6) $C_1$-$C_6$ perfluoroalkyl,
  7) $C_1$-$C_6$ aralkyl,
  8) $C_3$-$C_8$ cycloalkyl, and
  9) heterocyclyl, said alkyl, aryl, alkenyl, alkynyl, cycloalkyl, aralkyl and heterocyclyl is optionally substituted with one or more substituents selected from $R^{10}$;
$R^{10}$ is independently selected from:
  1) (C=O)$_a$O$_b$C$_1$-C$_{10}$ alkyl,
  2) (C=O)$_a$O$_b$aryl,
  3) C$_2$-C$_{10}$ alkenyl,
  4) C$_2$-C$_{10}$ alkynyl,
  5) (C=O)$_a$O$_b$ heterocyclyl,
  6) CO$_2$H,
  7) halo,
  8) CN,
  9) OH,
  10) O$_b$C$_1$-C$_6$ perfluoroalkyl,
  11) O$_a$(C=O)$_b$NR$^{12}$R$^{13}$,
  12) S(O)$_m$R$^a$,
  13) S(O)$_2$NR$^{12}$R$^{13}$,
  14) oxo,
  15) CHO,
  16) (N=O)R$^{12}$R$^{13}$, or
  17) (C=O)$_a$O$_b$C$_3$-C$_8$ cycloalkyl, said alkyl, aryl, alkenyl, alkynyl, heterocyclyl, and cycloalkyl optionally substituted with one, two or three substituents selected from $R^{11}$;
$R^{10'}$ is halogen;
$R^{11}$ is selected from:
  1) (C=O)$_r$O$_s$(C$_1$-C$_{10}$)alkyl,
  2) O$_r$(C$_1$-C$_3$)perfluoroalkyl,
  3) oxo,
  4) OH,
  5) halo,
  6) CN,
  7) (C$_2$-C$_{10}$)alkenyl,
  8) (C$_2$-C$_{10}$)alkynyl,
  9) (C=O)$_r$O$_s$(C$_3$-C$_6$)cycloalkyl,
  10) (C=O)$_r$O$_s$(C$_0$-C$_6$)alkylene-aryl,
  11) (C=O)$_r$O$_s$(C$_0$-C$_6$)alkylene-heterocyclyl,
  12) (C=O)$_r$O$_s$(C$_0$-C$_6$)alkylene-N(R$^b$)$_2$, 13) C(O)$R^a$,
14) ($C_0$-$C_6$)alkylene-$CO_2R^a$,
15) C(O)H,
16) ($C_0$-$C_6$)alkylene-$CO_2H$, and
17) C(O)N($R^b$)$_2$,
18) S(O)$_m$$R^a$, and
19) S(O)$_2$N($R^b$)$_2$;

said alkyl, alkenyl, alkynyl, cycloalkyl, aryl, and heterocyclyl is optionally substituted with up to three substituents selected from $R^b$, OH, ($C_1$-$C_6$)alkoxy, halogen, $CO_2H$, CN, O(C=O)$C_1$-$C_6$ alkyl, oxo, and N($R^b$)$_2$;

$R^{12}$ and $R^{13}$ are independently selected from:
  1) H,
  2) (C=O)O$_b$$C_1$-$C_{10}$ alkyl,
  3) (C=O)O$_b$$C_3$-$C_8$ cycloalkyl,
  4) (C=O)O$_b$aryl,
  5) (C=O)O$_b$heterocyclyl,
  6) $C_1$-$C_{10}$ alkyl,
  7) aryl,
  8) $C_2$-$C_{10}$ alkenyl,
  9) $C_2$-$C_{10}$ alkynyl,
  10) heterocyclyl,
  11) $C_3$-$C_8$ cycloalkyl,
  12) SO$_2R^a$, and
  13) (C=O)N$R^b{}_2$, said alkyl, cycloalkyl, aryl, heterocylyl, alkenyl, and alkynyl is optionally substituted with one, two or three substituents selected from $R^{11}$, or $R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^a$ is independently selected from: ($C_1$-$C_6$)alkyl, ($C_3$-$C_6$) cycloalkyl, aryl, or heterocyclyl, optionally substituted with one, two or three substituents selected from $R^{11}$;

$R^b$ is independently selected from: H, ($C_1$-$C_6$)alkyl, aryl, heterocyclyl, ($C_3$-$C_6$)cycloalkyl, (C=O)O$C_1$-$C_6$ alkyl, (C=O)$C_1$-$C_6$ alkyl, (C=O)aryl, (C=O)heterocyclyl, (C=O)N$R^fR^{f'}$ or S(O)$_2R^a$, optionally substituted with one, two or three substituents selected from $R^{11}$;

$R^c$ and $R^{c'}$ are independently selected from: H, ($C_1$-$C_6$)alkyl, aryl, heterocyclyl and ($C_3$-$C_6$)cycloalkyl, optionally substituted with one, two or three substituents selected from $R^{11}$; or $R^c$ and $R^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^d$ and $R^{d'}$ are independently selected from: ($C_1$-$C_6$)alkyl, ($C_1$-$C_6$)alkoxy and N$R^b{}_2$, or $R^d$ and $R^{d'}$ can be taken together with the phosphorous to which they are attached to form a monocyclic heterocycle with 3-7 members the ring and optionally containing, in addition to the phosphorous, one or two additional heteroatoms selected from N$R^e$, O and S, said monocyclic heterocycle optionally substituted with one, two or three substituents selected from $R^{11}$;

$R^e$ is selected from: H and ($C_1$-$C_6$)alkyl, optionally substituted with one, two or three substituents selected from $R^{11}$;

$R^f$ and $R^{f'}$ are independently selected from: H, ($C_1$-$C_6$)alkyl, —($C_1$-$C_6$)alkyl-OH, —($C_1$-$C_6$)alkyl-O—($C_1$-$C_6$)alkyl and —($C_1$-$C_6$)alkyl-N($R^b$)$_2$, or $R^f$ and $R^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^g$ is selected from: H, ($C_1$-$C_6$)alkyl, —($C_1$-$C_6$)alkyl-OH, —($C_1$-$C_6$)alkyl-O—($C_1$-$C_6$)alkyl and —($C_1$-$C_6$)alkyl-N($R^b$)$_2$.

Another embodiment is the compound of the Formula II described immediately above, or a pharmaceutically acceptable salt or stereoisomer thereof, wherein:

$R^1$ is selected from:
  1) —(C=O)N$R^cR^{c'}$,
  2) —(C=O)$C_1$-$C_{10}$ alkyl,
  3) —SO$_2$N$R^cR^{c'}$, and
  4) —SO$_2C_1$-$C_{10}$ alkyl, said alkyl, is optionally substituted with one, two or three substituents selected from $R^{10}$;

$R^2$ is selected from:
  1) aryl, and
  2) heteroaryl, said aryl and heteroaryl is optionally substituted with one or more substituents selected from $R^{10}$;

$R^3$ is selected from:
  1) $C_1$-$C_{10}$ alkyl-O—$R^g$,
  2) $C_1$-$C_{10}$ alkyl-N$R^fR^{f'}$, said alkyl and cycloalkyl are optionally substituted with one or more substituents selected from $R^{10}$;

$R^4$ and $R^5$ are independently selected from:
  1) H, and
  2) $C_1$-$C_{10}$ alkyl, said alkyl is optionally substituted with one or more substituents selected from $R^{10}$; and $R^{10}$, $R^{10'}$, $R^{11}$, $R^{12}$, $R^{13}$, $R^a$, $R^b$, $R^c$, $R^{c'}$, $R^f$, $R^{f'}$ and $R^g$ are as described immediately above.

In another embodiment of the compounds of Formula II hereinabove, $R^2$ is independently selected from phenyl or pyridyl, optionally substituted with one or two substituents selected from $R^{10}$.

Another embodiment is the compound of the Formula II described immediately above, or a pharmaceutically acceptable salt or stereoisomer thereof, wherein $R^2$ is phenyl, optionally substituted with one or two substituents selected from $R^{10}$.

An embodiment of the present invention is illustrated by a compound of Formula II:

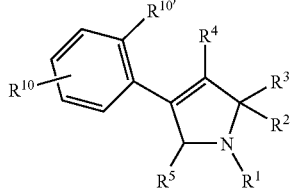

or a pharmaceutically acceptable salt or stereoisomer thereof, wherein
a is 0 or 1;
b is 0 or 1;
m is 0, 1, or 2;
r is 0 or 1;
s is 0 or 1;
$R^1$ is selected from:
  1) (C=O)$C_1$-$C_{10}$ alkyl,
  2) (C=O)aryl,
  3) (C=O)$C_2$-$C_{10}$ alkenyl,
  4) (C=O)$C_2$-$C_{10}$ alkynyl,
  5) (C=O)$C_3$-$C_8$ cycloalkyl,
  6) (C=O)heterocyclyl,
  7) (C=O)NR$^c$R$^{c'}$,
  8) SO$_2$NR$^c$R$^{c'}$,
  9) SO$_2$$C_1$-$C_{10}$ alkyl,
  10) SO$_2$-aryl,
  11) SO$_2$-heterocyclyl,
  12) SO$_2$—$C_3$-$C_8$ cycloalkyl, and
  13) P(=O)R$^d$R$^{d'}$, said alkyl, aryl, alkenyl, alkynyl, cycloalkyl, heteroaryl and heterocyclyl is optionally substituted with one or more substituents selected from $R^{10}$;
$R^2$ is phenyl, optionally substituted with one or more substituents selected from $R^{10}$;
$R^3$ is selected from:
  1) $C_1$-$C_{10}$ alkyl-O—R$^g$,
  2) $C_1$-$C_{10}$ alkyl-NR$^f$R$^{f'}$, said alkyl is optionally substituted with one or more substituents selected from $R^{10}$;
$R^4$ and $R^5$ are independently selected from:
  1) H,
  2) $C_1$-$C_{10}$ alkyl,
  3) aryl,
  4) $C_2$-$C_{10}$ alkenyl,
  5) $C_2$-$C_{10}$ alkynyl,
  6) $C_1$-$C_6$ perfluoroalkyl,
  7) $C_1$-$C_6$ aralkyl,
  8) $C_3$-$C_8$ cycloalkyl, and
  9) heterocyclyl, said alkyl, aryl, alkenyl, alkynyl, cycloalkyl, aralkyl and heterocyclyl is optionally substituted with one or more substituents selected from $R^{10}$;
$R^{10}$ is independently selected from:
  1) (C=O)$_a$O$_b$$C_1$-$C_{10}$ alkyl,
  2) (C=O)$_a$O$_b$aryl,
  3) $C_2$-$C_{10}$ alkenyl,
  4) $C_2$-$C_{10}$ alkynyl,
  5) (C=O)$_a$O$_b$ heterocyclyl,
  6) CO$_2$H,
  7) halo,
  8) CN,
  9) OH,
  10) O$_b$$C_1$-$C_6$ perfluoroalkyl,
  11) O$_a$(C=O)$_b$NR$^{12}$R$^{13}$,
  12) S(O)$_m$R$^a$,
  13) S(O)$_2$NR$^{12}$R$^{13}$,
  14) oxo,
  15) CHO,
  16) N=O)R$^{12}$R$^{13}$, or
  17) (C=O)$_a$O$_b$$C_3$-$C_8$ cycloalkyl, said alkyl, aryl, alkenyl, alkynyl, heterocyclyl, and cycloalkyl optionally substituted with one, two or three substituents selected from $R^{11}$;
$R^{10'}$ is halogen;
$R^{11}$ is selected from:
  1) (C=O)$_r$O$_s$($C_1$-$C_{10}$)alkyl,
  2) O$_r$($C_1$-$C_3$)perfluoroalkyl,
  3) oxo,
  4) OH,
  5) halo,
  6) CN,
  7) ($C_2$-$C_{10}$)alkenyl,
  8) ($C_2$-$C_{10}$)alkynyl,
  9) (C=O)$_r$O$_s$($C_3$-$C_6$)cycloalkyl,
  10) (C=O)$_r$O$_s$($C_0$-$C_6$)alkylene-aryl,
  11) (C=O)$_r$O$_s$($C_0$-$C_6$)alkylene-heterocyclyl,
  12) (C=O)$_r$O$_s$($C_0$-$C_6$)alkylene-N(R$^b$)$_2$,
  13) C(O)R$^a$,
  14) ($C_0$-$C_6$)alkylene-CO$_2$R$^a$,
  15) C(O)H,
  16) ($C_0$-$C_6$)alkylene-CO$_2$H, and
  17) C(O)N(R$^b$)$_2$,
  18) S(O)$_m$R$^a$, and
  19) S(O)$_2$N(R$^b$)$_2$;

said alkyl, alkenyl, alkynyl, cycloalkyl, aryl, and heterocyclyl is optionally substituted with up to three substituents selected from R$^b$, OH, ($C_1$-$C_6$)alkoxy, halogen, CO$_2$H, CN, O(C=O)$C_1$-$C_6$ alkyl, oxo, and N(R$^b$)$_2$;
$R^{12}$ and $R^{13}$ are independently selected from:
  1) H,
  2) (C=O)O$_b$$C_1$-$C_{10}$ alkyl,
  3) (C=O)O$_b$$C_3$-$C_8$ cycloalkyl,
  4) (C=O)O$_b$aryl,
  5) (C=O)O$_b$heterocyclyl,
  6) $C_1$-$C_{10}$ alkyl,
  7) aryl,
  8) $C_2$-$C_{10}$ alkenyl,
  9) $C_2$-$C_{10}$ alkynyl,
  10) heterocyclyl,
  11) $C_3$-$C_8$ cycloalkyl,
  12) SO$_2$R$^a$, and
  13) (C=O)NR$^b$$_2$, said alkyl, cycloalkyl, aryl, heterocylyl, alkenyl, and alkynyl is optionally substituted with one, two or three substituents selected from $R^{11}$, or $R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^a$ is independently selected from: $(C_1-C_6)$alkyl, $(C_3-C_6)$cycloalkyl, aryl, or heterocyclyl, optionally substituted with one, two or three substituents selected from $R^{11}$;

$R^b$ is independently selected from: H, $(C_1-C_6)$alkyl, aryl, heterocyclyl, $(C_3-C_6)$cycloalkyl, (C=O)O$C_1-C_6$ alkyl, (C=O)$C_1-C_6$ alkyl, (C=O)aryl, (C=O)heterocyclyl, (C=O)N$R^cR^{c'}$ or S(O)$_2R^a$, optionally substituted with one, two or three substituents selected from $R^{11}$;

$R^c$ and $R^{c'}$ are independently selected from: H, $(C_1-C_6)$alkyl, aryl, heterocyclyl and $(C_3-C_6)$cycloalkyl, optionally substituted with one, two or three substituents selected from $R^{11}$; or $R^c$ and $R^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^d$ and $R^{d'}$ are independently selected from: $(C_1-C_6)$alkyl, $(C_1-C_6)$alkoxy and N$R^b{}_2$, or $R^d$ and $R^{d'}$ can be taken together with the phosphorous to which they are attached to form a monocyclic heterocycle with 3-7 members the ring and optionally containing, in addition to the phosphorous, one or two additional heteroatoms selected from N$R^e$, O and S, said monocyclic heterocycle optionally substituted with one, two or three substituents selected from $R^{11}$;

$R^e$ is selected from: H and $(C_1-C_6)$alkyl, optionally substituted with one, two or three substituents selected from $R^{11}$;

$R^f$ and $R^{f'}$ are independently selected from: H, $(C_1-C_6)$alkyl, —$(C_1-C_6)$alkyl-OH, —$(C_1-C_6)$alkyl-O—$(C_1-C_6)$alkyl and —$(C_1-C_6)$alkyl-N$(R^b)_2$, or $R^f$ and $R^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^g$ is selected from: H, $(C_1-C_6)$alkyl, —$(C_1-C_6)$alkyl-OH, —$(C_1-C_6)$alkyl-O—$(C_1-C_6)$alkyl and —$(C_1-C_6)$alkyl-N$(R^b)_2$.

Specific examples of the compounds of the instant invention include:

4-(2,5-Difluorophenyl)-2-(hydroxymethyl)-N,N-dimethyl-2-phenyl-2,5-dihydro-1H-pyrrole-1-carboxamide;

4-(2,5-Difluorophenyl)-2-(hydroxymethyl)-N-methyl-N-(1-methylpiperidin-4-yl)-2-phenyl-2,5-dihydro-1H-pyrrole-1-carboxamide;

4-(2,5-Difluorophenyl)-2-(methoxymethyl)-N,N-dimethyl-2-phenyl-2,5-dihydro-1H-pyrrole-1-carboxamide;

4-(2,5-Difluorophenyl)-2-[(2-hydroyethoxy)methyl]-N,N-diethyl-2-phenyl-2,5-dihydro-1H-pyrrole-1-carboxamide;

2-[(2-Aminoethoxy)methyl]-4-(2,5-difluorophenyl)-N,N-dimethyl-2-phenyl-2,5-dihydro-1H-pyrrole-1-carboxamide;

4-(2,5-Difluorophenyl)-2-({[2-(dimethylamino)ethyl]amino}methyl)-N,N-dimethyl-2-phenyl-2,5-hydro-1H-pyrrole-1-carboxamide;

3-{-(2,5-Difluorophenyl)-1-[(dimethylamino)carbonyl]-2-phenyl-2,5-dihydro-1H-pyrrol-2-yl}prop-2-en-1-aminium;

2-(3-Hydroxypropyl)-4-(2,5-difluorophenyl)-N,N-dimethyl-2-phenyl-2,5-dihydro-1H-pyrrole-1-carboxamide;

2-(3-Aminopropyl)-4-(2,5-difluorophenyl)-N,N-dimethyl-2-phenyl-2,5-dihydro-1H-pyrrole-1-carboxamide;

4-(2,5-Difluorophenyl)-2-[3-(dimethylamino)propyl]-N,N-dimethyl-2-phenyl-2,5-hydro-1H-pyrrole-1-carboxamide;

4-(2,5-difluorophenyl)-2-(1-hydroxyethyl)-N,N-dimethyl-2-phenyl-2,5-dihydro-1H-pyrrole-1-carboxamide;

[4-(2,5-difluorophenyl)-2-phenyl-1-(piperidin-1-ylcarbonyl)-2,5-dihydro-1H-pyrrol-2-yl]methanol;

2-({[tert-butyl(dimethyl)silyl]oxy}methyl)-4-(2,5-difluorophenyl)-N-methyl-2-phenyl-N-piperidin-4-yl-2,5-dihydro-1H-pyrrole-1-carboxamide;

4-(2,5-difluorophenyl)-N-[1-(N,N-dimethylglycyl)piperidinyl-4-yl]-2-(hydroxymethyl)-N-methyl-2-phenyl-2,5-dihydro-1H-pyrrole-1-carboxamide;

4-(2,5-fluorophenyl)-2-(hydroxymethyl)-N-methyl-N-[1-(morpholin-4-ylacetyl)piperidin-4-yl]-2-phenyl-2,5-dihydro-1H-pyrrole-1-carboxamide;

4-(2,5-difluorophenyl)-2-(hydroxymethyl)-N-methyl-2-phenyl-N-piperidin-3-yl-2,5-dihydro-1H-pyrrole-1-carboxamide;

N-[1-(2,2-difluoroethyl)piperidin-4-yl]-4-(2,5-difluorophenyl)-2-(hydroxymethyl)-N-methyl-2-phenyl-2,5-dihydro-1H-pyrrole-1-carboxamide;

4-(2,5-difluorophenyl)-N-[1-(2-hydroxyethyl)piperidin-4-yl]-2-(hydroxymethyl)-N-methyl-2-phenyl-2,5-dihydro-1H-pyrrole-1-carboxamide;

(2S)-4-(2,5-difluorophenyl)-N-[1-(2-fluoroethyl)piperidin-4-yl]-2-(hydroxymethyl)-N-methyl-2-phenyl-2,5-dihydro-1H-pyrrole-1-carboxamide;

4-(2,5-difluorophenyl)-2-(hydroxymethyl)-N-methyl-N-{1-[(methylsulfonyl)methyl]piperidin-4-yl}-2-phenyl-2,5-dihydro-1H-pyrrole-1-carboxamide;

4-(2,5-difluorophenyl)-N-{1-[2-fluoro-1-(fluoromethyl)ethyl]piperidin-4-yl}-2-(hydroxymethyl)-N-methyl-2-phenyl-2,5-dihydro-1H-pyrrole-1-carboxamide;

(2S)-N-(1-cyclopropylpiperidin-4-yl)-4-(2,5-difluorophenyl)-2-(hydroxymethyl)-N-methyl-2-phenyl-2,5-dihydro-1H-pyrrole-1-carboxamide;

benzyl {4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetate;

{4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetic acid;

methyl {4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetate;

4-(2,5-difluorophenyl)-2-(methoxymethyl)-N-methyl-N-(1-methylpiperidin-4-yl)-2-phenyl-2,5-dihydro-1H-pyrrole-1-carboxamide;

4-(2,5-difluorophenyl)-2-(3-hydroxypropyl)-N,N-dimethyl-2-phenyl-2,5-dihydro-1H-pyrrole-1-carboxamide;

2-{3-[(2,2-difluoroethyl)amino]propyl}-4-(2,5-difluorophenyl)-N,N-dimethyl-2-phenyl-2,5-dihydro-1H-pyrrole-1-carboxamide;

2-{3-[(2,2-difluoroethyl)(methyl)amino]propyl}-4-(2,5-difluorophenyl)-N,N-dimethyl-2-phenyl-2,5-dihydro-1H-pyrrole-1-carboxamide;

2-(3-aminopropyl)-4-(5-chloro-2-fluorophenyl)-N,N-dimethyl-2-phenyl-2,5-dihydro-1H-pyrrole-1-carboxamide;

2-[3-(acetylamino)propyl]-4-(5-chloro-2-fluorophenyl)-N,N-dimethyl-2-phenyl-2,5-dihydro-1H-pyrrole-1-carboxamide;

4-(5-chloro-2-fluorophenyl)-N,N-dimethyl-2-{3-[(methylsulfonyl)amino]propyl}-2-phenyl-2,5-dihydro-1H-pyrrole-1-carboxamide;

methyl 3-{4-(5-chloro-2-fluorophenyl)-1-[(diethylamino)carbonyl]-2-phenyl-2,5-dihydro-1H-pyrrol-2-yl}propylcarbamate;

2-{3-[(aminocarbonyl)amino]propyl}-4-(5-chloro-2-fluorophenyl)-N,N-dimethyl-2-phenyl-2,5-dihydro-1H-pyrrole-1-carboxamide;

3-{4-(2,5-difluorophenyl)-1-[(dimethylamino)carbonyl]-2-phenyl-2,5-dihydro-1H-pyrrol-2-yl}propanoic acid;

2-(3-anilino-3-oxopropyl)-4-(2,5-difluorophenyl)-N,N-dimethyl-2-phenyl-2,5-dihydro-1H-pyrrole-1-carboxamide;

4-(2,5-difluorophenyl)-2-(3-hydrazino-3-oxopropyl)-N,N-dimethyl-2-phenyl-2,5-dihydro-1H-pyrrole-1-carboxamide;

4-(2,5-difluorophenyl)-2-[3-(hydroxyamino)-3-oxopropyl]-N,N-dimethyl-2-phenyl-2,5-dihydro-1H-pyrrole-1-carboxamide;

2-(2,2-difluoro-3-hydroxypropyl)-4-(2,5-difluorophenyl)-N,N-dimethyl-2-phenyl-2,5-dihydro-1H-pyrrole-1-carboxamide;

2-(3-amino-2,2-difluoropropyl)-4-(2,5-difluorophenyl)-N,N-dimethyl-2-phenyl-2,5-dihydro-1H-pyrrole-1-carboxamide;

4-(2,5-difluorophenyl)-2-[3-(dimethylamino)propyl]-N-methyl-2-phenyl-N-tetrahydro-2H-pyran-4-yl-2,5-dihydro-1H-pyrrole-1-carboxamide;

1-{4-(2,5-difluorophenyl)-2-[3-(dimethylamino)propyl]-2-phenyl-2,5-dihydro-1H-pyrrol-1-yl}-2-methyl-1-oxopropan-2-ol;

3-[(2S)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine; and (2S)-2-(3-amino-4,4-fluorobutyl)-4-(2,5-difluorophenyl)-N,N-dimethyl-2-phenyl-2,5-dihydro-1H-pyrrole-1-carboxamide;

or a pharmaceutically acceptable salt or stereoisomer thereof.

Particular examples of the compounds of the instant invention are:

4-(2,5-Difluorophenyl)-2-(hydroxymethyl)-N-methyl-N-(1-methylpiperidin-4-yl)-2-phenyl-2,5-dihydro-1H-pyrrole-1-carboxamide;

2-[(2-Aminoethoxy)methyl]-4-(2,5-difluorophenyl)-N,N-dimethyl-2-phenyl-2,5-hydro-1H-pyrrole-1-carboxamide;

2-(3-Aminopropyl)-4-(2,5-difluorophenyl)-N,N-dimethyl-2-phenyl-2,5-dihydro-1H-pyrrole-1-carboxamide;

4-(2,5-Difluorophenyl)-2-[3-(dimethylamino)propyl]-N,N-dimethyl-2-phenyl-2,5-dihydro-1H-pyrrole-1-carboxamide;

or a pharmaceutically acceptable salt or stereoisomer thereof.

Further examples of the compounds of the instant invention are:

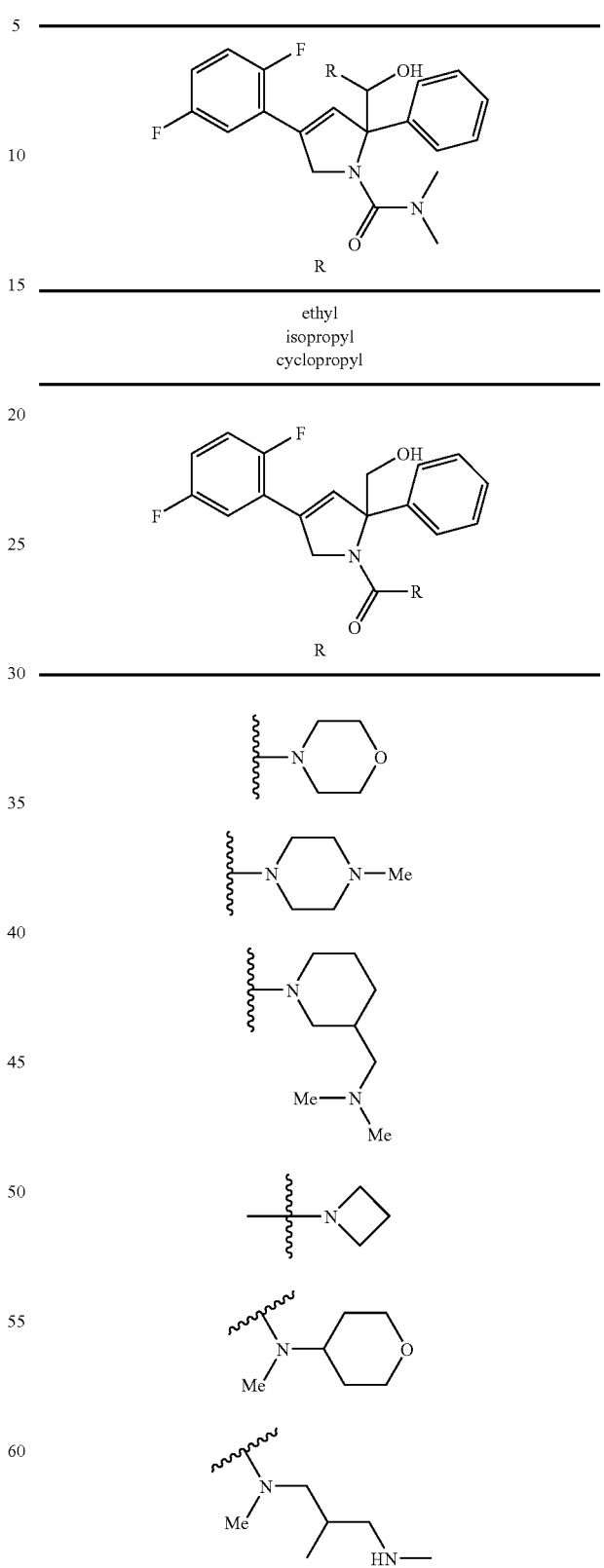

-continued
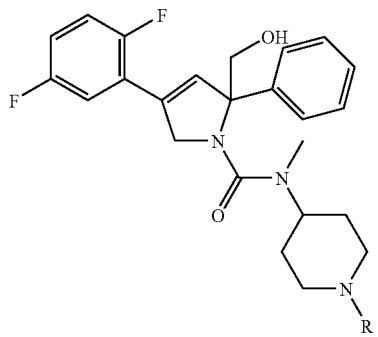
| R |
|---|
| H |
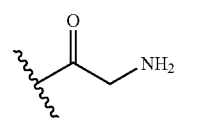
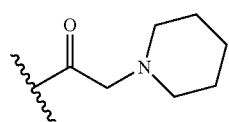
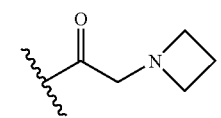
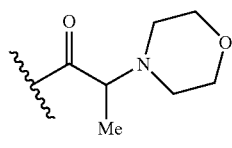
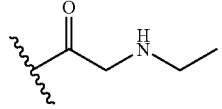
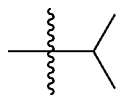
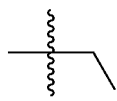
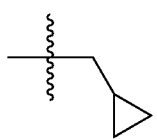
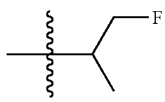
-continued
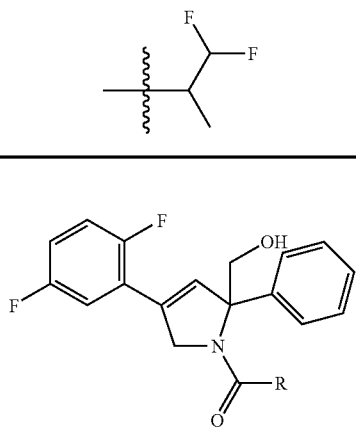
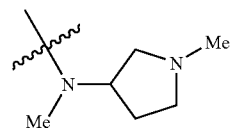
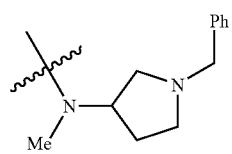
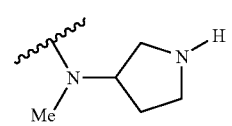
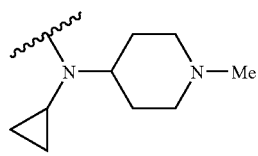
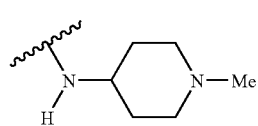
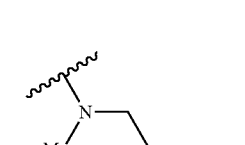
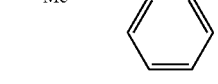

-continued
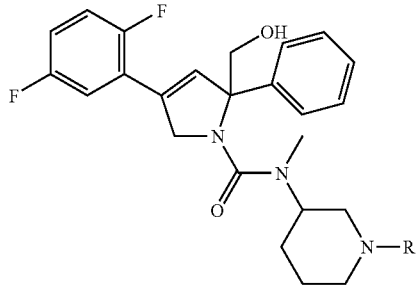
R
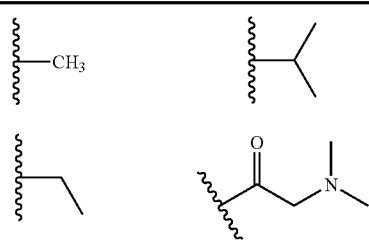
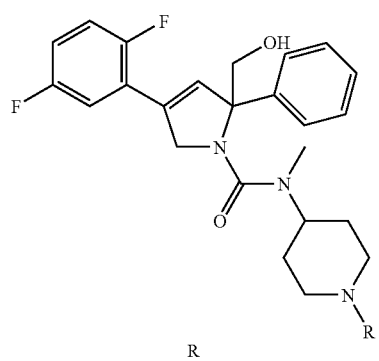
R
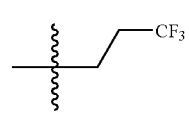
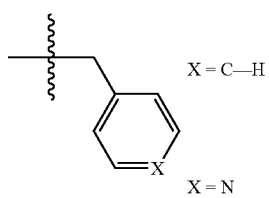  X = C—H
                     X = N
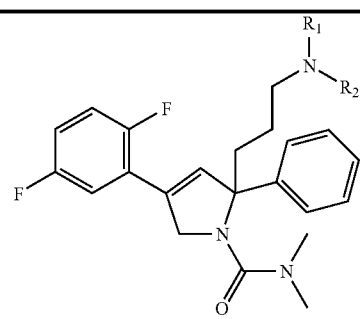
R₁         R₂
-continued
| | |
|---|---|
| H | 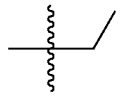 |
| H | 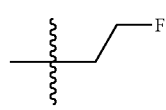 |
| H | 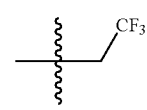 |
| H | 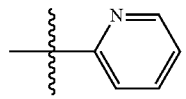 |
| H H | 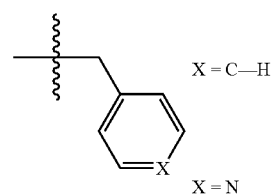 X = C—H <br> X = N |
| H H | —CH₂CH₂CH₂CH₂CH₂— <br> 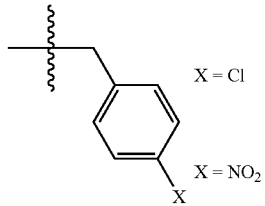 X = Cl <br> X = NO₂ |
| H | 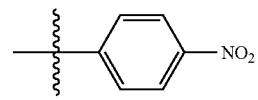 |
| CH₂CHF₂ CH₂CHF₂ | 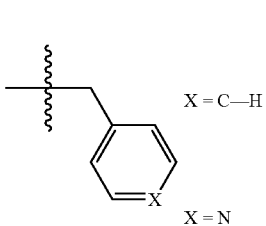 X = C—H <br> X = N |
| H | 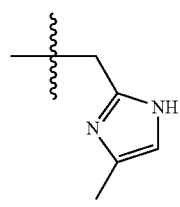 |

-continued

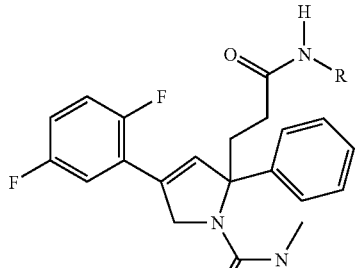

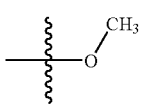

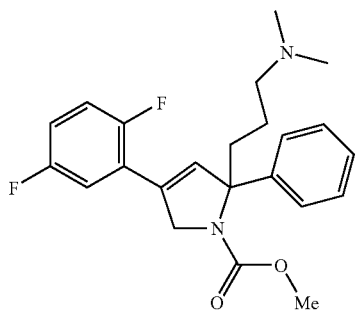

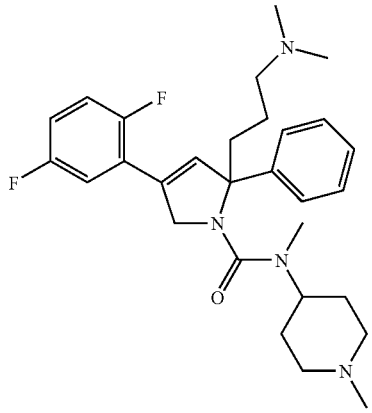

or a pharmaceutically acceptable salt or stereoisomer thereof.

Additional examples of the compounds of the instant invention are:

2-[(2-Aminoethoxy)methyl]-4-(2,5-difluorophenyl)-N,N-dimethyl-2-phenyl-2,5-dihydro-1H-pyrrole-1-carboxamide hydrochloride salt;

4-(2,5-Difluorophenyl)-2-({[2-(dimethylamino)ethyl]amino}methyl)-N,N-dimethyl-2-phenyl-2,5-dihydro-1H-pyrrole-1-carboxamide bis TFA salt;

2-(3-Aminopropyl)-4-(2,5-difluorophenyl)-N,N-dimethyl-2-phenyl-2,5-dihydro-1H-pyrrole-1-carboxamide hydrochloride salt;

4-(2,5-Difluorophenyl)-2-[3-(dimethylamino)propyl]-N,N-dimethyl-2-phenyl-2,5-dihydro-1H-pyrrole-1-carboxamide TFA salt;

4-(2,5-difluorophenyl)-N-[1-(glycyl)piperidin-4-yl]-2-(hydroxymethyl)-N-methyl-2-phenyl-2,5-dihydro-1H-pyrrole-1-carboxamide TFA salt;

3-[(2S)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine bis-TFA salt;

3-[(2R)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine bis-TFA salt;

4-(2,5-difluorophenyl)-2-[3-(dimethylamino)propyl]-N-methyl-N-(1-methylpiperidin-4-yl)-2-phenyl-2,5-dihydro-1H-pyrrole-1-carboxamide bis-TFA salt;

4-(2,5-difluorophenyl)-2-[3-(ethylamino)propyl]-N,N-dimethyl-2-phenyl-2,5-dihydro-1H-pyrrole-1-carboxamide TFA salt;

4-(2,5-difluorophenyl)-N,N-dimethyl-2-phenyl-2-{3-[(pyridin-4-ylmethyl)amino]propyl}-2,5-dihydro-1H-pyrrole-1-carboxamide bis-TFA salt; and 4-(2,5-difluorophenyl)-N,N-dimethyl-2-(3-{[(4-methyl-1H-imidazol-2-yl)methyl]amino}propyl)-2-phenyl-2,5-dihydro-1H-pyrrole-1-carboxamide bis-TFA salt.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

When any variable (e.g. $R^{10}$, $R^{11}$, $R^{12}$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —$CH_2$—, —$CH_2CH_2$— and the like.

When used in the phrases "$C_1$-$C_6$ aralkyl" and "$C_1$-$C_6$ heteroaralkyl" the term "$C_1$-$C_6$" refers to the alkyl portion of the moiety and does not describe the number of atoms in the aryl and heteroaryl portion of the moiety.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

Preferably, heterocycle is selected from 2-azepinone, benzimidazolyl, 2-diazapinone, imidazolyl, 2-imidazolidinone, indolyl, isoquinolinyl, morpholinyl, piperidyl, piperazinyl, pyridyl, pyrrolidinyl, 2-piperidinone, 2-pyrimidinone, 2-pyrollidinone, quinolinyl, tetrahydrofuryl, tetrahydroisoquinolinyl, and thienyl.

As appreciated by those of skill in the art, "halo" or "halogen" as used herein is intended to include chloro, fluoro, bromo and iodo.

The alkyl, alkenyl, alkynyl, cycloalkyl, aryl, heteroaryl and heterocyclyl substituents may be substituted or unsubstituted, unless specifically defined otherwise. For example, a ($C_1$-$C_6$)alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition:

—C=O)$CH_2$CH(OH)$CH_3$, —(C=O)OH, —$CH_2$(OH) $CH_2$CH(O), and so on.

In certain instances, $R^{12}$ and $R^{13}$, $R^c$ and $R^{c'}$ and $R^f$ and $R^{f'}$ are defined such that they can be taken together with the nitrogen to which they are attached to form a monocyclic or bicyclic heterocycle with 5-7 members in each ring and optionally containing, in addition to the nitrogen, one or two additional heteroatoms selected from N, O and S, said heterocycle optionally substituted with one or more substituents selected from $R^{11}$. Examples of the heterocycles that can thus be formed include, but are not limited to the following, keeping in mind that the heterocycle is optionally substituted with one or more (and preferably one, two or three) substituents chosen from $R^{11}$:

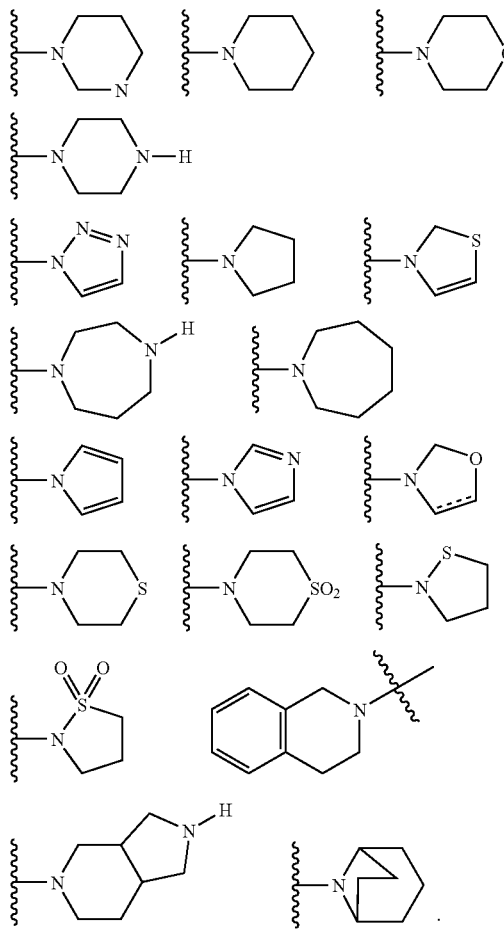

In certain instances, $R^d$ and $R^{d'}$ are defined such that they can be taken together with the phosphorous to which they are attached to form a monocyclic heterocycle with 5-7 members in the ring and optionally containing, in addition to the nitrogen, one or two additional heteroatoms selected from $NR^e$, O and S, said heterocycle optionally substituted with one or more substituents selected from $R^{11}$. Examples of the heterocycles that can thus be formed include, but are not limited to the following, keeping in mind that the heterocycle is optionally substituted with one or more (and preferably one or two) substituents chosen from $R^{11}$:

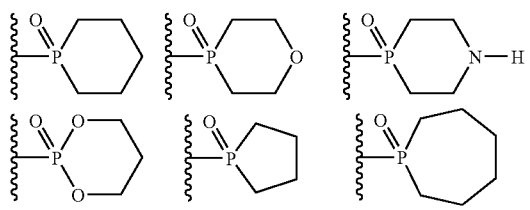

-continued

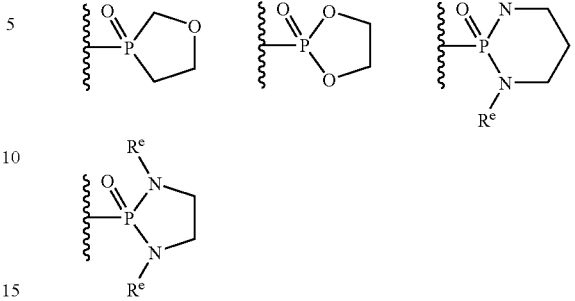

Preferably $R^1$ is selected from $(C=O)NR^cR^{c'}$, $-(C=O)$ $C_1$-$C_{10}$ alkyl and $-SO_2C_1$-$C_6$ alkyl, optionally substituted with one to three substituents selected from $R^{10}$. More preferably, $R^1$ is aminocarbonyl, N,N-dimethylaminocarbonyl, methylsulfonyl, ethylsulfonyl or aminomethylcarbonyl, optionally substituted with one to three substituents selected from $R^{10}$.

Preferably $R^2$ is selected from aryl, optionally substituted with one to three substituents selected from $R^{10}$. More preferably, $R^2$ is phenyl, optionally substituted with one to three substituents selected from halo.

In an embodiment, $R^2$ is phenyl.

Also prefered is the definition of $R^4$, $R^5$ and $R^7$ as H.

Preferably $R^3$ is selected from $-C_1$-$C_{10}$ alkyl-O—$R^g$ and $-C_1$-$C_{10}$ alkyl-$NR^fR^{f'}$, optionally substituted with one to two substituents selected from $R^{10}$.

Preferably $R^6$ is selected from aryl, optionally substituted with one to three substituents selected from $R^{10}$. More preferably, $R^6$ is phenyl, optionally substituted with one to three substituents selected from halo.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

Schemes

As shown in Scheme A, key 2,2-disubstituted dihydropyrrole intermediate A-8 may be obtained from readily available suitably substituted α-phenylglycines. Following the procedure described by Van Betsbrugge et. al. (*Tetrahedron,* 1997, 53, 9233-9240) the α-allyl-α-phenylglycine is prepared. Reduction of the ester and cyclization with carbonyldiimidazole provides intermediate A-4. Ruthenium oxidation of the allylic olefin, followed by ester formation and alkylation of the nitrogen provides intermediate A-5. Cyclization and decarboxylation results in intermediate A-6. The ring carbonyl can then be utilized to incorporate a suitably substituted phenyl moiety. Subsequent saponification and oxygen protection leads to the protected intermediate A-8. The ring nitrogen may then be reacted with triphosgene and a variety of substituted amines to provide the compounds of the instant invention A-9.

As shown in Schemes B and C, the hydroyl moiety of A-9 may undergo alkylation with a variety of reagents.

Scheme D illustrates attachment of a suitably substituted amino acid residue to the dihydropyrrole nitrogen. It is advantageous to first N-protect intermediate A-8 and fully functionalize the 2-position side-chain. Subsequent deprotection and reaction with a N-blocked suitably substituted amino acid provides the instant compound D-4. The group R$^{SC}$ represents a substituent sidechain, preferably a sidechain of an amino acid.

As illustrated in Schemes E, replacement of the hydroxyl moiety of compound A-9 with a suitably substituted amine proceeds through the corresponding aldehyde E-1, followed by reductive alkylation results in the instant compound E-2.

Scheme F illustrates the syntheses of compounds of the instant invention that incorporate a monosubstituted N-aminocarbonyl group.

Scheme G illustrates homologation of the 2-alkyl sidechain to provide the instant compounds G-3 and G4.

As illustrated in Scheme H, suitably substituted hydroxyalkylamides may also be prepared.

Schemes I to K illustrate further modifications of the C-2 alkyl sidechain starting with the intermediate aldehyde E-1. Thus in Scheme I, the aldehyde E-1 is treated with a Grignard reagent, such as an alkyl Grignard, to provide the hydroxy compound I-1.

Scheme J illustrates homologation of the C-2 side chain. The aldehyde E-1 is treated with a phosphonoacetate and the conjugated double bond is then reduced to provide the ester J-1. Subsequent reduction of the ester and oxidation of the alcohol provides the aldehyde J-3, which can reductively alkylate a suitably substituted amine to provide the instant compound J-4. Further alkylation of J-4 is also illustrated.

Scheme K illustrates fluorination of the C-2 sidechain and subsequent conversion of the hydroxyl moiety to an amine via displacement of the corresponding triflate with sodium azide.

Scheme L illustrates incorporation of a difluoromethyl moiety into the C-2 sidechain.

SCHEME A

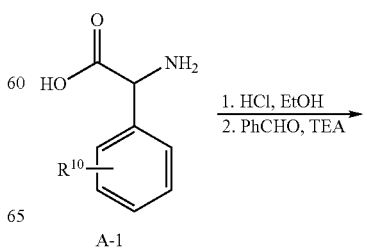

A-1

-continued
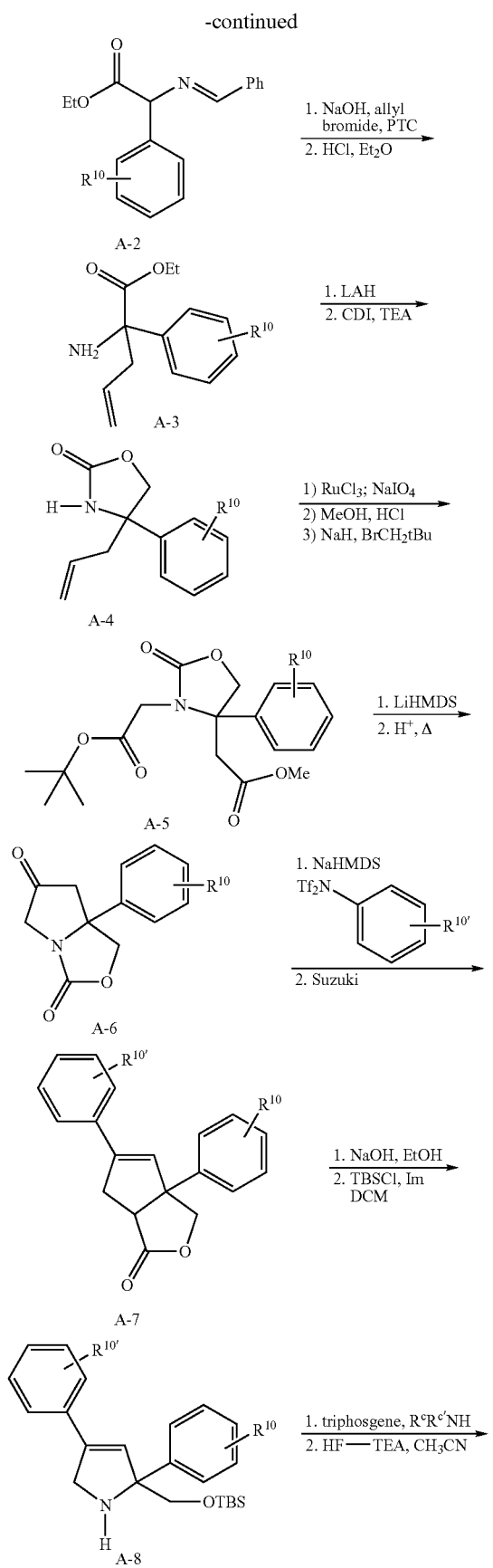
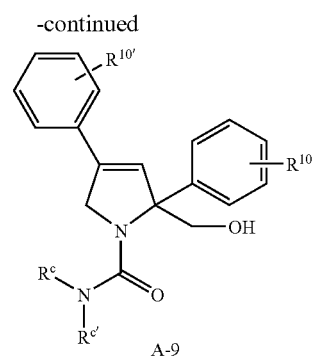
SCHEME B
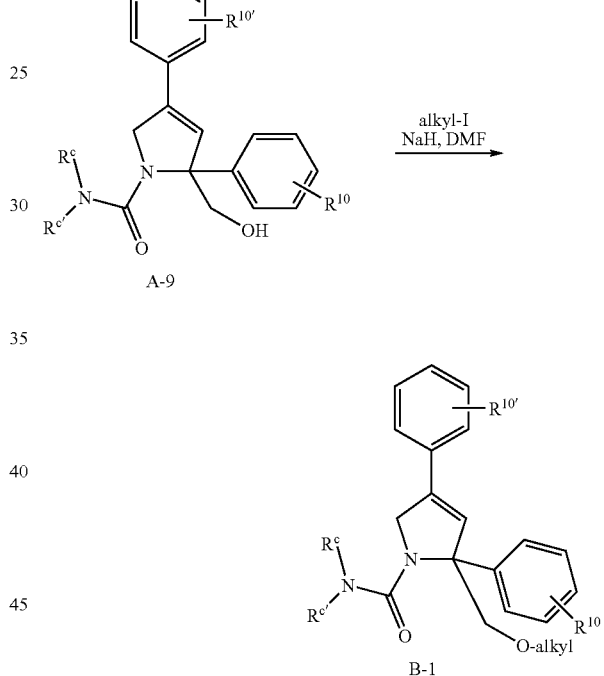
SCHEME C
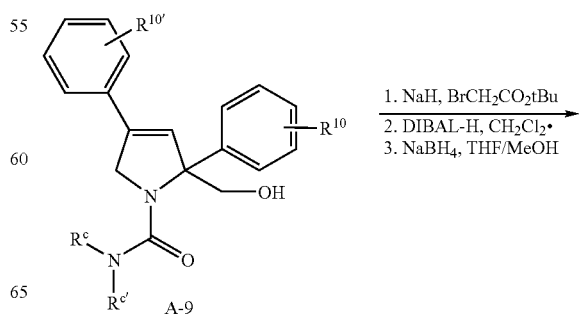

-continued
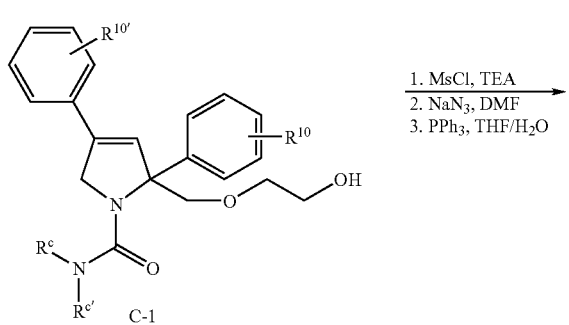
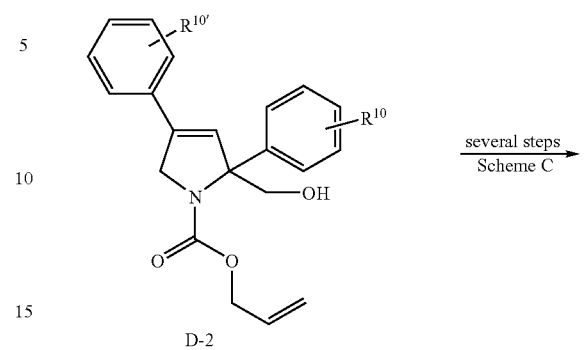
SCHEME D
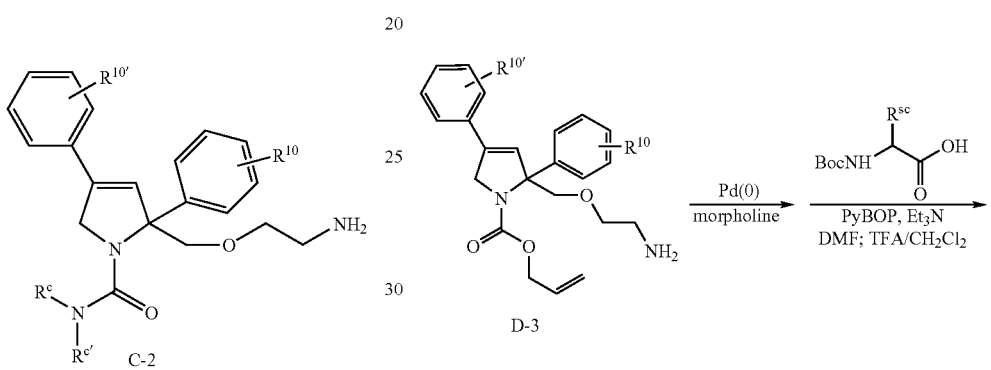
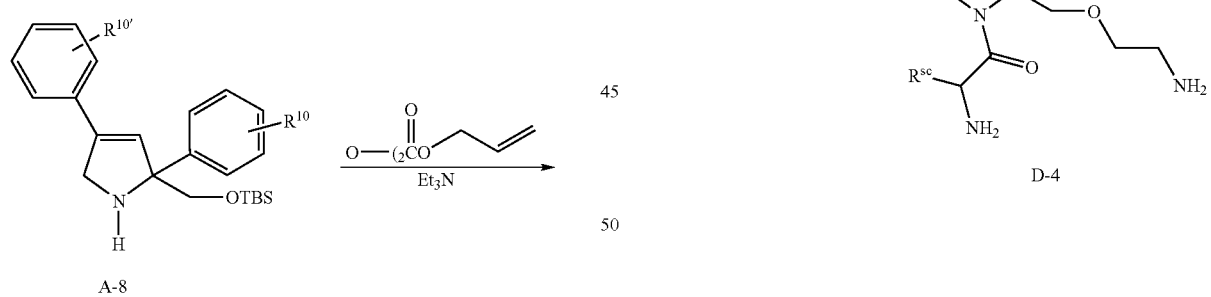
SCHEME E
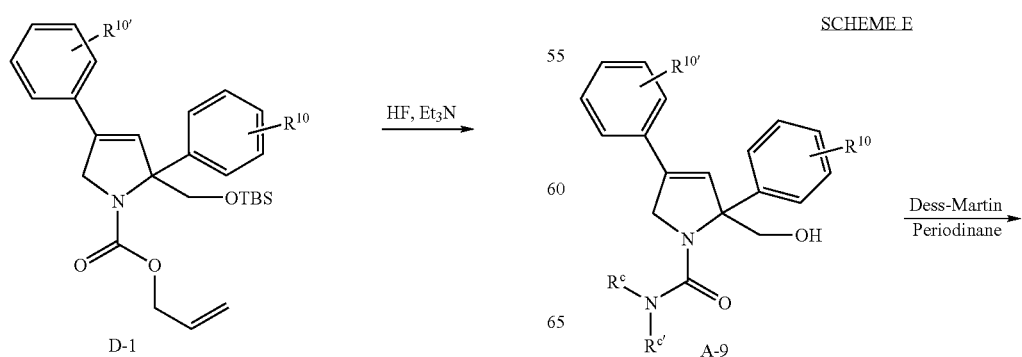

-continued
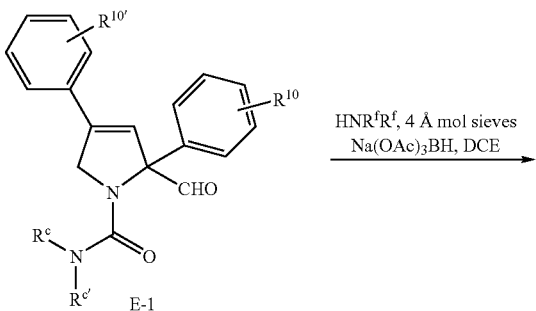
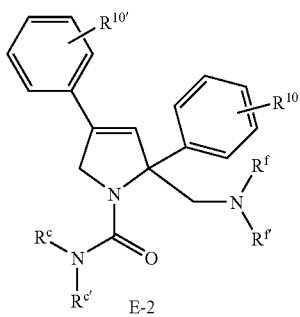
SCHEME F
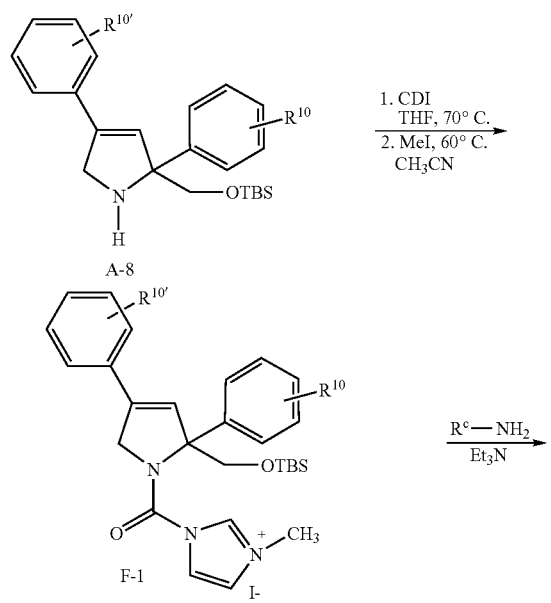
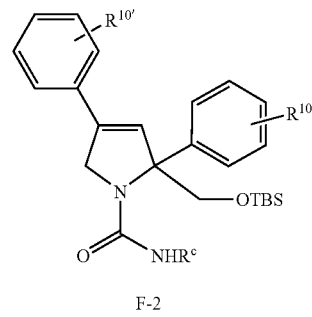
SCHEME G
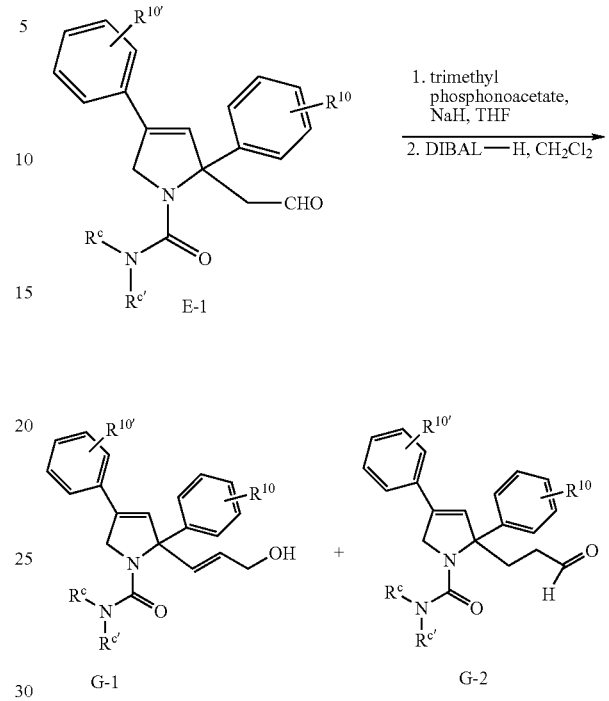
SCHEME H
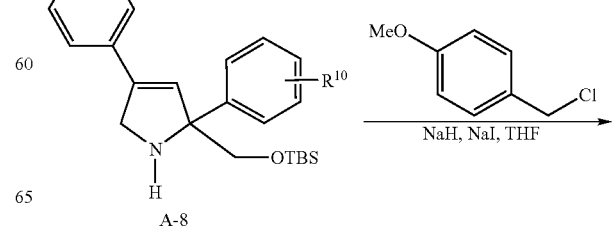

-continued
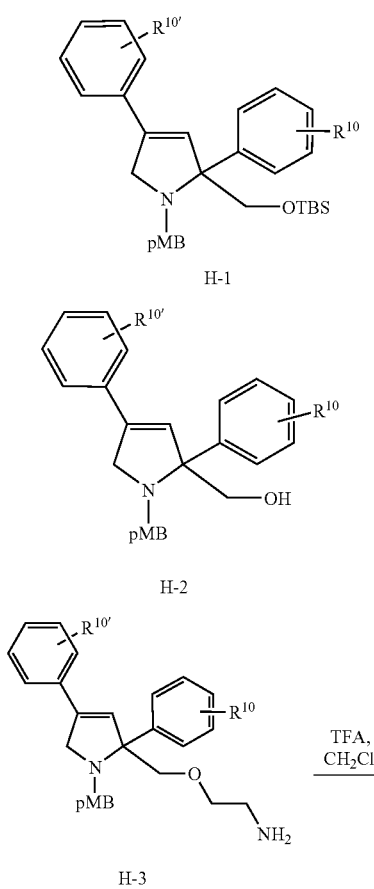
SCHEME I
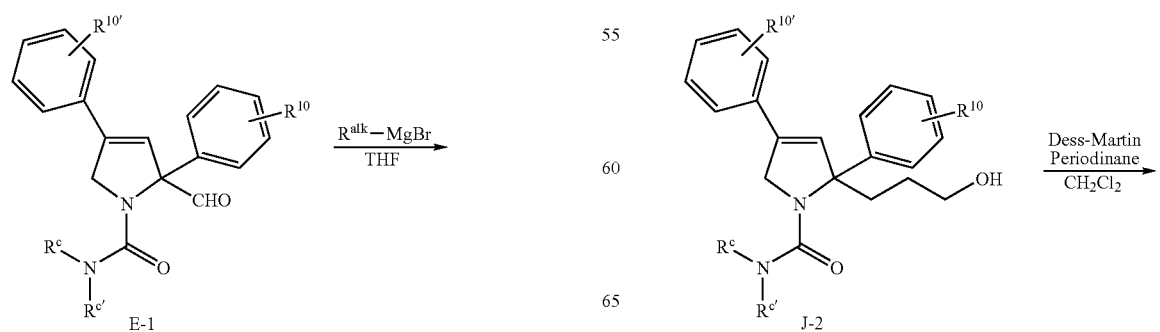
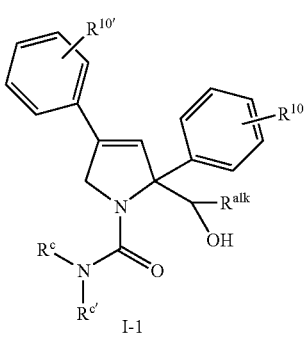
SCHEME J
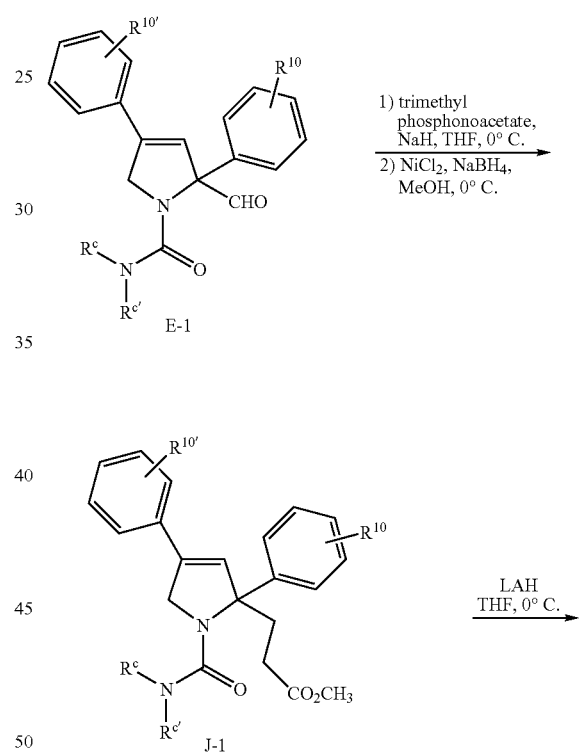

-continued
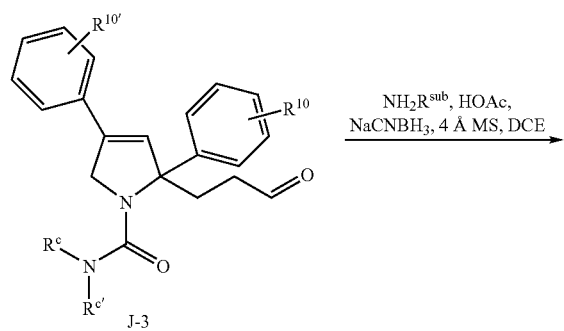
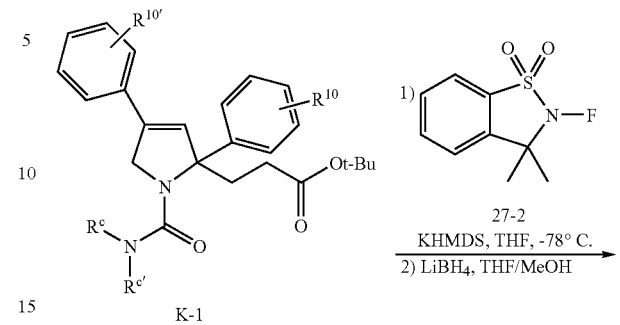
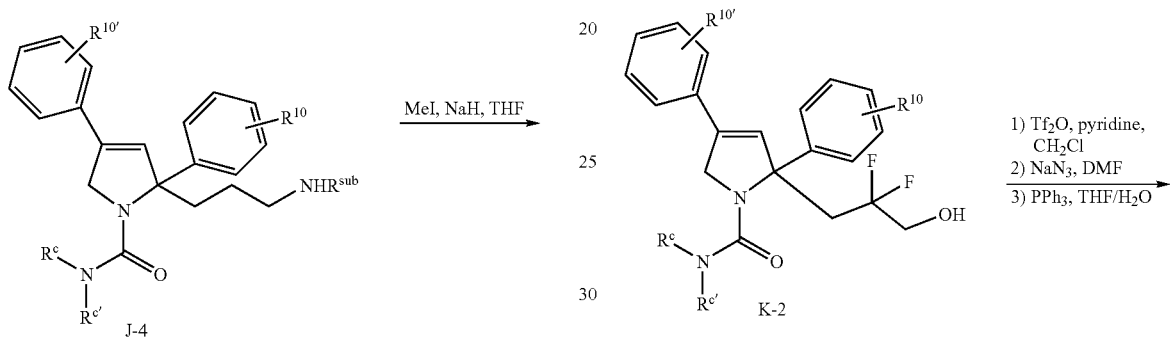
SCHEME K
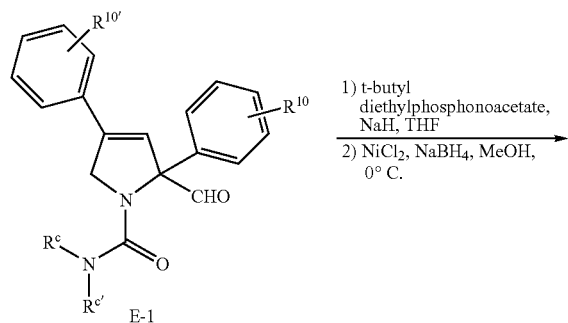
SCHEME L
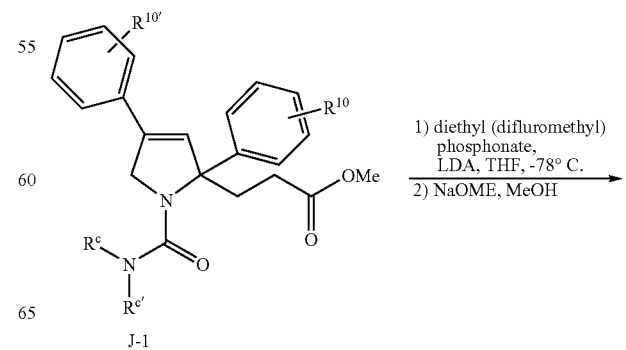

-continued

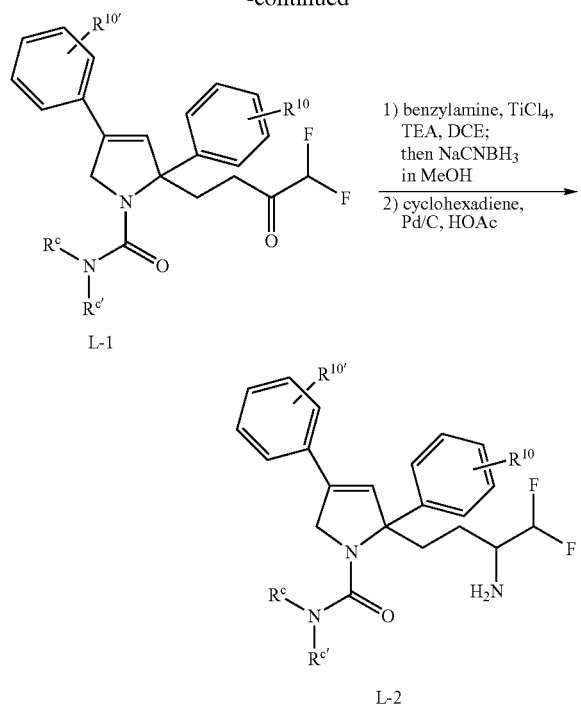

Utilities

The compounds of the invention find use in a variety of applications. As will be appreciated by those in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a preferred embodiment, the compounds of the invention are used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to and/or modulate the activity of a mitotic kinesin. In a preferred embodiment, the mitotic kinesin is a member of the bimC subfamily of mitotic kinesins (as described in U.S. Pat. No. 6,284,480, column 5). In a further preferred embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See PCT Publ. WO 01/31335: "Methods of Screening for Modulators of Cell Proliferation and Methods of Diagnosing Cell Proliferation States", filed Oct. 27, 1999, hereby incorporated by reference in its entirety. In addition, other mitotic kinesins may be inhibited by the compounds of the present invention.

The compounds of the invention are used to treat cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple mycloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological:

uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

The compounds of the instant invention may also be useful as antifungal agents, by modulating the activity of the fungal members of the bimC kinesin subgroup, as is described in U.S. Pat. No. 6,284,480.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteosome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768 and WO 01/98278, and pending U.S. Ser. Nos. 60/338,779 (filed Dec. 6, 2001), 60/338,344 (filed Dec. 6, 2001), 60/338,383 (filed Dec. 6, 2001), 60/338, 380 (filed Dec. 6, 2001), 60/338,379 (filed Dec. 6, 2001) and PCT Publication WO 03/39460 May 15, 2003). In an embodiment inhibitors of mitotic kinesins include, but are not limited to inhibitors of KSP, inhibitors of MELP1, inhibitors of CENP-E, inhibitors of MCAK and inhibitors of Rab6-KIPL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820, 850 and 4,916,239), pravastatin (RAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LEPITOR®; see U.S. Pat. Nos. 5,273,995, 4,681,893, 5,489,691 and 5,342, 952) and cerivastatin (also known as rivastatin and BAY-CHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

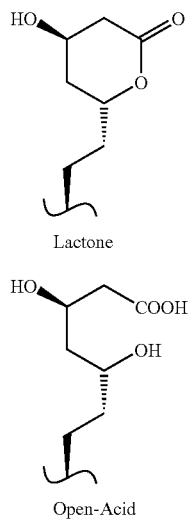

Lactone

Open-Acid

In HMG-CoA reductase inhibitors where an open-acid form can exist, salt and ester forms may be formed from the open-acid and all such forms are included within the meaning of the term "HMG-CoA reductase inhibitor" as used herein. In an embodiment, the HMG-CoA reductase inhibitor is selected from lovastatin and simvastatin, and in a further embodiment, simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)-1-methyl-2(1H)quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl) methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl} benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl) benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2'] bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6, 10:12,16-dimetheno-1H-imidazo[4,3-c][1,11,4] dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo [d]imidazo[4,3-k][1,6,9, 12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359.

For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAPIa inhibitors have been described in PCT Publication WO 03/013,526 and U.S. Ser. No. 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

The combinations with NSAD's are directed to the use of NSAD's which are potent COX-2 inhibiting agents. For purposes of this specification an NSAID is potent if it possess an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone; and

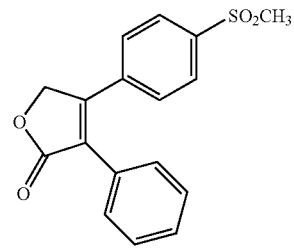

5-chloro-3-(4-methylsulfonyl)phenyl-2-(2-methyl-5-pyridinyl)pyridine;

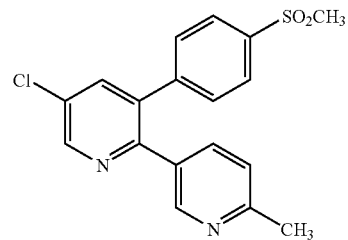

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

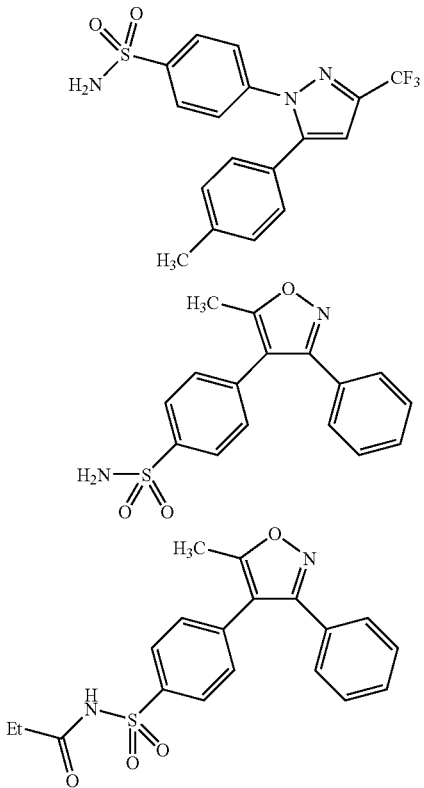

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine*, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. For the treatment or prevention of emesis that may result upon administration of the instant compounds, conjunctive therapy with an anti-emesis agent selected from a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913,0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

Thus, the scope of the instant invention encompasses the use of the instantly claimed compounds in combination with a second compound selected from:
1) an estrogen receptor modulator,
2) an androgen receptor modulator,
3) retinoid receptor modulator,
4) a cytotoxic/cytostatic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) a PPAR-γ agonists,
12) a PPAR-δ agonists,
13) an inhibitor of inherent multidrug resistance,
14) an anti-emetic agent,
15) an agent useful in the treatment of anemia,
16) an agent useful in the treatment of neutropenia,
17) an immunologic-enhancing drug,
18) an inhibitor of cell proliferation and survival signaling, and
19) an agent that interfers with a cell cycle checkpoint.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from:
 1) an estrogen receptor modulator,
 2) an androgen receptor modulator,
 3) a retinoid receptor modulator,
 4) a cytotoxic/cytostatic agent,
 5) an antiproliferative agent,
 6) a prenyl-protein transferase inhibitor,
 7) an HMG-CoA reductase inhibitor,
 8) an HIV protease inhibitor,
 9) a reverse transcriptase inhibitor,
 10) an angiogenesis inhibitor,
 11) PPAR-γ agonists,
 12) PPAR-δ agonists,
 13) an inhibitor of inherent multidrug resistance,
 14) an anti-emetic agent,
 15) an agent useful in the treatment of anemia,
 16) an agent useful in the treatment of neutropenia,
 17) an immunologic-enhancing drug,
 18) an inhibitor of cell proliferation and survival signaling, and
 19) an agent that interfers with a cell cycle checkpoint.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from:
 1) an estrogen receptor modulator,
 2) an androgen receptor modulator,
 3) a retinoid receptor modulator,
 4) a cytotoxic/cytostatic agent,
 5) an antiproliferative agent,
 6) a prenyl-protein transferase inhibitor,
 7) an HMG-CoA reductase inhibitor,
 8) an HIV protease inhibitor,
 9) a reverse transcriptase inhibitor,
 10) an angiogenesis inhibitor, and
 11) a PPAR-γ agonist,
 12) a PPAR-δ agonists;
 13) an inhibitor of cell proliferation and survival signaling, and
 14) an agent that interfers with a cell cycle checkpoint.

The invention further comprises the use of the instant compounds in a method to screen for other compounds that bind to KSP. To employ the compounds of the invention in a method of screening for compounds that bind to KSP kinesin, the KSP is bound to a support, and a compound of the invention (which is a mitotic agent) is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a preferred embodiment, the mitotic agent (the compound of the invention) is labeled, for example, with a fluorescent or radioactive moiety and binding determined directly. For example, this may be done by attaching all or a portion of KSP to a solid support, adding a labeled mitotic agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific-binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the mitotic agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays may be done by combining KSP and a drug candidate in a first sample. A second sample comprises a mitotic agent, KSP and a drug candidate. This may be performed in either the presence or absence of microtubules. The binding of the drug candidate is determined for both samples, and a change, or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a preferred embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between about 4 and about 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the mitotic agent, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce nonspecific or background interactions. Also reagents that otherwise improve the efficiency of the assay, such as protease inhibitors, nuclease inhibitors, anti-microbial agents, etc., may be used. The mixture of components may be added in any order that provides for the requisite binding.

These and other aspects of the invention will be apparent from the teachings contained herein.

Assays

The compounds of the instant invention described in the Examples were tested by the assays described below and were found to have kinase inhibitory activity. Other assays are known in the literature and could be readily performed by those of skill in the art (see, for example, PCT Publication WO 01/30768, May 3, 2001, pages 18-22).

I. Kinesin ATPase In Vitro Assay

Cloning and Expression of Human Poly-histidine Tagged KSP Motor Domain (KSP(367H))

Plasmids for the expression of the human KSP motor domain construct were cloned by PCR using a pBluescript full length human KSP construct (Blangy et al., Cell, vol. 83, pp 1159-1169, 1995) as a template. The N-terminal primer 5'-GCAACGATTAATATGGCGTCGCAGC-CAAATTCGTCTGCGAAG (SEQ.ID.NO.: 1) and the C-terminal primer 5'-GCAACGCTCGAGTCAGTGAT GATGGTGGTGATGCTGATTCACTTCAG-GCTTATTCAATAT (SEQ.ID.NO.: 2) were used to amplify the motor domain and the neck linker region. The PCR products were digested with AseI and XhoI, ligated into the NdeI/XhoI digestion product of pRSETa (Invitrogen) and transformed into *E. coli* BL21 (DE3).

Cells were grown at 37° C. to an $OD_{600}$ of 0.5. After cooling the culture to room temperature expression of KSP was induced with 100 µM IPTG and incubation was continued overnight. Cells were pelleted by centrifugation and washed once with ice-cold PBS. Pellets were flash-frozen and stored −80° C.

Protein Purification

Cell pellets were thawed on ice and resuspended in lysis buffer (50 mM K-HEPES, pH 8.0, 250 mM KCl, 0.1% Tween, 10 mM imidazole, 0.5 mM Mg-ATP, 1 mM PMSF, 2 mM benzimidine, 1× complete protease inhibitor cocktail (Roche)). Cell suspensions were incubated with 1 mg/ml lysozyme and 5 mM β-mercaptoethanol on ice for 10 minutes, followed by sonication (3×30 sec). All subsequent procedures were performed at 4° C. Lysates were centrifuged at 40,000×g for 40 minutes. Supernatants were diluted and loaded onto an SP Sepharose column (Pharmacia, 5 ml cartridge) in buffer A (50 mM K-HEPES, pH 6.8, 1 mM $MgCl_2$, 1 mM EGTA, 10 µM Mg-ATP, 1 mM DTT) and eluted with a 0 to 750 mM KCl gradient in buffer A. Fractions containing KSP were pooled and incubated with Ni-NTA resin (Qiagen) for one hour. The resin was washed three times with buffer B (Lysis buffer minus PMSP and protease inhibitor cocktail), followed by three 15-minute incubations and washes with buffer B. Finally, the resin was incubated and washed for 15 minutes three times with buffer C (same as buffer B except for pH 6.0) and poured into a column. KSP was eluted with elution buffer (identical to buffer B except for 150 mM KCl and 250 mM imidazole). KSP-containing fractions were pooled, made 10% in sucrose, and stored at −80° C.

Microtubules are prepared from tubulin isolated from bovine brain. Purified tubulin (>97% MAP-free) at 1 mg/ml is polymerized at 37° C. in the presence of 10 µM paclitaxel, 1 mM DTT, 1 mM GTP in BRB80 buffer (80 mM K-PIPES, 1 mM EGTA, 1 mM $MgCl_2$ at pH 6.8). The resulting microtubules are separated from non-polymerized tubulin by ultracentrifugation and removal of the supernatant. The pellet, containing the microtubules, is gently resuspended in 10 µM paclitaxel, 1 mM DTT, 50 µg/ml ampicillin, and 5 µg/ml chloramphenicol in BRB80.

The kinesin motor domain is incubated with microtubules, 1 mM ATP (1:1 $MgCl_2$: Na-ATP), and compound at 23° C. in buffer containing 80 mM K-HEPES (pH 7.0), 1 mM EGTA, 1 mM DTT, 1 mM $MgCl_2$, and 50 mM KCl. The reaction is terminated by a 2-10 fold dilution with a final buffer composition of 80 mM HEPES and 50 mM EDTA. Free phosphate from the ATP hydrolysis reaction is measured via a quinaldine red/ammonium molybdate assay by adding 150 µl of quench C buffer containing a 2:1 ratio of quench A:quench B. Quench A contains 0.1 mg/ml quinaldine red and 0.14% polyvinyl alcohol; quench B contains 12.3 mM ammonium molybdate tetrahydrate in 1.15 M sulfuric acid. The reaction is incubated for 10 minutes at 23° C., and the absorbance of the phospho-molybdate complex is measured at 540 nm.

The compounds 1-9, 1-10, 2-1, 2-2, 2-3, 3-2, 4-1a, 4-3, 4-4, 5-1 to 5-4, 6-2 to 6-14, 7-3 8-1 to 8-7, 9-2 to 9-6, 10-1, 11-1, 12-1, 13-1, 14-1, 15-1, 16-1, 17-2 to 17-10, 18-2, 19-4 to 19-18, 20-2 to 20-3, 21-1, 22-1, 23-1, 24-2, 25-1, 26-1 to 26-3, 27-3 to 27-4, 28-3, 29-3, 30-2 to 30-4 and 31-3 in the Examples were tested in the above assay and found to have an $IC_{50} \leq 50$ µM.

II. Cell Proliferation Assay

Cells are plated in 96-well tissue culture dishes at densities that allow for logarithmic growth over the course of 24, 48, and 72 hours and allowed to adhere overnight. The following day, compounds are added in a 10-point, one-half log titration to all plates. Each titration series is performed in triplicate, and a constant DMSO concentration of 0.1% is maintained throughout the assay. Controls of 0.1% DMSO alone are also included. Each compound dilution series is made in media without serum. The final concentration of serum in the assay is 5% in a 200 µL volume of media. Twenty microliters of Alamar blue staining reagent is added to each sample and control well on the titration plate at 24, 48, or 72 hours following the addition of drug and returned to incubation at 37° C. Alamar blue fluorescence is analyzed 6-12 hours later on a CytoFluor II plate reader using 530-560 nanometer wavelength excitation, 590 nanometer emission.

A cytotoxic $EC_{50}$ is derived by plotting compound concentration on the x-axis and average percent inhibition of cell growth for each titration point on the y-axis. Growth of cells in control wells that have been treated with vehicle alone is defined as 100% growth for the assay, and the growth of cells treated with compounds is compared to this value. Proprietary in-house software is used to calculate percent cytotoxicity values and inflection points using logistic 4-parameter curve fitting. Percent cytotoxicity is defined as:

$$\% \text{ cytotoxicity:} (\text{Fluorescence}_{control} - \text{Flourescence}_{sample}) \times 100 \times (\text{Fluorescence}_{control})^{-1}$$

The inflection point is reported as the cytotoxic $EC_{50}$.

III. Evaluation of Mitotic Arrest and Apoptosis by FACS

FACS analysis is used to evaluate the ability of a compound to arrest cells in mitosis and to induce apoptosis by measuring DNA content in a treated population of cells.

Cells are seeded at a density of $1.4 \times 10^6$ cells per 6 cm² tissue culture dish and allowed to adhere overnight. Cells are then treated with vehicle (0.1% DMSO) or a titration series of compound for 8-16 hours. Following treatment, cells are harvested by trypsinization at the indicated times and pelleted by centrifugation. Cell, pellets are rinsed in PBS and fixed in 70% ethanol and stored at 4° C. overnight or longer.

For FACS analysis, at least 500,000 fixed cells are pelleted and the 70% ethanol is removed by aspiration. Cells are then incubated for 30 min at 4° C. with RNase A (50 Kunitz units/ml) and propidium iodide (50 µg/ml), and analyzed using a Becton Dickinson FACSCaliber. Data (from 10,000 cells) is analyzed using the Modfit cell cycle analysis modeling software (Verity Inc.).

An $EC_{50}$ for mitotic arrest is derived by plotting compound concentration on the x-axis and percentage of cells in the G2/M phase of the cell cycle for each titration point (as measured by propidium iodide fluorescence) on the y-axis. Data analysis is performed using the SigmaPlot program to calculate an inflection point using logistic 4-parameter curve fitting. The inflection point is reported as the $EC_{50}$ for mitotic arrest. A similar method is used to determine the compound $EC_{50}$ for apoptosis. Here, the percentage of apoptotic cells at each titration point (as determined by propidium iodide fluorescence) is plotted on the y-axis, and a similar analysis is carried out as described above.

VI. Immunofluorescence Microscopy to Detect Monopolar Spindles

Methods for immunofluorescence staining of DNA, tubulin, and pericentrin are essentially as described in Kapoor et al. (2000) J. Cell Biol. 150: 975-988. For cell culture studies, cells are plated on tissue culture treated glass chamber slides and allowed to adhere overnight. Cells are then incubated with the compound of interest for 4 to 16 hours. After incubation is complete, media and drug are aspirated and the chamber and gasket are removed from the glass slide. Cells are then permeabilized, fixed, washed, and blocked for nonspecific antibody binding according to the referenced protocol. Paraffin-embedded tumor sections are deparaffinized with xylene and rehydrated through an ethanol series prior to blocking. Slides are incubated in primary antibodies (mouse monoclonal anti-α-tubulin antibody, clone DM1A from Sigma diluted 1:500; rabbit polyclonal anti-pericentrin antibody from Covance, diluted 1:2000) overnight at 4° C. After washing, slides are incubated with conjugated secondary antibodies (FITC-conjugated donkey anti-mouse IgG for tubulin; Texas red-conjugated donkey anti-rabbit IgG for pericentrin) diluted to 15 µg/ml for one hour at room temperature. Slides are then washed and counterstained with Hoechst 33342 to visualize DNA. Immunostained samples are imaged with a 100× oil immersion objective on a Nikon epifluorescence microscope using Metamorph deconvolution and imaging software.

EXAMPLES

Examples provided are intended to assist in a further understanding of the invention. Particular materials employed, species and conditions are intended to be illustrative of the invention and not limiting of the reasonable scope thereof.

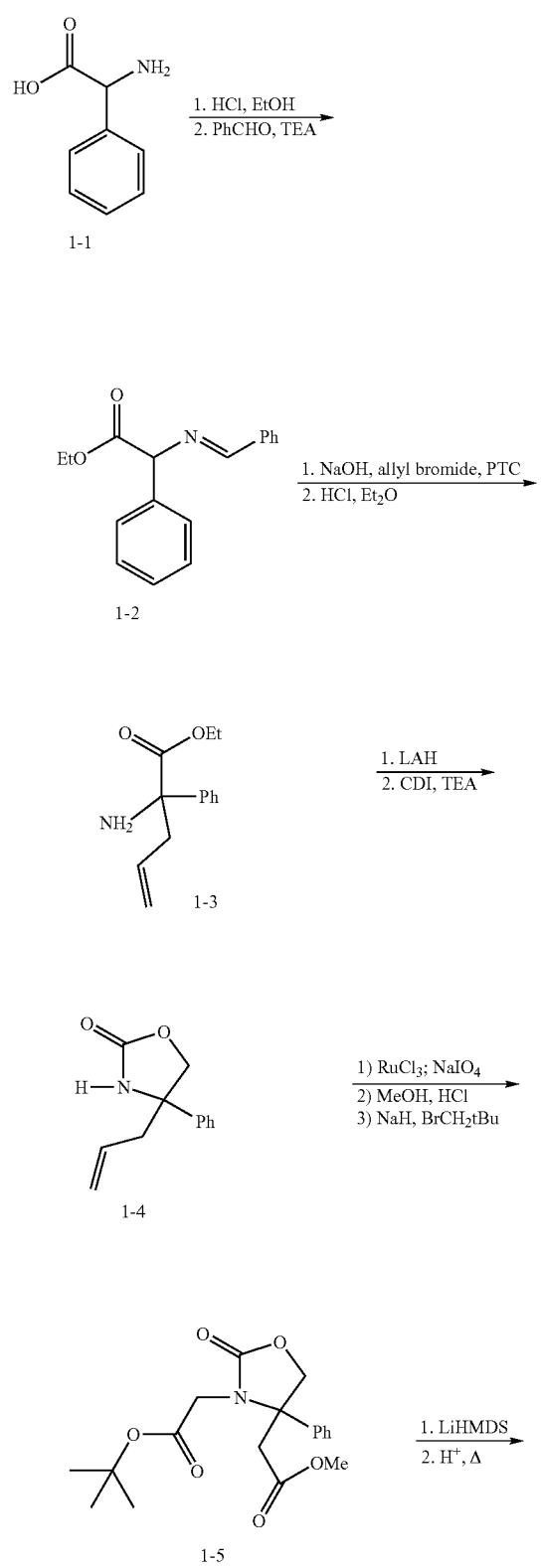

SCHEME 1

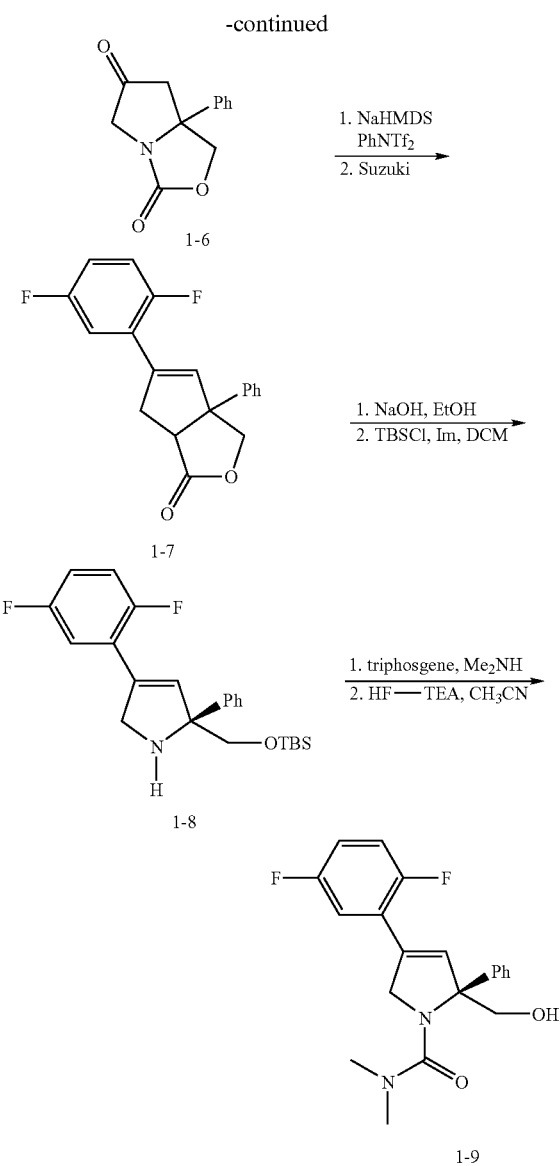

Step 1: 4-Allyl-4-phenyl-1,3-oxazolidin-2-one (1-4)

To a suspension of 15.8 g (416 mmol) of LAH powder in 600 mL of diethyl ether was added 18.3 g (90 mmol) of α-allyl-α-phenylglycine ethyl ester (1-3) (prepared according to: Van Betsbrugge et. al. *Tetrahedron*, 1997, 53, 9233-9240) in 75 mL of diethyl ether at such a rate as to maintain gentle reflux. After stirring overnight at room temperature, the reaction was carefully quenched with 27 mL of water, followed by 27 mL of 15% NaOH and finally 82 mL of water. A quantity of $Na_2SO_4$ was added, and the mixture was stirred for 1 h. The solids were then filtered off and the solution concentrated. The residue was dissolved in 300 mL of $CH_2Cl_2$, dried over $Na_2SO_4$, and concentrated to provide the amino alcohol as a colorless oil. The amino alcohol (4.5 g, 25 mmol) was dissolved in 50 mL of $CH_2Cl_2$ and cooled to 0° C. Following the addition of 5.4 mL (53 mmol) of triethylamine and 4.5 g (28 mmol) of 1,1'-carbonyldiimidazole, the mixture was warmed to room temperature and allowed to stir for 4 h. The reaction was then dumped into a separatory funnel, washed twice with 1M HCl, water, dried over $Na_2SO_4$, and concentrated to obtain oxazolidinone 1-4 as a colorless oil. Data for 1-4: $^1$HNMR (500 MHz, $CDCl_3$) δ 7.4-7.2 (m, 5H), 6.6 (s, 1H), 5.6-5.5 (m, 1H), 5.2 (m, 2H), 4.5 (d, 1H), 4.35 (d, 1H), 2.8 (m, 1H), 2.6 (m, 1H) ppm.

Step 2: Diester (1-5)

To a biphasic mixture of 14.8 g (73 mmol) of 1-4 and 110 mL of $CH_2Cl_2$, 110 mL of $CH_3CN$, and 320 mL of water was added approximately 200 mg of ruthenium(III) chloride hydrate. Sodium periodate (85.6 g, 400 mmol) was then added portion-wise over 1 h with rapid stirring. After the addition was complete, the reaction was allowed to stir for 4 h more at room temperature. The mixture was diluted with 500 mL of water and 1.5 L of EtOAc, and the solids were removed by filtration. The filtrate was placed in a separatory funnel, the phases separated, the aqueous phase extracted twice with EtOAc, the combined organic phases washed twice with brine, and dried over $Na_2SO_4$. Following concentration, the dark brown solid was dissolved in 250 mL of MeOH and HCl(g) was slowly passed through the solution at a rate so as not to increase the temperature of the solution above 35° C. After 5 min, the reaction was capped and allowed to stir at room temperature overnight. The volatiles were then removed on a rotary evaporator, and the residue was purified by silica gel chromatography with EtOAc/hexanes to provide 13.6 g (58 mmol) of the methyl ester as a viscous oil. This residue was then dissolved in 200 mL of THF, cooled to 0° C., and 10.3 mL (70 mmol) of tert-butyl bromoacetate was added, followed by 2.8 g of NaH (70 mmol of a 60% suspension). After the mixture was allowed to warm to room temperature and stir overnight, it was quenched with a saturated $NH_4Cl$ solution, and extracted twice with EtOAc. The combined organic layers were then washed with brine, dried over $Na_2SO_4$, concentrated, and the residue purified by silica gel chromatography with EtOAc/hexanes to provide 1-5 as a colorless oil. Data for 1-5: $^1$HNMR (500 MHz, $CDCl_3$) δ 7.4-7.3 (m, 5H), 4.65 (d, 1H), 4.55 (d, 1H), 3.9 (d, 1H), 3.65 (s, 3H), 3.5 (d, 1H), 3.35 (d, 1H), 3.2 (d, 1H), 1.4 (s, 9H) ppm. HRMS (ES) calc'd M+Na for $C_{18}H_{23}NO_6$: 372.1423. Found: 372.1412.

Step 3: 7a-Phenyldihydro-1H-pyrrolo[1,2-c][1,3]oxazole-3,6(5H)-dione (1-6)

To a solution of 18.6 g (53 mmol) of 1-5 in 150 mL of THF at −78° C. was added dropwise 58.6 mL (58.6 mmol) of a 1M solution of LiHMDS in THF. After stirring for 1 h at that temperature, the cooling bath was removed and the reaction was allowed to warm to room temperature and stir overnight. The mixture was quenched with a saturated $NH_4Cl$ solution, extracted twice with EtOAc, washed twice with brine, dried over $Na_2SO_4$ and concentrated. The residue was dissolved in 60 mL of formic acid and heated at 100° C. for 24 h. The volatiles were removed under vacuum and the residue was triturated with $CH_2Cl_2$/hexanes/$Et_2O$ to provide 1-6 as a beige solid. Data for 1-6: $^1$HNMR (500 MHz, $CDCl_3$) δ 7.5-7.3 (m, 5H), 4.7 (d, 1H), 4.3 (d, 1H), 4.2 (d, 1H), 3.5 (d, 1H), 3.1 (d, 1H), 2.95 (d, 1H), 2.9 (d, 1H) ppm.

Step 4: 6-(2,5-Difluorophenyl)-7a-phenyl-5,7a-dihydro-1H-pyrrolo[1,2-c][1,3]oxazol-3-one (1-7)

To a suspension of 2.2 g (10 mmol) of 1-7 in 150 mL of THF at −78° C. was added dropwise 12.2 mL (12.2 mmol) of a 1M solution of NaHMDS in THF. After stirring for 30 min, the solution was allowed to warm to 0° C. and held there for 1 h. The solution was then cooled back down to −78° C. and a solution of 4.35 g (12.2 mmol) of N-phenylbis(trifluoromethanesulphonimide) in 10 mL of THF was added. The cooling bath was removed and the mixture was allowed to warm to room temperature and stir overnight. The mixture was quenched with a saturated $NH_4Cl$ solution, extracted twice with EtOAc, washed twice with brine, dried over $Na_2SO_4$ and concentrated. The residue was dissolved in 75 mL of DME and 18 mL of water. To this mixture was added 1.29 g (30 mmol) of LiCl, 3.2 g (30 mmol) of $Na_2CO_3$, and 4.8 g (30 mmol) of 2,5-difluorophenylboronic acid. The solution was then degassed with $N_2$ for 1 minute, followed by the addition of 630 mg (0.5 mmol) of tetrakis(triphenylphosphine) palladium (0). The reaction was heated at 90° C. for 3 h, cooled to room temperature, diluted with saturated $NaHCO_3$, and extracted twice with EtoAc. The combined organic layers were washed with brine, dried over $Na_2SO_4$, concentrated, and the residue purified by silica gel chromatography with $CH_2Cl_2$/hexanes to provide 1-7 as a white solid. Data for 1-7: $^1HNMR$ (500 MHz, $CDCl_3$) δ 7.5-7.3 (m, 5H), 7.1-6.9 (m, 3H), 6.8 (s, 1H), 4.9 (d, 1H), 4.75 (d, 1H), 4.5 (d, 1H), 4.25 (d, 1H) ppm. HRMS (ES) calc'd M+H for $C_{18}H_{13}F_2NO_2$: 314.0987. Found: 314.0993.

Step 5: 2-({[tert-Butyl(dimethyl)silyl]oxy}methyl)-4-(2,5-difluorophenyl)-2-phenyl-2,5-dihydro-1H-pyrrole (1-8)

A suspension of 1.75 g (5.6 mmol) 1-7 in 15 mL of EtOH and 10 mL of 3 M NaOH was heated at 60° C. for 3 h, cooled to room temperature and dumped into a separatory funnel with EtOAc and brine. The layers were separated, the aqueous phase was extracted twice with EtOAc, the combined organic phases were washed twice with brine, dried over $Na_2SO_4$, and concentrated to provide a white solid. To this flask was added 30 mL of $CH_2Cl_2$, 1.5 g (22.3 mmol) of imidazole and 1.76 g (11.7 mmol) of TBSCl, and the resultant suspension was stirred overnight. The reaction was diluted with $CH_2Cl_2$, washed twice with water, dried over $Na_2SO_4$, concentrated, and the residue purified by silica gel chromatography with EtOAc/hexanes to provide 1-8 as a white solid. Data for 1-8: $^1HNMR$ (500 MHz, $CDCl_3$) δ 7.6-7.3 (m, 5H), 7.1-6.9 (m, 3H), 6.75 (s, 1H), 4.25 (d, 1H), 4.1 (d, 1H), 3.95 (d, 1H), 3.75 (d, 1H), 0.9 (s, 9H), 0.1 (s, 3H), 0.05 (s, 3H) ppm.

Step 6: 4-(2,5-Difluorophenyl)-2-(hydroxymethyl)-N,N-dimethyl-2-phenyl-2,5-dihydro-1H-pyrrole-1-carboxamide (1-9)

To 500 mg (1.24 mmol) of 1-8 in 15 mL of THF was added 260 μL (1.87 mmol) of triethylamine, the solution was cooled to 0° C., and 129 mg (0.44 mmol) of triphosgene was added. The highly viscous solution was stirred for 30 min, 203 mg (2.5 mmol) of dimethylamine hydrochloride and an additional 870 μL (6.22 mmol) of triethylamine were added, the reaction was warmed to room temperature and stirring was continued for 5 h. The mixture was dumped into a separatory funnel containing 10% aqueous $KHSO_4$ and EtOAc, the layers were separated, the organic phase was washed with brine, dried over $Na_2SO_4$, and concentrated to provide a pale yellow oil. This was then dissolved in 10 mL of dry $CH_3CN$, 600 μL (3.7 mmol) of triethylamine trihydrofluoride was added, and the reaction was allowed to stir at room temperature overnight. The reaction was quenched with saturated $NaHCO_3$, extracted twice with EtOAc, washed with brine, dried over $Na_2SO_4$, concentrated, and the residue purified by silica gel chromatography with EtOAc/hexanes to provide 1-9 as a white solid. Data for 1-9: $^1HNMR$ (500 MHz, $CDCl_3$) δ 7.4-7.2 (m, 5H), 7.1-6.9 (m, 3H), 6.3 (s, 1H), 5.5 (m, 1H), 4.85 (m, 1H), 4.65 (d, 1H), 4.4 (m, 1H), 4.0 (d, 1H), 3.0 (s, 6H) ppm. HRMS (ES) calc'd M+H for $C_{20}H_{20}F_2N_2O_2$: 359.1566. Found: 359.1567.

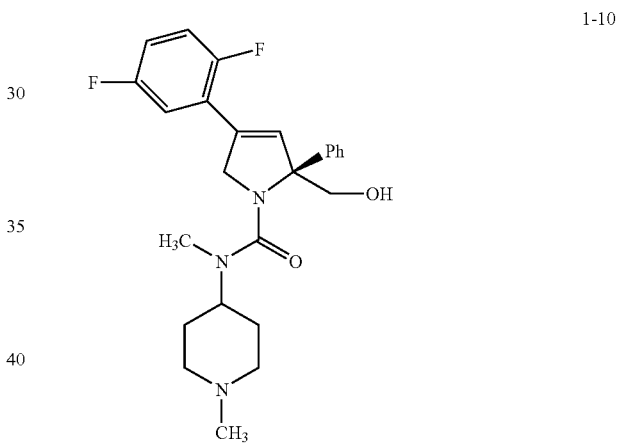

4-(2,5-Difluorophenyl)-2-(hydroxymethyl)-N-methyl-N-(1-methylpiperidin-4-yl)-2-phenyl-2,5-dihydro-1H-pyrrole-1-carboxamide (1-10)

A procedure analogous to that to obtain 1-9 was used to provide 1-10 as a white solid. Resolution of the enantiomers was carried out chromatographically using a Chiralpak AD© 5×50 cm column with 15% isopropanol in hexanes (with 0.1% diethylamine) at 70 mL/min. Analytical HPLC analysis of the eluent on a 4×250 mm Chiralpak AD® column with 15% isopropanol in hexanes (with 0.1% diethylamine) at 1 ml/min indicated that inactive enantiomer has $R_t$=11.4 min and the active enantiomer has $R_t$=15.6 min. Data for active enantiomer 1-10: $^1HNMR$ (500 MHz, $CDCl_3$) δ 7.4-7.2 (m, 5H), 7.1-6.9 (m, 3H), 6.25 (s, 1H), 4.85 (d, 1H), 4.6 (d, 1H), 4.4 (d, 1H), 4.0 (d, 1H), 3.9 (m, 1H), 3.3 (m, 2H), 3.0 (s, 3H) 2.6 (s, 3H), 2.5 (m, 2H), 2.2 (m, 2H), 2.0 (m, 1H), 1.8 (m, 1H) ppm.

SCHEME 2

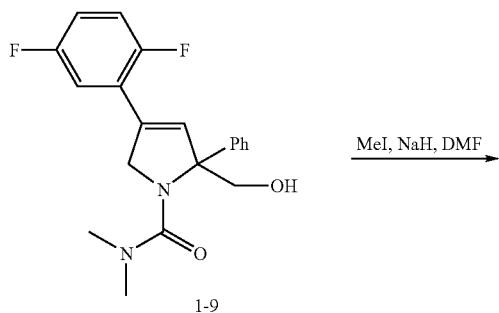

1-9

MeI, NaH, DMF →

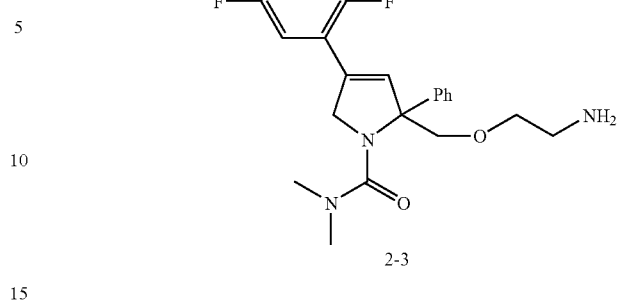

2-3

Step 1: 4-(2,5-Difluorophenyl)-2-(methoxymethyl)-N,N-dimethyl-2-phenyl-2,5-dihydro-1H-pyrrole-1-carboxamide (2-1)

To 25 mg (0.07 mmol) of 1-9 in 1 mL of DMF was added a small amount of MeI and NaH (60% suspension in oil) and the mixture was left to stir for 15 h at room temperature. The reaction was quenched with 1 drop of water and loaded directly onto a RP HPLC and eluted with $CH_3CN/H_2O$ with 0.1% TFA to provide 2-1 as a white solid. Data for 2-1: $^1$HNMR (500 MHz, $CDCl_3$) δ 7.4-7.2 (m, 5H), 7.1-6.9 (m, 3H), 6.4 (s, 1H), 4.8 (d, 1H), 4.7 (d, 1H), 4.45 (d, 1H), 4.35 (d, 1H), 3.4 (s, 3H), 2.8 (s, 6H) ppm. HRMS (MS) calc'd M+H for $C_{21}H_{22}F_2N_2O_2$: 373.1722. Found: 373.1722.

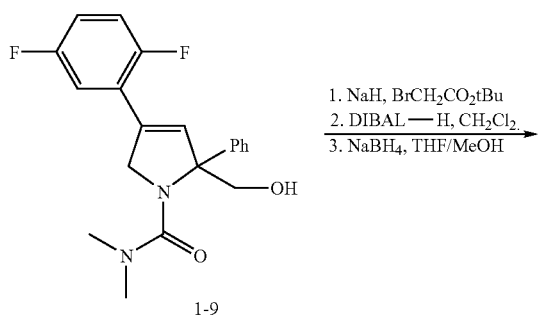

2-1

Step 2: 4-(2,5-Difluorophenyl)-2-[(2-hydroxyethoxy)methyl]-N,N-dimethyl-2-phenyl-2,5-dihydro-1H-pyrrole-1-carboxamide (2-2)

To 100 mg (0.28 mmol) of 1-9 in 3 mL of DMF at 0° C. was added 20 mg of NaH (0.6 mmol of a 60% suspension in oil), followed by 80 μL (0.6 mmol) of tert-butyl bromoacetate. After stirring for 2 h at 0° C., the reaction was quenched with a saturated $NH_4Cl$ solution, and extracted twice with EtOAc. The combined organic layers were then washed with brine, dried over $Na_2SO_4$, concentrated, and the residue purified by silica gel chromatography with EtOAc/hexanes to provide a colorless oil. This residue was dissolved in 10 mL of $CH_2Cl_2$, cooled to −78° C., and 900 μL of a 1M DIBAL-H solution in $CH_2Cl_2$ was added dropwise. After stirring for 45 min, the reaction was quenched with 500 μL of acetone, the cooling bath was removed, 15 mL of a 0.5 M tartaric acid solution was added, and the biphasic mixture was stirred for 1 h. The layers were separated, the organic was washed with water, dried over $Na_2SO_4$, and concentrated. The residue was then dissolved in 5 mL of THF and 1 mL of MeOH, and a small amount of $NaBH_4$ was added. After stirring for 15 min, the reaction was quenched with 1M HCl, extracted twice with EtOAc, washed with brine, dried over $Na_2SO_4$, concentrated, and the residue purified by silica gel chromatography with EtOAc/hexanes to provide 2-2 as a sticky white taffy. Data for 2-2: $^1$HNMR (500 MHz, $CDCl_3$) δ 7.4-7.2 (m, 5H), 7.1-6.9 (m, 3H), 6.4 (s, 1H), 4.8-4.6 (m, 3H), 4.2 (d, 1H), 3.8-3.7 (m, 2H), 3.7-3.5 (m, 2H), 2.85 (s, 6H) ppm. HRMS (ES) calc'd M+H for $C_{22}H_{24}F_2N_2O_3$: 403.1828. Found: 403.1824.

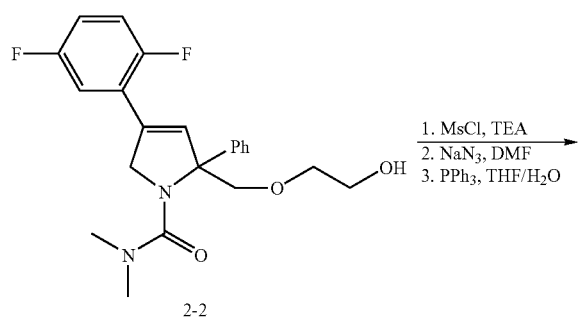

2-2

Step 3: 2-[(2-Aminoethoxy)methyl]-4-(2,5-difluorophenyl)-N,N-dimethyl-2-phenyl-2,5-dihydro-1H-pyrrole-1-carboxamide (2-3)

To 50 mg (0.12 mmol) of 2-2 in 3 mL of CH$_2$Cl$_2$, was added 35 μL (0.25 mmol) of triethylamine and 15 μL (0.19 mmol) of mesyl chloride. After 2 h, the reaction was quenched with saturated aqueous NaHCO$_3$, extracted twice with CH$_2$Cl$_2$, washed with water, dried over Na$_2$SO$_4$, and concentrated. The residue was dissolved in 2 mL of DMF, 16 mg (0.25 mmol) of NaN$_3$ was added, and the reaction was heated at 65° C. for 4 h. The reaction was cooled, diluted with EtOAc and washed five times with water, dried over Na$_2$SO$_4$ and concentrated. The residue was dissolved in 5 mL of THF, 40 mg (0.15 mmol) of triphenylphosphine was added and the resultant solution was stirred 24 h at room temperature. Water (1 mL) was then added and the mixture was heated at 65° C. for 1 h. The reaction was cooled, diluted with brine and EtOAc, separated, dried over Na$_2$SO$_4$, concentrated, and then purified by silica gel chromatography with CH$_2$Cl$_2$/MeOH/TEA to provide a colorless oil. The residue was dissolved in EtOAc and HCl gas was bubbled through the solution. The solution was concentrated, and then triturated with Et$_2$O to provide the HCl salt of 2-3 as a white solid. Data for 2-3.HCl: $^1$HNMR (500 MHz, d$_6$-DMSO) δ 7.9 (bs, 1H), 7.5-7.1 (m, 8H), 6.5 (s, 1H), 4.9 (d, 1H), 4.7 (d, 1H), 4.45 (d, 1H), 4.35 (d, 1H), 3.75 (m, 1H), 3.65 (m, 1H), 3.0 (bs, 2H), 2.8 (s, 6H) ppm. HRMS (ES) calc'd for C$_{22}$H$_{25}$F$_2$N$_3$O$_2$: 402.1998. Found: 402.1990.

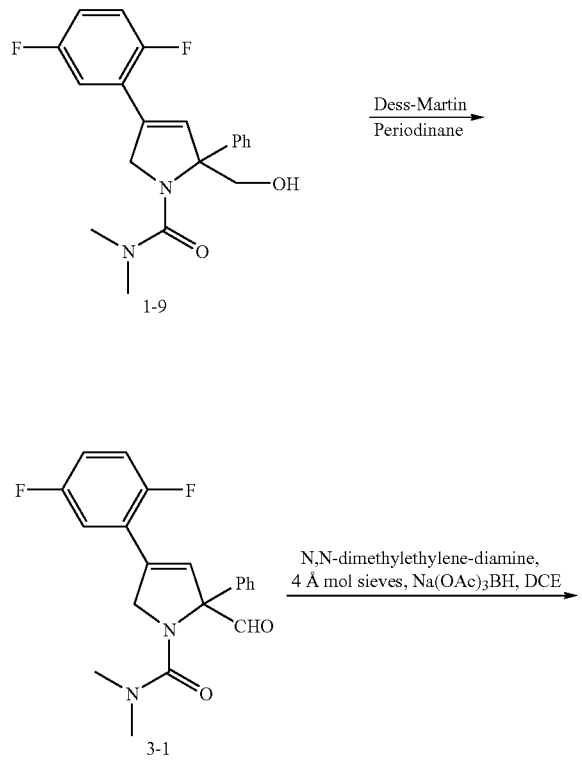

SCHEME 3

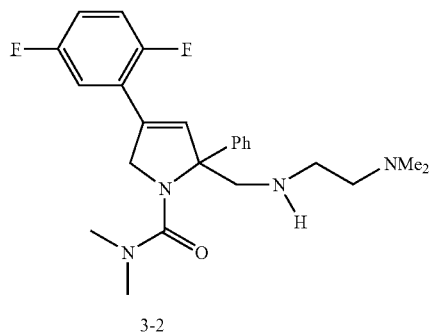

Step 1: 4-(2,5-Difluorophenyl)-2-formyl-N,N-dimethyl-2-phenyl-2,5-dihydro-1H-pyrrole-1-carboxamide (3-1)

To 50 mg (0.14 mmol) of 1-9 in 1 mL of CH$_2$Cl$_2$ was added 71 mg (0.17 mmol) of Dess-Martin Periodinane (Lancaster Synthesis) and the mixture was left to stir for 15 min at room temperature. The reaction was diluted with 10 mL of CH$_2$Cl$_2$, quenched with 5 mL of 5% aqueous NaHSO$_3$ and 10 mL of saturated aqueous NaHCO$_3$ and the biphasic mixture was stirred for 30 min. The layers were separated, the organic was washed with NaHCO$_3$ and water, dried over Na$_2$SO$_4$, and concentrated to provide 3-1 as a white solid. Data for 3-1: $^1$HNMR (500 MHz, CDCl$_3$) δ 9.6 (s, 1H), 7.4-7.2 (m, 5H), 7.1-6.9 (m, 3H), 6.2 (s, 1H), 4.9 (d, 1H), 4.8 (d, 1H), 3.0 (s, 6H) ppm.

Step 2: 4-(2,5-Difluorophenyl)-2-({[2-(dimethylamino)ethyl]amino}methyl)-N,N-dimethyl-2-phenyl-2,5-dihydro-1H-pyrrole-1-carboxamide (3-2)

To 20 mg (0.06 mmol) of 3-1 in 2 mL of 1,2-dichloroethane was added a spoonful of activated 4 Å molecular sieves and 20 μL (0.17 mmol) of N,N-dimethylethylene diamine. After stirring for 2 h, 59 mg (0.28 mmol) of Na(OAc)$_3$BH was added and the mixture was stirred overnight. The reaction was quenched with a saturated NH$_4$Cl solution, diluted with EtOAc and saturated NaHCO$_3$, separated, extracted twice with EtOAc, washed with brine, dried over Na$_2$SO$_4$, concentrated, and the residue purified by RP HPLC with CH$_3$CN/H$_2$O+0.1% TFA. The fractions were evaporated and then lyophilized to provide the bis-TFA salt of 3-2 as a white solid. Data for 3-2.2TFA: $^1$HNMR (500 MHz, d$_6$-DMSO) δ 7.5-7.1 (m, 8H), 6.5 (s, 1H), 4.95 (d, 1H), 4.8 (d, 1H), 4.4 (m, 1H), 3.8 (m, 1H), 2.9 (s, 6H), 2.85 (s, 6H) ppm (a broad peak from 3.7-3.3 seems to obscure some peaks). HRMS (ES) calc'd for C$_{24}$H$_{30}$F$_2$N$_4$O: 429.2461. Found: 429.2461.

SCHEME 4

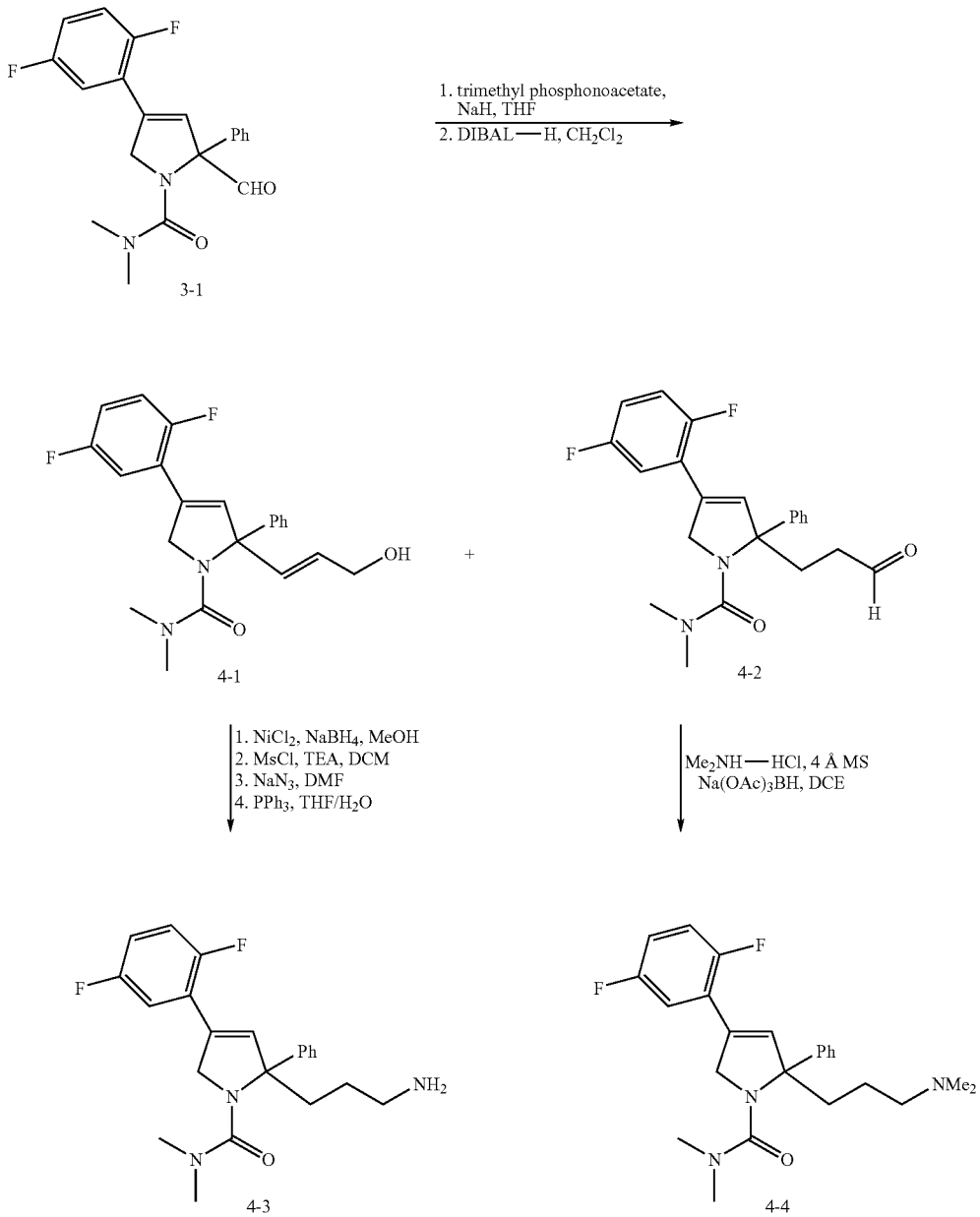

Step 1: 3-{4-(2,5-Difluorophenyl)-1-[(dimethylamino)carbonyl]-2-phenyl-2,5-dihydro-1H-pyrrol-2-yl}prop-2-en-1-aminium (4-1) and 4-(2,5-difluorophenyl)-N,N-dimethyl-2-(3-oxopropyl)-2-phenyl-2,5-dihydro-1H-pyrrole-1-carboxamide (4-2)

To 200 mg (0.56 mmol) of 3-1 in 10 mL of THF was added 175 μL (1.1 mmol) of trimethyl phosphonoacetate and 34 mg of NaH (0.84 mmol of a 60% suspension in oil), and the mixture was stirred for 30 min at 0° C. The reaction was quenched with a saturated NH$_4$Cl solution, diluted with EtOAc, separated, extracted twice with EtOAc, washed with brine, dried over Na$_2$SO$_4$, and concentrated. The residue was dissolved in 10 mL of CH$_2$Cl$_2$, cooled to −78° C. and 2 mL (2 mmol) of DIBAL-H (1M in CH$_2$Cl$_2$) was added and the solution was stirred for 30 min before being quenched with 1 mL of acetone. The cooling bath was removed and 20 mL of a 0.5 M tartaric acid solution was added and the biphasic mixture was stirred for 1 h. The layers were separated, the organic layer was washed with water, dried over Na$_2$SO$_4$, concentrated and purified by silica gel chromatography with EtOAc/hexanes to provide 4-1 as a white solid and 4-2 as a colorless oil. Data for 4-1: $^1$HNMR (500 MHz, CDCl$_3$) δ 7.4-7.2 (m, 5H), 7.1-6.9 (m, 3H), 6.3 (s, 1H), 5.9-5.8 (m, 2H), 4.85 (m, 1H), 4.75 (m, 1H), 4.3 (m, 2H), 2.8 (s, 6H) ppm. Data for 4-2: $^1$HNMR (500 MHz, CDCl$_3$) δ 9.8 (s, 1H), 7.4-7.2 (m, 5H), 7.1-6.9 (m, 3H), 6.1 (s, 1H), 4.85 (d, 1H), 4.65 (d, 1H), 3.4 (m, 1H), 2.8 (s, 6H), 2.6-2.4 (m, 3H) ppm.

Step 2: 2-(3-Hydroxypropyl)-4-(2,5-difluorophenyl)-N,N-dimethyl-2-phenyl-2,5-dihydro-1H-pyrrole-1-carboxamide (4-1a)

To 80 mg (0.20 mmol) of 4-1 in 4 mL of MeOH at 0° C. added 27 mg (0.20 mmol) of NiCl$_2$ and 80 mg (2 mmol) NaBH$_4$. After 15 min, the reaction was quenched with a saturated NH$_4$Cl solution, extracted with three times with EtOAc, washed with brine, dried over Na$_2$SO$_4$, concentrated and purified by silica gel chromatography with EtOAc/hexanes to provide the title compound 4-1a as a white solid. Data for 4-1a: $^1$HNMR (500 MHz, CDCl$_3$) δ 7.4-7.2 (m, 5H), 7.1-6.8 (m, 3H), 6.2 (s, 1H), 4.85 (d, 1H), 4.7 (d, 1H), 3.8-3.6 (m, 2H), 3.15-3.05 (m, 1H), 2.8 (s, 6H), 2.2-2.1 (m, 1H), 1.8-1.5 (m, 2H) ppm. HRMS (ES) calc'd for C$_{22}$H$_{24}$F$_2$N$_2$O$_2$: 387.1879. Found: 387.1877.

Step 3: 2-(3-Aminopropyl)-4-(2,5-difluorophenyl)-N,N-dimethyl-2-phenyl-2,5-dihydro-1H-pyrrole-1-carboxamide (4-3)

Compound 4-1a was dissolved in 5 mL CH$_2$Cl$_2$, and 55 μL of triethylamine and 15 μL of MsCl were added. After 2 h at room temperature, the reaction was quenched with saturated NaHCO$_3$, extracted twice with CH$_2$Cl$_2$, dried over Na$_2$SO$_4$, and concentrated. The residue was dissolved in 2 mL of DMF, 20 mg of NaN$_3$ was added, and the reaction was heated at 65° C. for 4 h. The reaction was cooled, diluted with EtOAc and washed five times with water, dried over Na$_2$SO$_4$ and concentrated. The residue was dissolved in 4 mL of THF, 30 mg of triphenylphosphine was added and the resultant mixture was stirred for 24 h at room temperature. Water (1 mL) was added and the mixture was heated at 65° C. for 1 h. The reaction was cooled, diluted with brine and EtOAc, separated, dried over Na$_2$SO$_4$, concentrated, and then purified by silica gel chromatography with CH$_2$Cl$_2$/MeOH/TEA to provide a colorless oil. The residue was dissolved in EtOAc and HCl gas was bubbled through the solution. The volatiles were removed by rotary evaporation, and the residue was triturated with Et$_2$O to provide the HCl salt of 4-3 as a white solid. Data for 4-3.HCl: $^1$HNMR (500 MHz, d$_6$-DMSO) δ 7.8 (bs, 1H), 7.5-7.1 (m, 8H), 6.2 (s, 1H), 5.0 (d, 1H), 4.85 (d, 1H), 2.85 (m, 3H), 2.75 (s, 6H), 2.2 (m, 1H), 1.5 (m, 2H) ppm. HRMS (ES) calc'd for C$_{22}$H$_{25}$F$_2$N$_3$O: 386.2039. Found: 386.2044.

Step 4: 4-(2,5-Difluorophenyl)-2-[3-(dimethylamino)propyl]-N,N-dimethyl-2-phenyl-2,5-dihydro-1H-pyrrole-1-carboxamide (4-4)

To 31 mg (0.08 mmol) of 4-2 in 2 mL of 1,2-dichloroethane was added a spoonful of activated 4 Å molecular sieves, 35 μL (0.25 mmol) of triethylamine and 13 mg (0.16 mmol) of dimethylamine hydrochloride. After stirring for 2 h, 59 mg (0.28 mmol) of Na(OAc)$_3$BH was added and the mixture was stirred overnight. The reaction was quenched with a saturated NH$_4$Cl solution, diluted with EtOAc and saturated NaHCO$_3$, separated, extracted twice with EtOAc, washed with brine, dried over Na$_2$SO$_4$, concentrated, and the residue purified by RP HPLC with CH$_3$CN/H$_2$O+0.1% TFA. The fractions were evaporated and then lyophilized to provide the TFA salt of 4-4 as a white solid. Data for 4-4-TFA: $^1$HNMR (500 MHz, d$_6$-DMSO) δ 9.2 (bs, 1H), 7.5-7.1 (m, 8H), 6.25 (s, 1H), 5.0 (d, 1H), 4.7 (d, 1H), 3.1 (m, 2H), 2.9-2.8 (m, 1H), 2.8 (s, 6H), 2.75 (s, 6H), 2.1 (m, 1H), 1.6 (m, 1H) ppm. HRMS (ES) calc'd for C$_{24}$H$_{29}$F$_2$N$_3$O: 414.2352. Found: 414.2347.

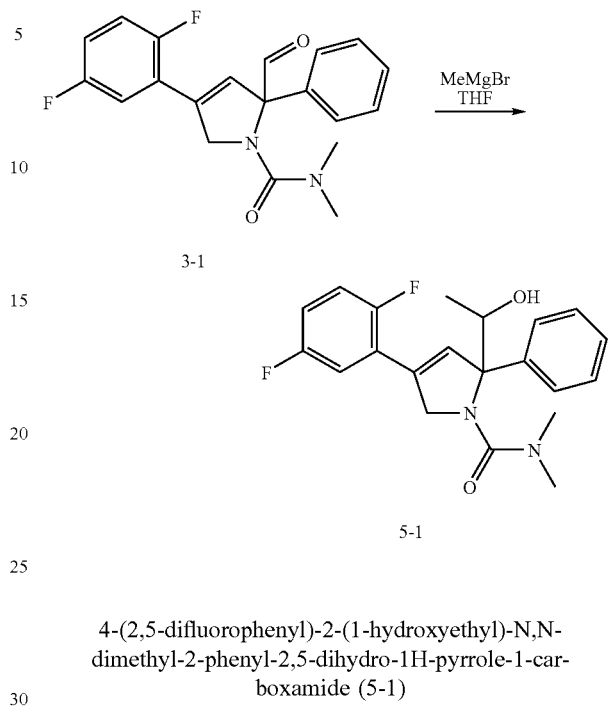

SCHEME 5

4-(2,5-difluorophenyl)-2-(1-hydroxyethyl)-N,N-dimethyl-2-phenyl-2,5-dihydro-1H-pyrrole-1-carboxamide (5-1)

To a suspension of 75 mg (0.21 mmol) of aldehyde 3-1 in THF at −78° C. was added 80 μL (0.25 mmol) of methyl magnesium bromide solution (3M in Et$_2$O). After stirring 1 h at that temperature, an additional 80 μL of the Grignard reagent was added and stirring was continued for 1 h more. The reaction was quenched with saturated NH$_4$Cl, partitioned between brine and EtOAc, the organic phase washed with brine, dried over MgSO$_4$, and concentrated. The residue was purified by column chromatography on silica gel with EtOAc/hexanes to provide 5-1 as a white solid. Data for 5-1: $^1$HNMR (500 MHz, CDCl$_3$) δ 7.6 (m, 2H), 7.4-7.2 (m, 3H), 7.1-6.9 (m, 3H), 6.5 (s, 1H), 5.05 (m, 1H), 4.8 (m, 1H), 4.6 (m, 1H), 4.35 (m, 1H), 2.8 (s, 6H), 1.4 (m, 3H) ppm. HRMS (ES) calc'd M+H for C$_{21}$H$_{22}$F$_2$N$_2$O$_2$: 373.1722. Found: 373.1713.

The following compounds were prepared by simple modifications of the above procedure.

| Compound No. | R | HRMS (calculated) | HRMS (found) |
|---|---|---|---|
| 5-2 | ethyl | 387.1879 | 387.1864 |
| 5-3 | isopropyl | 401.2035 | 401.2017 |
| 5-4 | cyclopropyl | 399.1879 | 399.1867 |

SCHEME 6

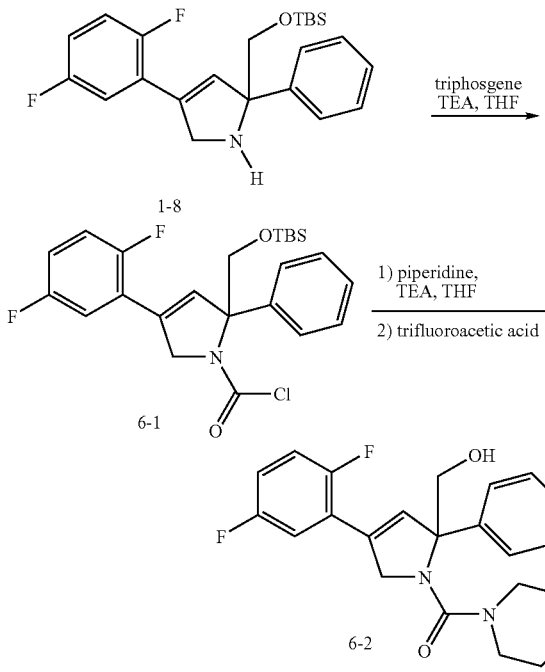

Step 1: 2-({[tert-butyl(dimethyl)silyl]oxy}methyl)-4-(2,5-difluorophenyl)-2-phenyl-2,5-dihydro-1H-pyrrole-1-carbonyl chloride (6-1)

To a solution of 3.7 g (12.5 mmol) of triphosgene in THF at 0° C. was added dropwise a mixture of 2.5 g (6.2 mmol) of amine 1-8 and 1.74 mL (12.5 mmol) of triethylamine in THF. The reaction was allowed to warm to room temperature overnight with stirring. The mixture was then dumped into water, placed in a separatory funnel, and extracted twice with EtOAc. The combined organic extracts were combined, washed with water, dried over $Na_2SO_4$ and concentrated to obtain 6-1 as a brown solid. Data for 6-1: HRMS (ES) calc'd M+H for $C_{24}H_{28}ClF_2NO_2Si$: 464.1619. Found: 464.1625.

Step 2: [4-(2,5-difluorophenyl)-2-phenyl-1-(piperidin-1-ylcarbonyl)-2,5-dihydro-1H-pyrrol-2-yl]methanol (6-2)

To 50 mg (0.11 mmol) of chloroformate 6-1 in THF was added 45 µL (0.32 mmol) of triethylamine, and 32 µL (0.32 mmol) of piperidine. After stirring overnight at room temperature, ~300 µL of trifluoroacetic acid was added and stirring was continued for 2 h. The mixture was partitioned between EtOAc and 10% $KHSO_4$, the layers were separated, the organic phase was washed with saturated $NaHCO_3$, brine, dried over $MgSO_4$, and concentrated by rotary evaporation. The residue was purified by column chromatography on silica gel with EtOAc/hexanes to provide 6-2 as a white solid. Data for 6-2: $^1$HNMR (500 MHz, $d_6$-DMSO) δ 7.4-7.2 (m, 8H), 6.4 (s, 1H), 5.1 (m, 1H), 4.8 (m, 1H), 4.7 (m, 1H), 4.35 (m, 1H), 4.1 (m, 1H), 3.2-3.0 (m, 4H), 1.8-1.6 (m, 6H) ppm. HRMS (ES) calc'd M+H for $C_{23}H_{24}F_2N_2O_2$: 399.1879. Found: 399.1860.

The following compounds were prepared by simple modifications of the above procedure.

| Compound No. | R | HRMS (calculated) | HRMS (found) |
|---|---|---|---|
| 6-3 | —N(morpholine) | 401.1671 | 401.1664 |
| 6-4 | —N(piperazine)—Me | 414.1988 | 414.1977 |
| 6-5 | —N(piperidine)-CH₂-N(Me)₂ | 456.2457 | 456.2445 |
| 6-6 | —(C(Me)₂)—N(azetidine) | 371.1566 | 371.1562 |
| 6-7 | —N(Me)-(tetrahydropyran-4-yl) | 429.1984 | 429.1989 |
| 6-8 | —N(Me)-CH₂-CH(Me)-CH₂-NH— | 430.2301 | 430.2304 |
| 6-9 | —N(Me)-(pyrrolidin-3-yl)-N-Me | 428.2144 | 428.2132 |
| 6-10 | —N(Me)-(pyrrolidin-3-yl)-N-CH₂Ph | 504.2457 | 504.2475 |
| 6-11 | —N(Me)-(pyrrolidin-3-yl)-NH | 414.1988 | 414.1977 |

-continued

[Structure with R group]

| Compound No. | R | HRMS (calculated) | HRMS (found) |
|---|---|---|---|
| 6-12 | [cyclopropyl-N-piperidinyl-N-Me group] | 468.2457 | 468.2437 |
| 6-13 | [NH-piperidinyl-N-Me group] | 428.2144 | 428.2135 |
| 6-14 | [N(Me)-benzyl group] | 435.1879 | 435.1849 |

SCHEME 7

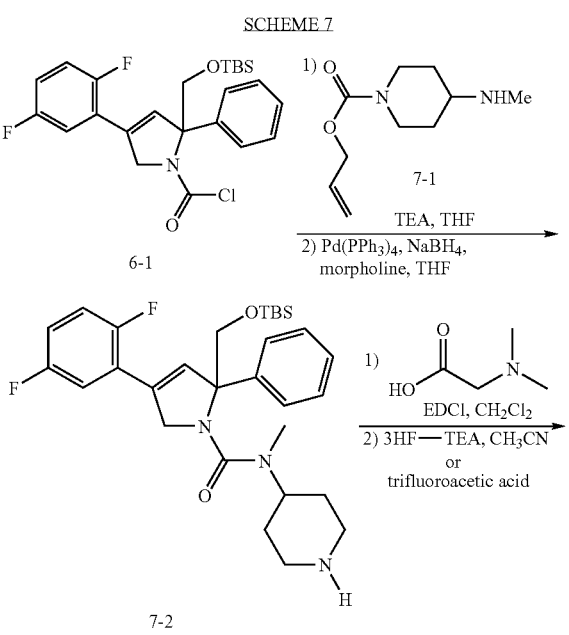

-continued

[Structure 7-3]

Step 1: 2-({[tert-butyl(dimethyl)silyl]oxy}methyl)-4-(2,5-difluorophenyl)-N-methyl-2-phenyl-N-piperidin-4-yl-2,5-dihydro-1H-pyrrole-1-carboxamide (7-2)

To 1.25 g (2.7 mmol) of chloroformate 6-1 in THF was added 1.2 mL (8.1 mmol) of triethylamine, 590 mg (3.0 mmol) of amine 7-1 (Supplier: High Force Research Ltd.), and a catalytic amount of DMAP. After stirring overnight at room temperature, the mixture was partitioned between EtOAc and saturated NaHCO$_3$, the layers were separated, the organic phase was washed with water, 10% KHSO$_4$, brine, dried over MgSO$_4$, and concentrated by rotary evaporation. The residue was purified by column chromatography on silica gel with EtOAc/hexanes to provide a colorless oil. This material (1.32 g, 2.1 mmol) was dissolved in anhydrous THF and N$_2$ was bubbled through the solution for 5 minutes. To this mixture was then added 320 mg (8.4 mmol) of NaBH$_4$, 835 µL (8.4 mmol) of piperidine, and 122 mg (0.10 mmol) of tetrakistriphenylphosphine palladium(0). After stirring for 2 h at room temperature, the reaction was quenched with saturated NaHCO$_3$, poured into EtOAc and the layers were separated. The organic phase was washed with water, brine, dried over MgSO$_4$, and concentrated by rotary evaporation. The residue was purified by column chromatography on silica gel with EtOAc/hexanes to provide 7-2 as an off-white solid. Data for 7-2: $^1$HNMR (500 MHz, CDCl$_3$) δ 7.4-7.2 (m, 5H), 7.1-6.9 (m, 3H), 6.35 (s, 1H), 4.8 (m, 1H), 4.7-4.6 (m, 2H), 4.45 (m, 1H), 3.6 (m, 1H), 3.1 (m, 2H) 2.75 (s, 3H), 2.7-2.6 (m, 2H), 2.05 (bs, 1H), 1.8-1.6 (m, 4H), 0.8 (s, 9H), 0.04 (s, 3H), 0.02 (s, 3H) ppm. HRMS (ES) calc'd M+H for C$_{30}$H$_{41}$F$_2$N$_3$O$_2$Si: 542.3009. Found: 542.2999.

Step 2: 4-(2,5-difluorophenyl)-N-[1-(N,N-dimethylglycyl)piperidin-4-yl]-2-(hydroxymethyl)-N-methyl-2-phenyl-2,5-dihydro-1H-pyrrole-1-carboxamide (7-3)

To 30 mg (0.055 mmol) of amine 7-2 in CH$_2$Cl$_2$ was added 10 mg (0.097 mmol) of N,N-dimethylglycine and 15 mg (0.078 mmol) of EDCI. After stirring overnight at room temperature, the mixture was partitioned between CH$_2$Cl$_2$ and saturated NaHCO$_3$, the layers were separated, the organic phase was washed with water, dried over Na$_2$SO$_4$, and concentrated by rotary evaporation. The residue was dissolved in dry CH$_3$CN and ~500 µL of 3HF-TEA was added and the mixture was stirred overnight at room temperature. The reaction was partitioned between EtOAc and saturated NaHCO$_3$, the layers were separated, the organic phase was washed with brine, dried over Na$_2$SO$_4$, and concentrated by rotary evaporation. The residue was purified by reverse phase HPLC to provide 7-3 as a white solid. Data for 7-3: HRMS (ES) calc'd M+H for C$_{28}$H$_{34}$F$_2$N$_4$O$_3$: 513.2672. Found: 513.2673.

SCHEME 8

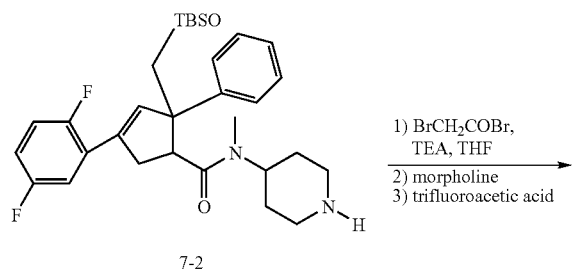

4-(2,5-difluorophenyl)-2-(hydroxymethyl)-N-methyl-N-[1-(morpholin-4-ylacetyl)piperidin-4-yl]-2-phenyl-2,5-dihydro-1H-pyrrole-1-carboxamide (8-1)

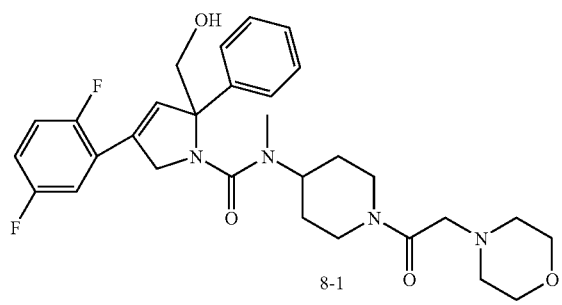

To 394 mg (0.73 mmol) of amine 7-2 in THF at 0° C. was added 190 μL (1.1 mmol) of N,N-diisopropylethylamine and 70 μL (0.80 mmol) of bromoacetyl bromide. After warming to room temperature, the reaction was judged complete after 30 min. The mixture was partitioned between EtOAc and water, the layers were separated, the organic phase was washed with water, brine, dried over MgSO$_4$, and concentrated by rotary evaporation to provide the acetyl bromide as a tan solid. To 75 mg (0.11 mmol) of this material in DMF was added 100 μL (1.1 mmol) of morpholine and the mixture was heated in a microwave reactor at 150° C. for 10 min. After cooling to room temperature, 500 μL trifluoroacetic acid was added and stirring was continued for 30 min. The mixture was partitioned between EtOAc and saturated NaHCO$_3$, the layers were separated, the organic phase was washed with water, brine, dried over MgSO$_4$, and concentrated by rotary evaporation to provide 8-1 as a cloudy film. Data for 8-1: $^1$HNMR (500 MHz, CDCl$_3$) δ 7.4-7.2 (m, 5H), 7.1-6.9 (m, 3H), 6.3 (s, 1H), 5.3-5.2 (m, 1H), 4.85 (m, 1H), 4.7 (m, 1H), 4.6 (m, 1H), 4.45 (m, 1H), 4.15 (m, 1H), 4.0-3.9 (m, 2H), 3.7 (m, 4H), 3.3 (m, 1H), 3.2-3.0 (m, 2H), 2.9 (d, 3H), 2.7-2.5 (m, 5H), 1.9 (m, 1H), 1.8-1.6 (m, 3H) ppm. HRMS (BS) calc'd M+H for C$_{30}$H$_{36}$F$_2$N$_4$O$_4$: 555.2778. Found: 555.2733.

The following compounds were prepared by simple modifications of the above procedure.

| Compound No. | R | HRMS (calculated) | HRMS (found) |
|---|---|---|---|
| 8-2 | H | 428.2144 | 428.2114 |
| 8-3 | ⚡C(O)CH$_2$NH$_2$ | 485.2359 | 485.2324 |
| | (isolated as the TFA salt) | | |
| 8-4 | ⚡C(O)CH$_2$-piperidinyl | 553.2985 | 553.2964 |
| 8-5 | ⚡C(O)CH$_2$-azetidinyl | 525.2672 | 525.2658 |
| 8-6 | ⚡C(O)CH(Me)-morpholinyl | 569.2934 | 569.2932 |
| 8-7 | ⚡C(O)CH$_2$NHEt | 513.2672 | 513.2649 |

SCHEME 9

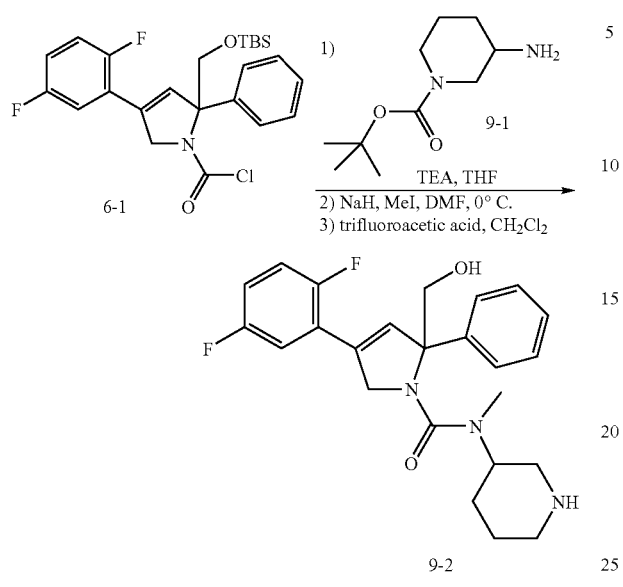

4-(2,5-difluorophenyl)-2-(hydroxymethyl)-N-methyl-2-phenyl-N-piperidin-3-yl-2,5-dihydro-1H-pyrrole-1-carboxamide (9-2)

To 100 mg (0.22 mmol) of chloroformate 6-1 in THF was added 130 mg (0.65 mmol) of (+/−)-3-amino-1-N-Boc-piperidine (9-1) and 90 µL (0.65 mmol) of triethylamine. After stirring overnight at room temperature, the mixture was partitioned between EtOAc and saturated NaHCO$_3$, the layers were separated, the organic phase was washed with water, brine, dried over MgSO$_4$, and concentrated by rotary evaporation. The residue was purified by column chromatography on silica gel with EtOAc/hexanes to provide both diastereomers in pure form. To 35 mg (0.057 mmol) of the first eluting diastereomer in DMF at 0° C. was added 18 µL (0.29 mmol) of MeI and 11 mg (0.29 mmol) of NaH (60% dispersion in oil). After stirring for 3 h at 0° C., the reaction was quenched with saturated NH$_4$Cl, poured into EtOAc, and the layers were separated. The organic phase was washed with brine, dried over MgSO$_4$, and concentrated by rotary evaporation. The residue was then dissolved in CH$_2$Cl$_2$ and 1 mL of trifluoroacetic acid was added. After stirring for 3 h at room temperature, the solvents were removed, the residue was partitioned between EtOAc and saturated NaHCO$_3$, the organic phase was washed with brine, dried over MgSO$_4$ and concentrated by rotary evaporation. The residue was then purified by silica gel chromatography with 20:1:1 EtOH/NH$_4$OH/H$_2$O in EtOAc to provide 9-2 as a white solid. Data for 9-2: $^1$HNMR (500 MHz, CDCl$_3$) δ 7.4-7.2 (m, 5H), 7.1-6.9 (m, 3H), 6.25 (s, 1H), 4.8 (m, 1H), 4.65 (m, 1H), 4.45 (m, 1H), 4.0 (m, 1H), 3.8 (m, 1H), 3.1 (m, 2H) 2.9 (s, 3H), 2.6 (m, 2H), 2.1-0.9 (m, 6H) ppm. HRMS (ES) calc'd M+H for C$_{24}$H$_{27}$F$_2$N$_3$O$_2$: 428.2144. Found: 428.2132.

The following compounds were prepared by simple modifications of the above procedure.

| Compound No. | R | HRMS (calculated) | HRMS (found) |
|---|---|---|---|
| 9-3 | —CH$_3$ | 442.2301 | 442.2302 |
| 9-4 | ethyl | 456.2457 | 456.2449 |
| 9-5 | isopropyl | 470.2614 | 470.2606 |
| 9-6 | —C(O)CH$_2$N(CH$_3$)$_2$ | 513.2672 | 513.2666 |

SCHEME 10

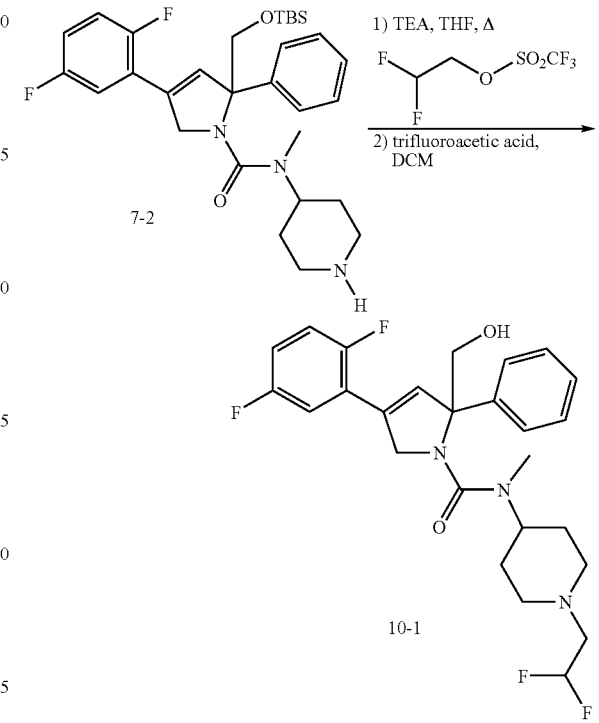

N-[1-(2,2-difluoroethyl)piperidin-4-yl]-4-(2,5-difluorophenyl)-2-(hydroxymethyl)-N-methyl-2-phenyl-2,5-dihydro-1H-pyrrole-1-carboxamide (10-1)

To 87 mg (0.16 mmol) of amine 7-2 in THF in a sealed tube was added 41 mg (0.19 mmol) of 2,2-difluoroethyl trifluoromethane sulfonate and 67 µL (0.48 mmol) of triethylamine. After stirring 2.5 h at 70° C., the mixture was partitioned between EtOAc and saturated NaHCO$_3$, the layers were separated, the organic phase was washed with brine, dried over MgSO$_4$, and concentrated by rotary evaporation. The residue was dissolved in 5 mL CH$_2$Cl$_2$ and 1 mL of trifluroacetic acid was added. After stirring for 30 min at room temperature, the solvents were removed by rotary evaporation, the residue was partitioned between EtOAc and saturated NaHCO$_3$, the layers were separated, the organic phase was washed with brine, dried over MgSO$_4$, and concentrated by rotary evaporation. The residue was purified by column chromatography on silica gel with MeOH/CHCl$_3$ to provide 10-1 as a white solid. Data for 10-1: $^1$HNMR (500 MHz, CDCl$_3$) δ 7.7-7.3 (m, 5H), 7.1-6.9 (m, 3H), 6.3 (s, 1H), 5.8 (m, 1H), 5.4 (m, 1H), 4.8 (m, 1H), 4.6 (m, 1H), 4.4 (m, 1H), 4.0 (m, 1H), 3.7 (m, 1H), 3.0 (m, 2H), 2.9 (s, 3H), 2.75 (m, 2H), 2.3 (m, 2H), 1.9 (m, 2H), 1.6 (m, 1H) ppm. HRMS (ES) calc'd M+H for C$_{26}$H$_{29}$F$_4$N$_3$O$_2$: 492.2269. Found: 492.2250.

partitioned between EtOAc and saturated NaHCO$_3$, the layers were separated, the organic phase was washed with water, dried over MgSO$_4$, and concentrated by rotary evaporation. The residue was dissolved in dry EtOAc, saturated with HCl$_{(g)}$ and stirred for 1 h. The reaction was partitioned between EtOAc and saturated NaHCO$_3$, the layers were separated, the organic phase was washed with water, dried over MgSO$_4$, and concentrated by rotary evaporation. The residue was purified by reverse phase HPLC, but was not of sufficient purity, so it was then purified by column chromatography on silica gel with 20:1:1 EtOH/NH$_4$OH/H$_2$O in EtOAc to provide 11-1 as a white solid. Data 11-1: $^1$HNMR (500 MHz, CDCl$_3$) δ 7.4-7.2 (m, 5H), 7.1-6.9 (m, 3H), 6.3 (s, 1H), 5.4 (m, 1H), 4.8 (m, 1H), 4.6 (m, 1H), 4.4 (m, 1H), 4.0 (m, 1H), 3.75 (m, 1H), 3.6 (m, 2H), 3.0 (m, 2H), 2.9 (s, 3H), 2.5 (m, 2H), 2.2 (m, 2H), 1.8 (m, 3H), 1.7 (m, 1H) ppm. HRMS (ES) calc'd M+H for C$_{26}$H$_{31}$F$_2$N$_3$O$_3$: 472.2406. Found: 472.2386.

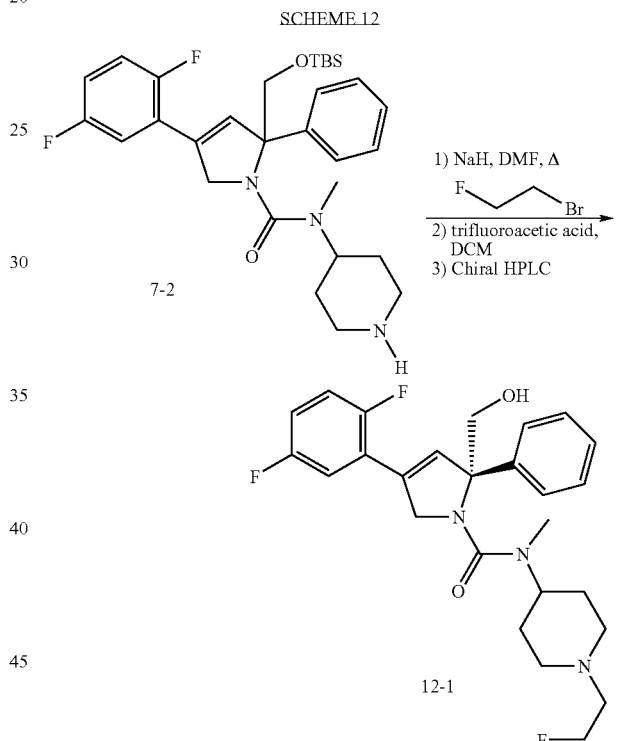

(2S)-4-(2,5-difluorophenyl)-N-[1-(2-fluoroethyl)piperidin-4-yl]-2-(hydroxymethyl)-N-methyl-2-phenyl-2,5-dihydro-1H-pyrrole-1-carboxamide (12-1)

To 60 mg (0.11 mmol) of amine 7-2 in DMF at 0° C. was added 13 µL (0.17 mmol) of 1-bromo-2-fluoroethane and 8 mg (0.17 mmol) of NaH (60% dispersion in oil). After warming to room temperature, another portion of NaH and the bromide were added, and the reaction was allowed to stir overnight. LC-MS indicated still 25% unreacted 7-2, so the mixture was heated to 60° C. for several hours. After cooling to room temperature, ~500 µL of trifluoroacetic acid was added and the mixture was stirred for 1 h. The reaction was partitioned between EtOAc and 15% aqueous Na$_2$CO$_3$, the layers were separated, the organic phase was washed with saturated NaHCO$_3$, water, brine, dried over MgSO$_4$, and concentrated by rotary evaporation. The residue was purified

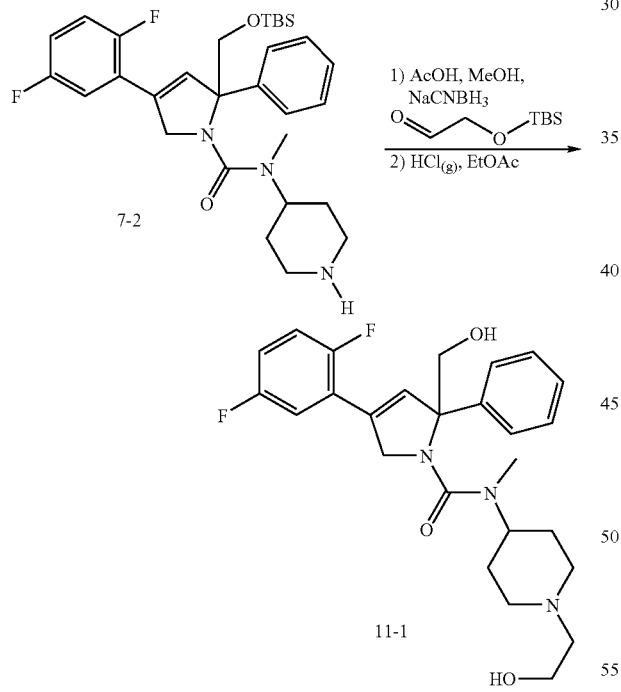

4-(2,5-difluorophenyl)-N-[1-(2-hydroxyethyl)piperidin-4-yl]-2-(hydroxymethyl)-N-methyl-2-phenyl-2,5-dihydro-1H-pyrrole-1-carboxamide (11-1)

To 150 mg (0.28 mmol) of amine 7-2 in MeOH was added 145 mg (0.83 mmol) of (t-butyldimethylsilyloxy) acetaldehyde and several drops of HOAc. After stirring for 1 h, 35 mg (0.55 mmol) of NaCNBH$_3$ was added and the reaction was stirred overnight in a sealed flask. The mixture was by column chromatography on silica gel with 20:1:1 EtOH/NH$_4$OH/H$_2$O in EtOAc to provide 12-1 as a white solid. Data for 12-1: $^1$HNMR (500 MHz, CDCl$_3$) δ 7.4-7.2 (m, 5H), 7.1-6.9 (m, 3H), 6.3 (s, 1H), 5.4 (m, 1H), 4.8 (m, 1H), 4.6-4.4 (m, 4H), 4.0 (m, 1H), 3.75 (m, 1H), 3.1 (m, 2H), 2.9 (s, 3H), 2.75-2.65 (m, 2H), 2.2 (m, 2H), 1.9 (m, 3H), 1.7 (m, 1H) ppm. HRMS (ES) calc'd M+H for C$_{26}$H$_{30}$F$_3$N$_3$O$_2$: 474.2363. Found: 474.2355. Resolution of the enantiomers was carried out chromatographically using a Chiralpak AD© 10×50 cm column with 30% isopropanol in hexanes (with 0.1% diethylamine) at 150 ml/min. Analytical HPLC analysis of the eluent on a 4×250 mm Chiralpak AD® column with 30% isopropanol in hexanes (with 0.1% diethylamine) at 1 ml/min indicated that inactive enantiomer has R$_f$=6.3 min and the active enantiomer has R$_f$=7.5 min.

SCHEME 13

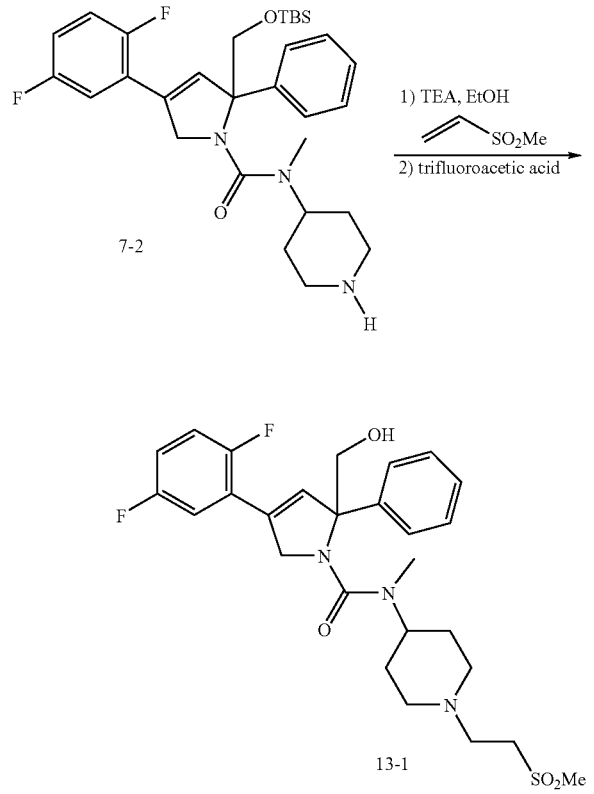

4-(2,5-difluorophenyl)-2-(hydroxymethyl)-N-methyl-N-{1-[(methylsulfonyl)methyl]piperidin-4-yl}-2-phenyl-2,5-dihydro-1H-pyrrole-1-carboxamide (13-1)

To 40 mg (0.07 mmol) of amine 7-2 in EtOH was added 15 μL (0.11 mmol) of triethylamine and 10 μL (0.11 mmol) of methyl vinyl sulfone. After stirring for 60 min, ~500 μL of trifluoroacetic acid was added and the mixture was stirred for 1 h. The reaction was partitioned between EtOAc and 15% aqueous Na$_2$CO$_3$, the layers were separated, the organic phase was washed with saturated NaHCO$_3$, water, brine, dried over MgSO$_4$, and concentrated by rotary evaporation. The residue was purified by column chromatography on silica gel with 20:1:1 EtOH/NH$_4$OH/H$_2$O in EtOAc to provide 13-1 as a white solid. Data for 13-1: $^1$HNMR (500 MHz, CDCl$_3$) δ 7.4-7.2 (m, 5H), 7.1-6.9 (m, 3H), 6.3 (s, 1H), 5.3 (m, 1H), 4.8 (m, 1H), 4.6 (m, 1H), 4.4 (m, 1H), 4.0 (m, 1H), 3.75 (m, 1H), 3.15 (m, 2H), 3.05 (s, 3H), 3.0 (m, 2H), 2.9 (s, 3H), 2.85 (m, 2H), 2.2 (m, 2H), 1.9-1.7 (m, 4H) ppm. HRMS (ES) calc'd M+H for C$_{27}$H$_{33}$F$_2$N$_3$O$_4$S$_1$: 534.2233. Found: 534.2218.

SCHEME 14

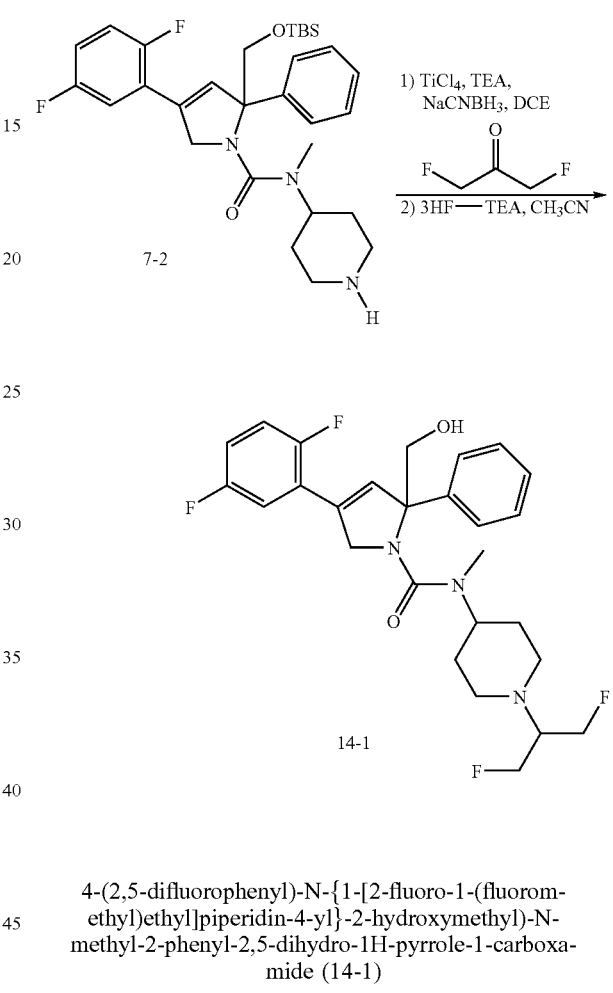

4-(2,5-difluorophenyl)-N-{1-[2-fluoro-1-(fluoromethyl)ethyl]piperidin-4-yl}-2-hydroxymethyl)-N-methyl-2-phenyl-2,5-dihydro-1H-pyrrole-1-carboxamide (14-1)

To 50 mg (0.092 mmol) of amine 7-2 in dry 1,2-dichloroethane was added 80 μL (0.55 mmol) of triethylamine, 1.5 mL (~0.37 mmol) of 1,3-difluoroacetone in benzene (prepared according to F. A. Davis, et. al. *Synthesis* 1994, 701-702) and 90 μL (0.09 mmol) of a 1M solution of TiCl$_4$ in CH$_2$Cl$_2$. After stirring for 72 h, 36 mg (0.55 mmol) of NaCNBH$_3$ in MeOH was added and the mixture was stirred for an additional 4 h. The reaction was partitioned between EtOAc and saturated NH$_4$Cl, the layers were separated, the organic phase was washed with brine, dried over Na$_2$SO$_4$, and concentrated by rotary evaporation. The residue was then dissolved in dry CH$_3$CN and ~500 μL of 3HF-TEA was added and the reaction was stirred at room temperature overnight. The mixture was partitioned between EtOAc and saturated NaHCO$_3$, the layers were separated, and the aqueous phase was extracted again with EtOAc. The organic phases were combined, washed with saturated NaHCO$_3$, brine, dried over Na$_2$SO$_4$, and concentrated by rotary evaporation. The residue was purified by reverse phase HPLC to provide 14-1 as a white solid. Data for 14-1: HRMS (ES) calc'd M+H for $C_{27}H_{31}F_4N_3O_2$: 506.2425. Found: 506.2402.

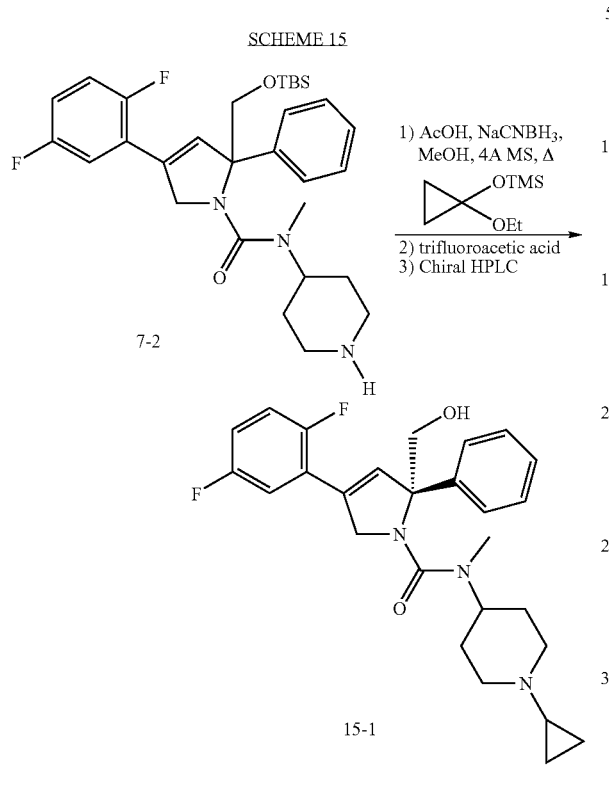

(2S)-N-(1-cyclopropylpiperidin-4-yl)-4-(2,5-difluorophenyl)-2-(hydroxymethyl)-N-methyl-2-phenyl-2,5-dihydro-1H-pyrrole-1-carboxamide (15-1)

To 30 mg (0.055 mmol) of amine 7-2 in MeOH was added 30 µL (0.55 mmol) of HOAc, 33 µL (0.17 mmol) of (1-ethoxycyclopropoxy)trimethylsilane, 10 mg (0.17 mmol) of NaCNBH$_3$ and 100 mg of 4 Å molecular sieves. The mixture was then heated at 100° C. for 10 min in a microwave reactor. After cooling to room temperature, ~500 µL of trifluoroacetic acid was added and the mixture was stirred for 1 h. The reaction was partitioned between EtOAc and saturated NaHCO$_3$, the layers were separated, the organic phase was washed with water, brine, dried over MgSO$_4$, and concentrated by rotary evaporation. The residue was purified by column chromatography on silica gel with 20:1:1 EtOH/NH$_4$OH/H$_2$O in EtOAc to provide 15-1 as a white solid. Data for 15-1: $^1$HNMR (500 MHz, CDCl$_3$) δ 7.4-7.2 (m, 5H), 7.1-6.9 (m, 3H), 6.3 (s, 1H), 5.45 (m, 1H), 4.8 (m, 1H), 4.6 (m, 1H), 4.4 (m, 1H), 4.0 (m, 1H), 3.75 (m, 1H), 3.15 (m, 2H), 2.9 (s, 3H), 2.3 (m, 2H), 1.9-1.6 (m, 5H), 0.5-0.4 (m, 4H) ppm. HRMS (ES) calc'd M+H for $C_{27}H_{31}F_2N_3O_2$: 468.2457. Found: 468.2438. Resolution of the enantiomers was carried out chromatographically using a Chiralpak AD© 10×50 cm column with 15% isopropanol in hexanes (with 0.1% diethylamine) at 150 mL/min. Analytical HPLC analysis of the eluent on a 4×250 mm Chiralpak AD® column with 15% isopropanol in hexanes (with 0.1% diethylamine) at 1 mL/min indicated that inactive enantiomer has R$_t$=7.05 min and the active enantiomer has R$_t$=8.17 min.

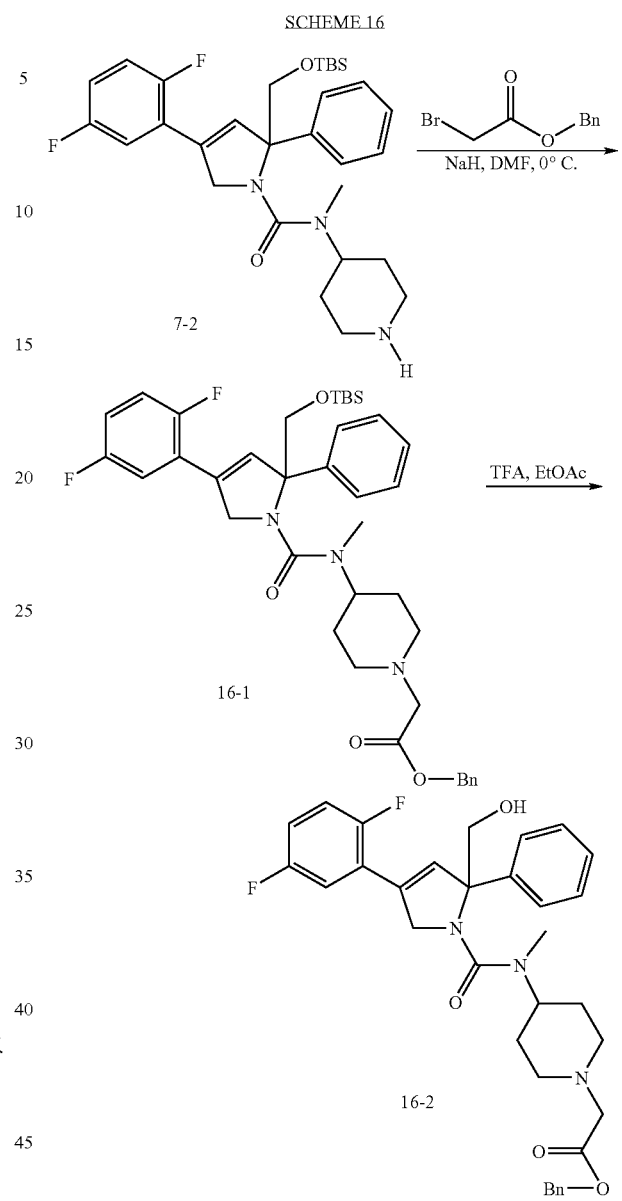

benzyl {4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetate (16-2)

To 500 mg (0.92 mmol) of amine 7-2 in DMF at 0° C. was added 292 µL (1.8 mmol) of benzyl 2-bromoacetate and 55 mg (1.4 mmol) of NaH (60% suspension in oil). The ice bath was removed after 15 min and stirring was continued for an additional 90 min. The reaction was partitioned between EtOAc and saturated NaHCO$_3$, the layers were separated, the organic phase was washed with water, brine, dried over MgSO$_4$, and concentrated by rotary evaporation. The residue was purified by column chromatography on silica gel with EtOAc/hexanes to provide amino ester 16-1. To a mixture of 16-1 in EtOAc was added ~500 µL of trifluoroacetic acid and the mixture was stirred at room temperature for 1 h. The reaction was partitioned between EtOAc and saturated NaHCO$_3$, the layers were separated, the organic phase was washed with saturated NaHCO₃, water, brine, dried over MgSO₄, and concentrated by rotary evaporation. The residue was purified by column chromatography on silica gel with 20:1:1 EtOH/NH₄OH/H₂O in EtOAc to provide 16-2 as a white solid. Data for 16-2: ¹HNMR (500 MHz, CDCl₃) δ 7.4-7.2 (m, 10H), 7.1-6.9 (m, 3H), 6.3 (s, 1H), 5.4 (m, 1H), 5.2 (s, 2H), 4.8 (m, 1H), 4.6 (m, 1H), 4.4 (m, 1H), 4.0 (m, 1H), 3.75 (m, 1H), 3.3 (m, 2H), 3.05 (m, 2H), 2.9 (s, 3H), 2.3 (m, 2H), 2.0-1.8 (m, 3H), 1.65 (m, 1H) ppm. HRMS (ES) calc'd M+H for C₃₃H₃₅F₂N₃O₄: 576.2669. Found: 576.2620.

SCHEME 17

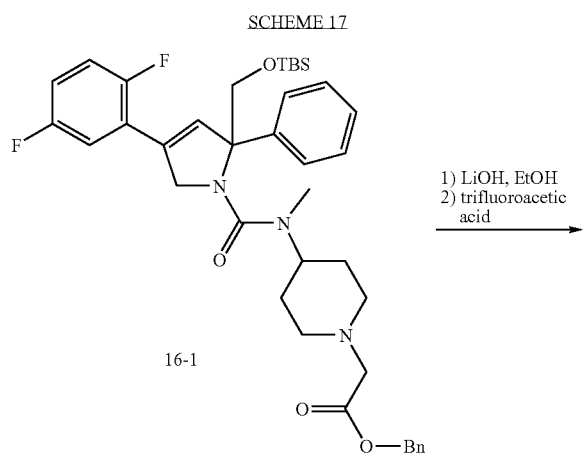

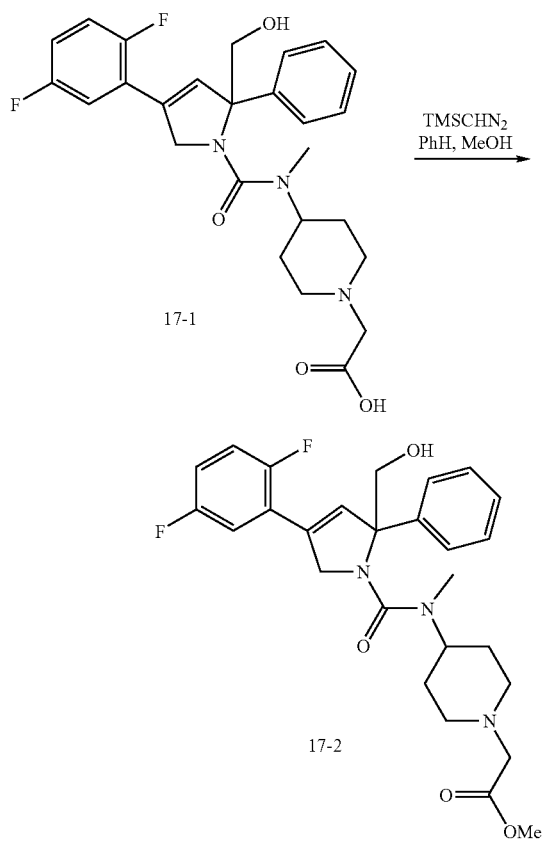

Step 1: {4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetic acid (17-1)

To 300 mg (0.44 mmol) of amino ester 16-1 in EtOH was added 1M LiOH. After stirring for 2 h at room temperature, the mixture was partitioned between EtOAc and 10% KHSO₄, the layers were separated, the organic phase was washed with brine, dried over MgSO₄, and concentrated by rotary evaporation. The residue was dissolved in 3-4 ml of CH₂Cl₂, 1 mL of trifluoroacetic acid was added and stirring was maintained for 30 min. The reaction was then partitioned between EtOAc and saturated NaHCO₃, the layers were separated, the aqueous phase neutralized to pH 7 with concentrated HCl, and extracted five times with 4:1 CHCl₃/iPrOH. After concentration by rotary evaporation, the residue was purified by column chromatography on silica gel with 20:1:1 EtOH/NH₄OH/H₂O in EtOAc to provide 17-1 as a white solid Data for 17-1: ¹HNMR (500 MHz, CD₃OD) δ 7.4-7.0 (m, 8H), 6.3 (s, 1H), 4.95 (m, 1H), 4.75 (m, 1H), 4.6 (m, 1H), 4.2 (m, 1H), 3.8 (m, 1H), 3.65 (m, 2H), 3.55 (s, 2H), 3.1 (m, 2H), 2.9 (s, 3H), 2.15 (m, 2H), 2.0 (m, 1H), 1.9 (m, 1H) ppm. HRMS (ES) calc'd M+H for C₂₆H₂₉F₂N₃O₄: 486.2199. Found: 486.2171.

Step 2: methyl {4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetate (17-2)

To 30 mg (0.06 mmol) of amino acid 17-1 in 1:1 PhH/MeOH was added 120 μL (0.24 mmol) of TMS-diazomethane. After stirring for 2 h, the reaction was concentrated by rotary evaporation and the residue was purified by column chromatography on silica gel with 20:1:1 EtOH/NH₄OH/H₂O in EtOAc to provide 17-2 as a colorless film. Data for 17-2: ¹HNMR (500 MHz, CDCl₃) δ 7.4-7.2 (m, 5H), 7.1-6.9 (m, 3H), 6.3 (s, 1H), 5.45 (m, 1H), 4.8 (m, 1H), 4.6 (m, 1H), 4.4 (m, 1H), 4.0 (m, 1H), 3.75 (m, 1H), 3.7 (s, 3H), 3.2 (m, 2H), 3.05 (m, 2H), 2.9 (s, 3H), 2.3 (m, 2H), 2.0-1.8 (m, 3H), 1.7 (m, 1H) ppm. HRMS (ES) calc'd M+H for C₂₇H₃₁F₂N₃O₄: 500.2356. Found: 500.2331.

The following compounds were prepared by simple modifications of the above procedures in Scheme 10-17.

| Compound No. | R | HRMS (calculated) | HRMS (found) |
|---|---|---|---|
| 17-3 | isobutyl | 470.2614 | 470.2614 |

-continued

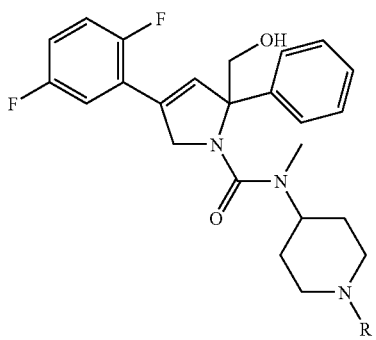

| Compound No. | R | HRMS (calculated) | HRMS (found) |
|---|---|---|---|
| 17-4 | ethyl | 456.2457 | 456.2449 |
| 17-5 | cyclopropylmethyl | 482.2614 | 482.2603 |
| 17-6 | CH2CH(CH3)-F | 488.2520 | 488.2517 |
| 17-7 | CH2CHF-CF (F) | 506.2425 | 506.2408 |
| 17-8 | CH2CH2CF3 | 524.2331 | 524.2310 |
| 17-9 | CH2-C6H4-X, X=C—H | 518.2614 | 518.2602 |
| 17-10 | CH2-C6H4-X, X=N | 519.2566 | 519.2552 |

SCHEME 18

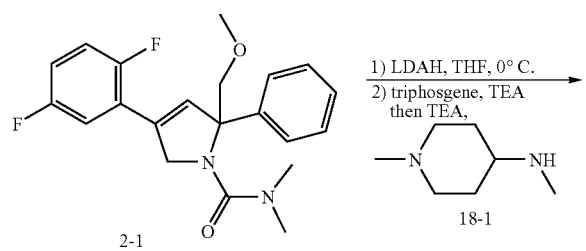

-continued

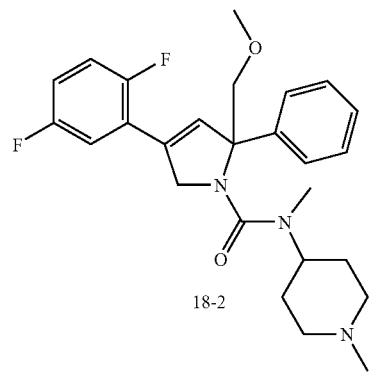

4-(2,5-difluorophenyl)-2-(methoxymethyl)-N-methyl-N-(1-methylpiperidin-4-yl)-2-phenyl-2,5-dihydro-1H-pyrrole-1-carboxamide (18-2)

To 200 mg (0.54 mmol) of urea 2-1 in THF at 0° C. was added 1.07 mL (1.07 mmol) of a lithium aluminum hydride solution (1M in THF). The cooling bath was removed after 5 min and stirring was continued for 1.5 h at room temperature. The reaction was carefully quenched with a saturated aqueous solution of Rochelle's salt and then partitioned between EtOAc and saturated NaHCO$_3$. The organic phase was washed with a 1:1 solution of saturated aqueous Rochelle's salt/saturated NaHCO$_3$, water, brine, dried over MgSO$_4$, and concentrated to provide the secondary amine as a pale yellow oil. To 75 mg (0.25 mmol) of this material in THF at 0° C. was added 70 μL (0.50 mmol) of triethylamine and 37 mg (0.13 mmol) of triphosgene. After stirring for 1 h, 110 μL (0.72 mmol) of diamine 18-1 was added and the reaction was heated to 50° C. for 12 h. After cooling to room temperature, the mixture was partitioned between EtOAc and saturated NaHCO$_3$, the layers were separated, the organic phase was washed with water, brine, dried over MgSO$_4$, and concentrated by rotary evaporation. The residue was purified by column chromatography on silica gel with 20:1:1 EtOH/NH$_4$OH/H$_2$O in EtOAc to provide 18-2 as a pale yellow waxy solid. Data for 18-2: $^1$HNMR (500 MHz, CDCl$_3$) δ 7.4-7.2 (m, 5H), 7.1-6.9 (m, 3H), 6.4 (s, 1H), 4.8-4.6 (m, 2H), 4.45 (m, 1H), 4.35 (m, 1H), 3.5 (m, 1H), 3.4 (s, 3H), 2.9 (m, 2H) 2.7 (s, 3H), 2.25 (s, 3H), 2.0 (m, 2H), 1.8-1.6 (m, 4H) ppm. HRMS (ES) calc'd M+H for $C_{26}H_{31}F_2N_3O_2$: 456.2457. Found: 456.2466.

SCHEME 19

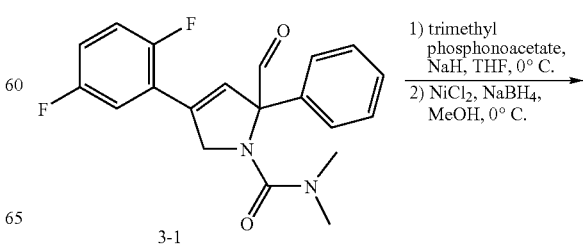

-continued

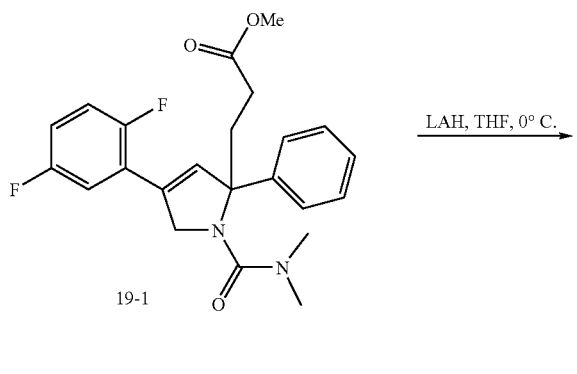

19-1

LAH, THF, 0° C.

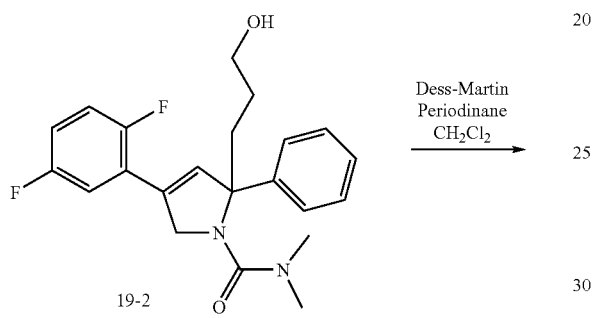

19-2

Dess-Martin
Periodinane
CH₂Cl₂

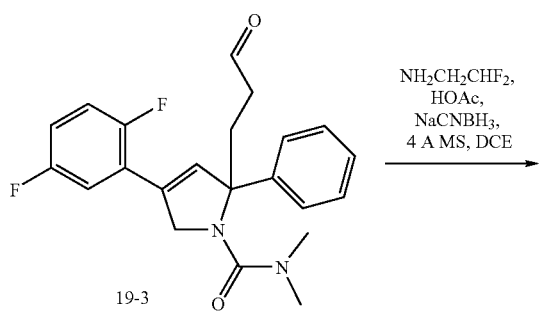

19-3

NH₂CH₂CHF₂,
HOAc,
NaCNBH₃,
4 A MS, DCE

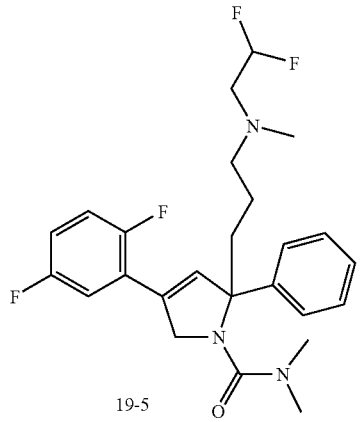

19-4

MeI, NaH, THF

-continued

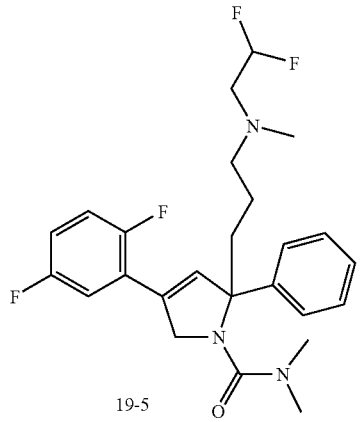

19-5

Step 1: methyl 3-{4-(2,5-difluorophenyl)-1-[(dimethylamino)carbonyl]-2-phenyl-2,5-dihydro-1H-pyrrol-2-yl}propanoate (19-1)

To 1.3 g (3.6 mmol) of aldehyde 3-1 in THF at 0° C. was added 660 μL (4.5 mmol) of trimethyl phosphonoacetate and 220 mg (5.4 mmol) of NaH (60% dispersion in oil). After stirring for 30 min, the reaction was quenched with saturated NH₄Cl, and then partitioned between EtOAc and brine. The organic phase was washed with brine, dried over Na₂SO₄, and concentrated by rotary evaporation. The residue was purified by column chromatography on silica gel with EtOAc/hexanes to provide the (α,β-unsaturated ester as a colorless oil. To 1.0 g (2.4 mmol) of this material in MeOH at 0° C. was added 330 mg of NiCl₂ (2.5 mmol) and 367 mg (9.7 mmol) of NaBH₄. After stirring for 1 h, the reaction was quenched with solid NH₄Cl, partitioned between EtOAc and brine, the organic phase was washed with brine, dried over Na₂SO₄, and concentrated by rotary evaporation. The residue was purified by column chromatography on silica gel with EtOAc/hexanes to provide 19-1 a colorless oil. Data for 19-1: $^1$HNMR (500 MHz, CDCl₃) δ 7.4-7.2 (m, 5H), 7.1-6.9 (m, 3H), 6.1 (s, 1H), 4.9 (m, 1H), 4.7 (m, 1H), 3.6 (s, 3H), 3.3 (m, 1H), 2.8 (s, 6H), 2.6 (m, 1H), 2.45 (m, 1H), 2.35 (m, 1H) ppm. HRMS (ES) calc'd M+H for $C_{23}H_{24}F_2N_2O_3$: 415.1828. Found: 415.1805.

Step 2: 4-(2,5-difluorophenyl)-2-(3-hydroxypropyl)-N,N-dimethyl-2-phenyl-2,5-dihydro-1H-pyrrole-1-carboxamide (19-2)

To 2.5 g (5.9 mmol) of ester 19-1 in THF at 0° C. was added 235 mg (6.2 mmol) of lithium aluminum hydride. After stirring for 30 min, the reaction was quenched with saturated NH₄Cl, partitioned between EtOAc and 10%

Step 3: 2-{3-[(2,2-difluoroethyl)amino]propyl}-4-(2,5-difluorophenyl)-N,N-dimethyl-2-phenyl-2,5-dihydro-1H-pyrrole-1-carboxamide (19-4)

To 1.3 g (4.5 mmol) of alcohol 19-2 in CH₂Cl₂ was added 2.0 g (4.7 mmol) of Dess-Martin Periodinane. After stirring for 90 min. the reaction was quenched with saturated Na$_2$SO$_3$ and saturated NaHCO$_3$. The biphasic mixture was stirred rapidly for 1 h, then separated, the organic phase was washed with saturated NaHCO$_3$, water, dried over Na$_2$SO$_4$, and concentrated by rotary evaporation to provide 19-3 as a pale yellow solid. To 50 mg (0.13 mmol) of this material in 1,2-dichloroethane was added 32 mg (0.39 mmol) of 2,2-difluoroethylamine, ~100 mg of 4A molecular sieves and a few drops of HOAc. After stirring for 90 min at room temperature, 12 mg (0.20 mmol) of NaCNBH$_3$ was added and the reaction was stirred overnight. The mixture was then filtered through Celite with the aid of CH$_2$Cl$_2$, concentrated by rotary evaporation, and the residue was purified by column chromatography on silica gel with EtOAc/hexanes to provide 19-4 a colorless gum. Data for 19-4: $^1$HNMR (500 MHz, CDCl$_3$) δ 7.4-7.2 (m, 5H), 7.1-6.9 (m, 3H), 6.2 (s, 1H), 5.8 (m, 1H), 4.9 (m, 1H), 4.7 (m, 1H), 3.0 (m, 3H), 2.9 (m, 8H), 2.1 (m, 1H), 1.5 (m, 3H) ppm. HRMS (ES) calc'd M+H for C$_{24}$H$_{27}$F$_4$N$_3$O: 450.2163. Found: 450.2204.

Step 4: 2-{3-[(2,2-difluoroethyl)(methyl)amino]propyl}-4-(2,5-difluorophenyl)-N,N-dimethyl-2-phenyl-2,5-dihydro-1H-pyrrole-1-carboxamide (19-5)

To 35 mg (0.08 mmol) of amine 19-4 in THF was added 22 mg (0.55 mmol) of NaH (60% dispersion in oil) and 24 μL (0.39 mmol) of MeI. After stirring for 1 h, the reaction was quenched with water and partitioned with EtOAc, washed with brine, dried over MgSO$_4$, concentrated by rotary evaporation, and the residue was purified by column chromatography on silica gel with EtOAc/hexanes to provide 19-5 a colorless gum. Data for 19-5: $^1$HNMR (500 MHz, CDCl$_3$) δ 7.4-7.2 (m, 5H), 7.1-6.9 (m, 3H), 6.2 (s, 1H), 5.8 (m, 1H), 4.9 (m, 1H), 4.7 (m, 1H), 3.0 (m, 1H), 2.8-2.7 (m, 8H), 2.55 (m, 2H), 2.35 (s, 3H), 2.1 (m, 1H), 1.5 (m, 2H) ppm. HRMS (MS) calc'd M+H for C$_{25}$H$_{29}$F$_4$N$_3$O: 464.2320. Found: 464.2320.

The following compounds were prepared by simple modifications of the above procedure.

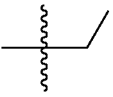

| Compound No. | R$_1$ | R$_2$ | HRMS (calculated) | HRMS (found) |
|---|---|---|---|---|
| 19-6 | H | 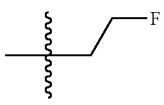 | 414.2352 | 414.2349 |
|  |  |  | (isolated as the TFA salt) |  |
| 19-7 | H | 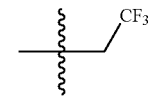 | 432.2257 | 432.2268 |
| 19-8 | H | 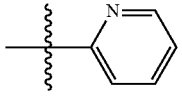 | 468.2069 | 468.2083 |
| 19-9 | H | 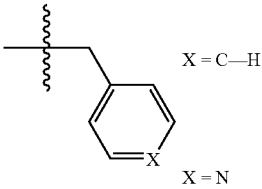 | 463.2304 | 463.2328 |
| 19-10 | H |  | 476.2508 | 476.2525 |
| 19-11 | H |  | 477.2460 | 477.2445 |
|  |  | X = C—H |  |  |
|  |  | X = N |  |  |
|  |  |  | (isolated as the bis-TFA salt) |  |

-continued
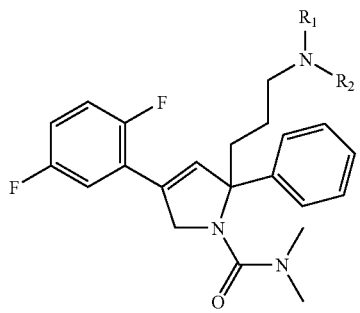
| Compound No. | $R_1$ | $R_2$ | HRMS (calculated) | HRMS (found) |
| --- | --- | --- | --- | --- |
| 19-12 | H | 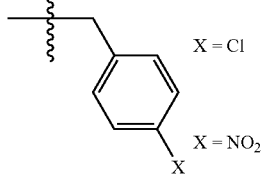 X = Cl | 510.2118 | 510.2111 |
| 19-13 | H | X = NO$_2$ | 521.2359 | 521.2338 |
| 19-14 | H | 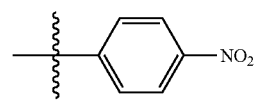 | 507.2202 | 507.2179 |
| 19-15 | CH$_2$CHF$_2$ | 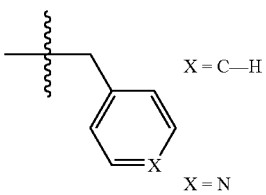 X = C—H | 540.2633 | 540.2610 |
| 19-16 | CH$_2$CHF$_2$ | X = N | 541.2585 | 541.2563 |
| 19-17 | H | 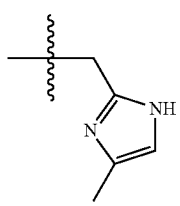 | 480.2569 | 480.2572 |
| | | (isolated as the bis-TFA salt) | | |
| 19-18 | —CH$_2$CH$_2$CH$_2$CH$_2$CH$_2$— | | 454.2665 | 454.2647 |

SCHEME 20

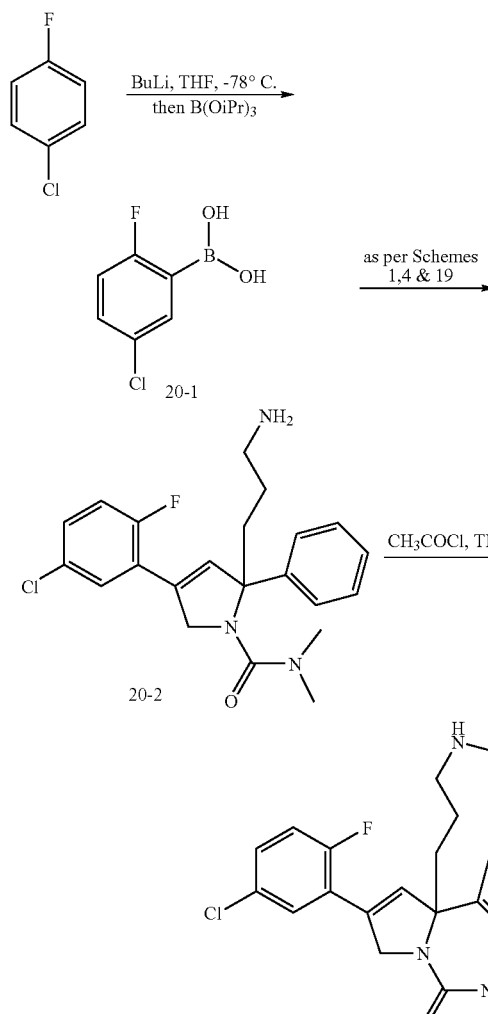

Step 1: 5-chloro-2-fluorophenylboronic acid (20-1)

To 30.0 g (23 mmol) of 1-chloro-4-fluorobenzene in THF at −78° C. was added 14.4 mL (23 mmol) of a n-butyllithium solution (1.6M in hexanes). After stirring for 2.5 h at that temperature, 10.6 mL (46 mmol) of triisopropyl borate was added dropwise, and the reaction was allowed to slowly warm to room temperature and stir overnight. The reaction was carefully quenched with 1M HCl and then extracted three times with Et$_2$O. The combined organic phase was washed with water, dried over MgSO$_4$, and concentrated to provide 20-1 as a white powder. Data for 20-1: $^1$HNMR (500 MHz, CDCl$_3$) δ 7.8 (m, 1H), 7.4 (m, 1H), 7.0 (m, 1H), 5.2 (m, 2H) ppm.

Step 2: 2-(3-aminopropyl)-4-(5-chloro-2-fluorophenyl)-N,N-dimethyl-2-phenyl-2,5-dihydro-1H-pyrrole-1-carboxamide (20-2)

Procedures as described to make 4-3 were employed to provide 20-2 as an off-white solid. Data for 20-2: HRMS (ES) calc'd M+H for C$_{22}$H$_{25}$ClFN$_3$O: 402.1743. Found: 402.1747.

Step 3: 2-[3-(acetylamino)propyl]-4-(5-chloro-2-fluorophenyl)-N,N-dimethyl-2-phenyl-2,5-dihydro-1H-pyrrole-1-carboxamide (20-3)

To 20 mg (0.05 mmol) of amine 20-2 in THF was added 21 µL (0.15 mmol) of triethylamine and 7 µL (0.10 mmol) of acetyl chloride. After stirring overnight the reaction was partitioned between EtOAc and 10% KHSO$_4$, the organic phase was washed with saturated NaHCO$_3$, brine, dried over MgSO$_4$, and concentrated by rotary evaporation. The residue was purified by column chromatography on silica gel with EtOAc/hexanes to provide 20-3 as a white solid. Data for 20-3: $^1$HNMR (500 MHz, d$_6$-DMSO) δ 7.8 (m, 1H), 7.6 (m, 1H), 7.4-7.2 (m, 7H), 6.2 (s, 1H), 4.9 (m, 1H), 4.7 (m, 1H), 3.05 (m, 2H), 2.7 (s, 6H), 2.05 (m, 1H), 1.8 (s, 3H), 1.2-1.1 (m, 3H) ppm. HRMS (ES) calc'd M+H for C$_{24}$H$_{27}$ClFN$_3$O$_2$: 444.1849. Found: 444.1847.

SCHEME 21

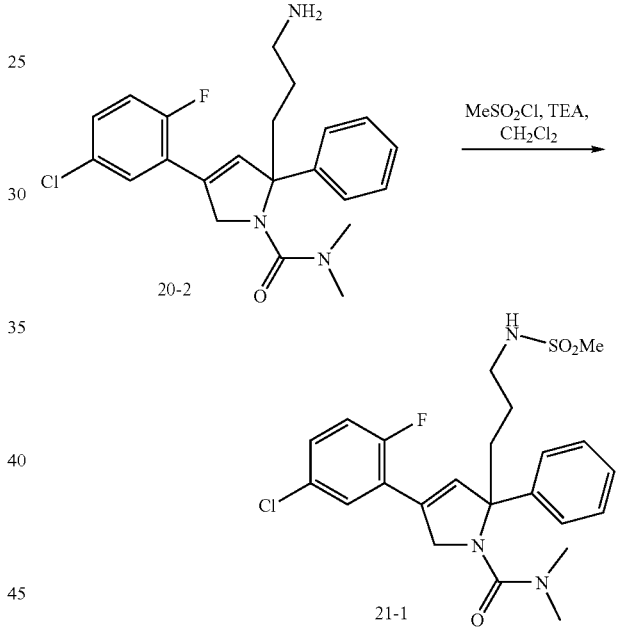

4-(5-chloro-2-fluorophenyl)-N,N-dimethyl-2-{3-[(methylsulfonyl)amino]propyl}-2-phenyl-2,5-dihydro-1H-pyrrole-1-carboxamide (21-4)

To 20 mg (0.05 mmol) of amine 20-2 in CH$_2$Cl$_2$ was added 21 µL (0.15 mmol) of triethylamine and 7.7 µL (0.10 mmol) of methanesulfonyl chloride. After stirring overnight the reaction was partitioned between CH$_2$Cl$_2$ and saturated NaHCO$_3$, the organic phase was washed brine, dried over MgSO$_4$, and concentrated by rotary evaporation. The residue was purified by column chromatography on silica gel with EtOAc/hexanes to provide 21-1 as a white solid. Data for 21-1: $^1$HNMR (500 MHz, d$_6$-DMSO) δ 7.6 (m, 1H), 7.5-7.2 (m, 7H), 6.95 (m, 1H), 6.25 (s, 1H), 4.95 (m, 1H), 4.7 (m, 1H), 3.0 (m, 2H), 2.9 (s, 3H), 2.8 (m, 1H), 2.7 (s, 6H), 2.2 (m, 1H), 1.5 (m, 2H) ppm. HRMS (ES) calc'd M+H for C$_{23}$H$_{27}$ClFN$_3$O$_3$S: 480.1519. Pound: 480.1513.

SCHEME 22

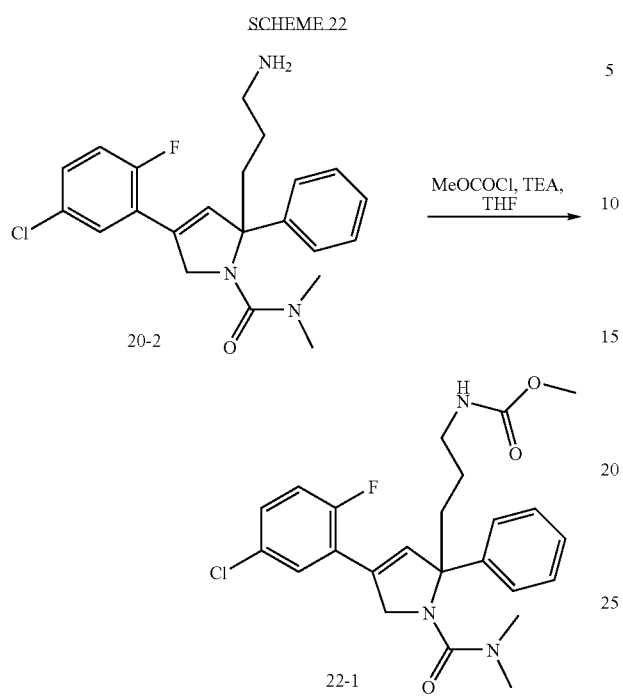

methyl 3-{4-(5-chloro-2-fluorophenyl)-1-[(dimethy-lamino)carbonyl]-2-phenyl-2,5-dihydro-1H-pyrrol-2-yl}propylcarbamate (22-1)

To 20 mg (0.05 mmol) of amine 20-2 in CH$_2$Cl$_2$ was added 21 μL (0.15 mmol) of triethylamine and 5.8 μL (0.10 mmol) of methyl chloroformate. After stirring overnight the reaction was partitioned between EtOAc and 10% KHSO$_4$, the organic phase was washed with saturated NaHCO$_3$, brine, dried over MgSO$_4$, and concentrated by rotary evaporation. The residue was purified by column chromatography on silica gel with EtOAc/hexanes to provide 22-1 as a white solid. Data for 22-1: $^1$HNMR (500 MHz, d$_6$-DMSO) δ 7.6 (m, 1H), 7.5-7.1 (m, 8H), 6.2 (s, 1H), 4.95 (m, 1H), 4.7 (m, 1H), 3.55 (s, 3H), 3.0 (m, 2H), 2.7 (s, 6H), 2.7-2.5 (m, 1H), 2.05 (m, 1H), 1.4 (m, 2H) ppm. HRMS (ES) calc'd M+H for C$_{24}$H$_{27}$ClFN$_3$O$_3$: 460.1798. Found: 460.1797.

SCHEME 23

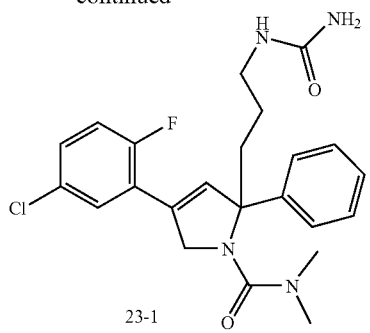

2-{3-[(aminocarbonyl)amino]propyl}-4-(5-chloro-2-fluorophenyl)-N,N-dimethyl-2-phenyl-2,5-dihydro-1H-pyrrole-1-carboxamide (23-1)

To 20 mg (0.05 mmol) of amine 20-2 in CH$_2$Cl$_2$ was added a large excess of trimethylsilyl isocyanate and triethylamine. After stirring for 12 h, the reaction was partitioned between EtOAc and 10% KHSO$_4$, the organic phase was washed with saturated NaHCO$_3$, brine, dried over MgSO$_4$, and concentrated by rotary evaporation. The residue was purified by column chromatography on silica gel with MeOH/CHCl$_3$ to provide 23-1 as a white solid. Data for 23-1: $^1$HNMR (500 MHz, d$_6$-DMSO) δ 7.6 (m, 1H), 7.5-7.1 (m, 7H), 6.2 (s, 1H), 5.95 (m, 1H), 5.3 (s, 2H), 4.95 (m, 1H), 4.7 (m, 1H), 3.0 (m, 2H), 2.7 (s, 6H), 2.1 (m, 1H), 1.3 (m, 3H) ppm. HRMS (ES) calc'd M+H for C$_{23}$H$_{26}$ClFN$_4$O$_2$: 445.1801. Found: 445.1805.

SCHEME 24

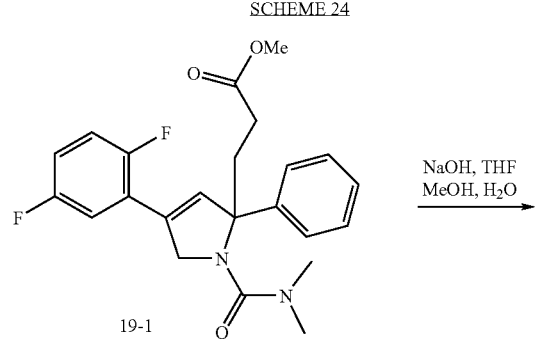

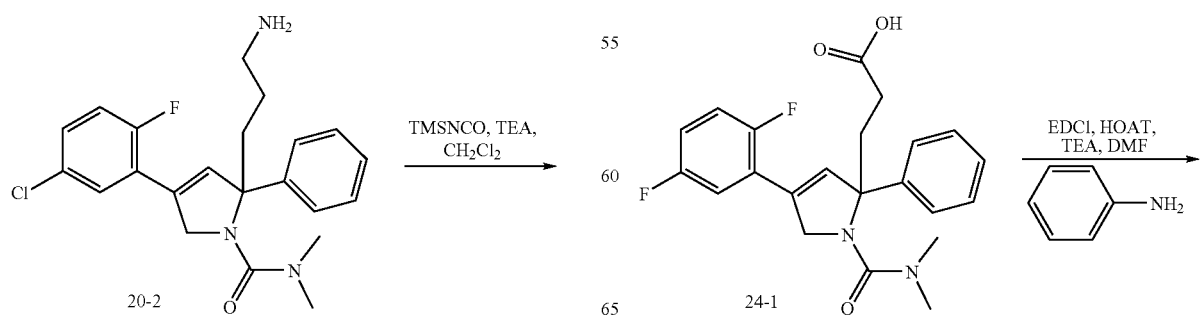

-continued

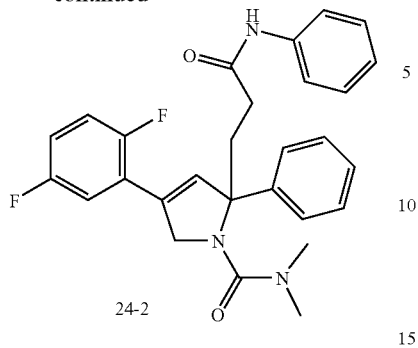
24-2

-continued

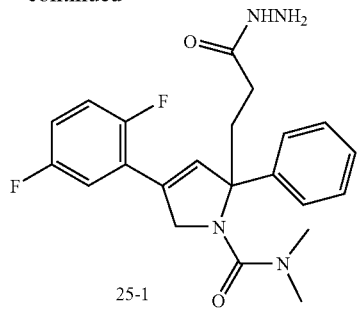
25-1

Step 1: 3-{4-(2,5-difluorophenyl)-1-[(dimethylamino)carbonyl]-2-phenyl-2,5-dihydro-1H-pyrrol-2-yl}propanoic acid (24-1)

To 350 mg (0.85 mmol) of ester 19-1 in a 1:1:1 mixture of THF/MeOH/H$_2$O was added 170 mg (4.25 mmol) of NaOH. After stirring overnight at room temperature, the reaction was quenched with 1M HCl and then extracted three times with EtOAc. The combined organic phase was washed with brine, dried over MgSO$_4$, and concentrated to provide 24-1 as a white solid. Data for 24-1: $^1$HNMR (500 MHz, d$_6$-DMSO) δ 12.0 (s, 1H), 7.5-7.1 (m, 8H), 6.2 (s, 1H), 4.95 (m, 1H), 4.7 (m, 1H), 3.0 (m, 1H), 2.75 (s, 6H), 2.45 (m, 1H), 2.2 (m, 2H) ppm. HRMS (ES) calc'd M+H for C$_{22}$H$_{22}$F$_2$N$_2$O$_3$: 401.1671. Found: 401.1695.

Step 2: 2-(3-anilino-3-oxopropyl)-4-(2,5-difluorophenyl)-N,N-dimethyl-2-phenyl-2,5-dihydro-1H-pyrrole-1-carboxamide (24-2)

To 40 mg (0.10 mmol) of acid 24-1 in DMF was added 11 µL (0.12 mmol) of aniline, 29 mg (0.15 mmol) of EDCI, 17 mg (0.13 mmol) HOAT, and 28 µL (0.20 mmol) of triethylamine. After stirring overnight at room temperature, the reaction was partitioned between EtOAc and 10% KHSO$_4$, the organic phase was washed with saturated NaHCO$_3$, brine, dried over MgSO$_4$, and concentrated. The residue was purified by column chromatography on silica gel with EtOAc/hexanes to provide 24-2 as a white solid. Data for 24-2: $^1$HNMR (500 MHz, d$_6$-DMSO) δ 9.8 (s, 1H), 7.5-7.0 (m, 13H), 6.2 (s, 1H), 5.0 (m, 1H), 4.8 (m, 1H), 3.0 (m, 1H), 2.75 (s, 6H), [(~2.5, under solvent peak (m, 1H)], 2.2 (m, 2H) ppm. HRMS (ES) calc'd M+H for C$_{28}$H$_{27}$F$_2$N$_3$O$_2$: 476.2144. Found: 476.2162

SCHEME 25

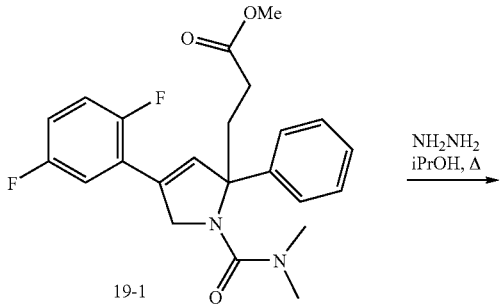
19-1

4-(2,5-difluorophenyl)-2-(3-hydrazino-3-oxopropyl)-N,N-dimethyl-2-phenyl-2,5-hydro-1H-pyrrole-1-carboxamide (25-1)

To 100 mg (0.24 mmol) of ester 19-1 in isopropanol was added 117 µL (2.4 mmol) of hydrazine hydrate. After stirring overnight at reflux, the reaction was concentrated and the residue was purified by column chromatography on silica gel with MeOH/CHCl$_3$ to provide 25-1 as a white solid. Data for 25-1: $^1$HNMR (500 MHz, CDCl$_3$) δ 7.4-6.9 (m, 9H), 6.2 (s, 1H), 4.95 (m, 1H), 4.75 (m, 1H), 3.3 (m, 1H), 2.8 (s, 6H), 2.5 (m, 1H), 2.2 (m, 2H) ppm. HRMS (ES) calc'd M+H for C$_{22}$H$_{24}$F$_2$N$_4$O$_2$: 415.1940. Found: 415.1981.

SCHEME 26

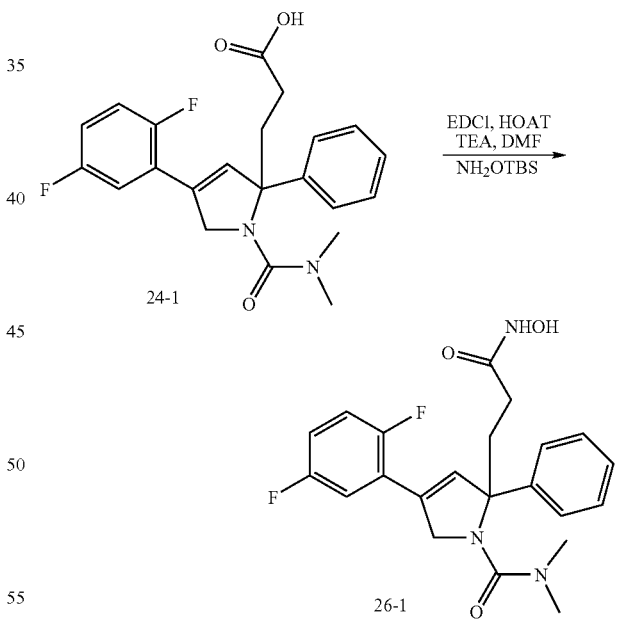

4-(2,5-difluorophenyl)-2-[3-(hydroxyamino)-3-oxopropyl]-N,N-dimethyl-2-phenyl-2,5-dihydro-1H-pyrrole-1-carboxamide (26-1)

To 40 mg (0.10 mmol) of acid 24-1 in DMF was added 18 mg (0.12 mmol) of O-(t-butyldimethylsilyl)hydroxylamine, 29 mg (0.15 mmol) of EDCI, 17 mg (0.13 mmol) HOAT, and 28 µL (0.20 mmol) of triethylamine. After stirring overnight at room temperature, ~300 µL of trifluoroacetic acid was added and stirring was continued for 1 h. The reaction was partitioned between EtOAc and saturated NaHCO₃, the organic phase was washed with brine, dried over MgSO₄, and concentrated. The residue was purified by column chromatography on silica gel with MeOH/CHCl₃ to provide 26-1 as a white solid. Data for 26-1: HRMS (ES) calc'd M+Na for $C_{22}H_{23}F_2N_3O_3$: 438.1599. Found: 438.1618.

The following compounds were prepared by simple modifications of the above procedure.

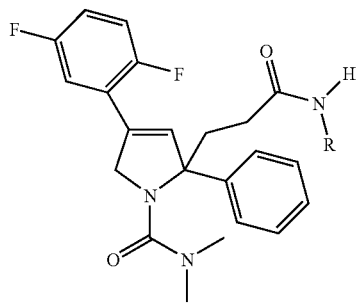

| Compound No. | R | MS (calculated) | HRMS (found) |
|---|---|---|---|
| 26-2 | H | 400.1831 | 400.1867 |
| 26-3 | —O—CH₃ | 430.1937 | 430.1969 |

SCHEME 27

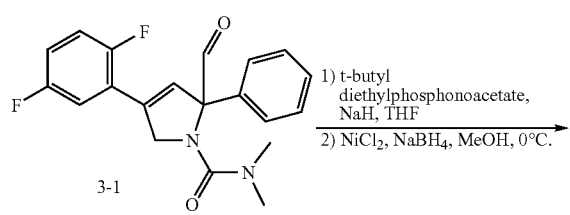

1) t-butyl diethylphosphonoacetate, NaH, THF
2) NiCl₂, NaBH₄, MeOH, 0°C.

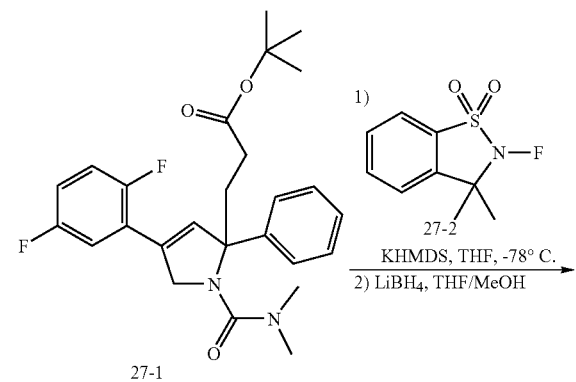

1) 27-2, KHMDS, THF, -78° C.
2) LiBH₄, THF/MeOH

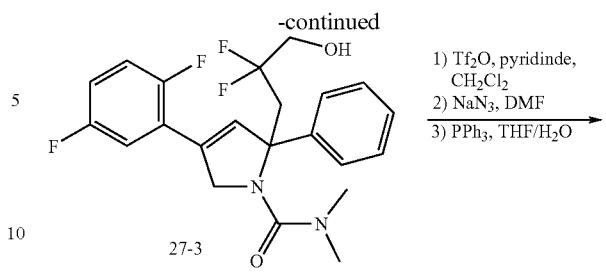

1) Tf₂O, pyridinde, CH₂Cl₂
2) NaN₃, DMF
3) PPh₃, THF/H₂O

Step 1: tert-butyl 3-{4-(2,5-difluorophenyl)-1-[(dimethylamino)carbonyl]-2-phenyl-2,5-dihydro-1H-pyrrol-2-yl}propanoate (27-1)

To 750 mg (2.1 mmol) of aldehyde 3-1 in THF was added 1 mL (4.2 mmol) of t-butyl diethylphosphonoacetate and 170 mg (4.2 mmol) of NaH (60% dispersion in oil). After stirring for 1 h at room temperature, the reaction was quenched with saturated NH₄Cl and then extracted three times with EtOAc. The combined organic phase was washed with brine, dried over Na₂SO₄, concentrated, and the residue was purified by column chromatography on silica gel with EtOAc/hexanes to provide the α,β-unsaturated ester as a pale yellow solid. To 910 mg (2.0 mmol) of this material in MeOH at 0° C. was added 272 mg (2.1 mmol) of NiCl₂ and 305 mg (8 mmol) of NaBH₄. After stirring for 1 h, the reaction was quenched with solid NH₄Cl, the mixture was partitioned between EtOAc and brine, the organic phase was washed with brine, dried over Na₂SO₄, concentrated, and the residue was purified by column chromatography on silica gel with EtOAc/hexanes to provide 27-1 as a colorless oil. Data for 27-1: ¹HNMR (500 MHz, CDCl₃) δ 7.4-7.2 (m, 5H), 7.1-6.9 (m, 3H), 6.15 (s, 1H), 4.85 (m, 1H), 4.75 (m, 1H), 3.2 (m, 1H), 2.8 (s, 6H), 2.5 (m, 1H), 2.35 (m, 1H), 2.25 (m, 2H) 1.4 (s, 9H) ppm.

Step 2: 2-(3-amino-2,2-difluoropropyl)-4-(2,5-difluorophenyl)-N,N-dimethyl-2-phenyl-2,5-dihydro-1H-pyrrole-1-carboxamide (27-4)

To 560 mg (1.2 mmol) of ester 27-1 in THF at −78° C. was added 8.8 mL (4.4 mmol) of KHMDS (0.5 M solution in PhMe). After stirring for 1 h, 950 mg (4.4 mmol) of 27-2 was added dropwise in THF over 10 min, stirring was continued for 1 h at that temperature, the cooling bath was removed, and the reaction was allowed to warm to room temperature and stir overnight. The reaction was quenched with saturated NH₄Cl, extracted twice with EtOAc, washed with brine, dried over Na₂SO₄, and concentrated. This material was dissolved in a 3:1 mixture of THF/MeOH and an excess of LiBH₄ was added and the reaction was heated at 50° C. for 12 h. After cooling to room temperature, the reaction was quenched with saturated NH₄Cl, extracted twice with EtOAc, washed with brine, dried over Na₂SO₄, concentrated, and the residue was purified by column chromatography on silica gel with EtOAc/hexanes to provide 2-(2,2-difluoro-3-hydroxypropyl)-4-(2,5-difluorophenyl)-N,N-dimethyl-2-phenyl-2,5-hydro-1H-pyrrole-1-carboxamide 27-3 as a pale yellow taffy. To 45 mg (0.11 mmol) of alcohol 27-3 in CH₂Cl₂ at 0° C. was added 30 μL (0.32 mmol) of pyridine and 30 μL (0.16 mmol) of trifluoromethanesulfonic anhydride. The reaction was warmed to room temperature and stirring was continued for 1 h. The reaction was quenched with water, washed with 10% KHSO₄, water, dried over Na₂SO₄, and concentrated. The residue was dissolved in DMF, 15 mg (0.22 mmol) of NaN₃ was added, and the mixture was heated at 50° C. for 1 h. After cooling to room temperature, the reaction was partitioned between EtOAc and brine, the organic phase was washed with brine, dried over Na₂SO₄, and concentrated. The residue was purified by column chromatography on silica gel with EtOAc/hexanes to provide the azide as a colorless oil. To 7 mg (0.015 mmol) of the azide in THF was added 8 mg (0.031 mmol) of PPh₃ and the mixture was stirred overnight at room temperature. To the reaction was then added 1 mL of water, and it was heated at 50° C. for 2 h. After cooling to room temperature, the reaction was partitioned between EtOAc and brine, the organic phase was washed with brine, dried over Na₂SO₄, and concentrated. The residue was then purified by reverse phase HPLC to provide 27-4 as a film. Data for 27-4: ¹HNMR (500 MHz, CDCl₃) δ 7.4-7.2 (m, 5H), 7.1-6.9 (m, 3H), 6.35 (s, 1H), 4.85 (m, 1H), 4.75 (m, 1H), 3.7 (m, 2H), 3.0 (m, 2H), 2.8 (s, 6H) ppm. HRMS (ES) calc'd M+H for $C_{22}H_{23}F_4N_3O$: 422.1850. Found: 422.1830.

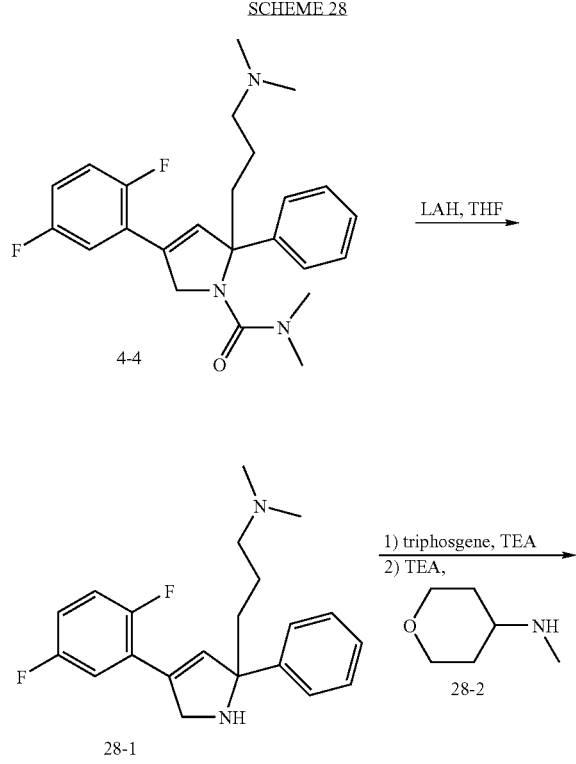

SCHEME 28

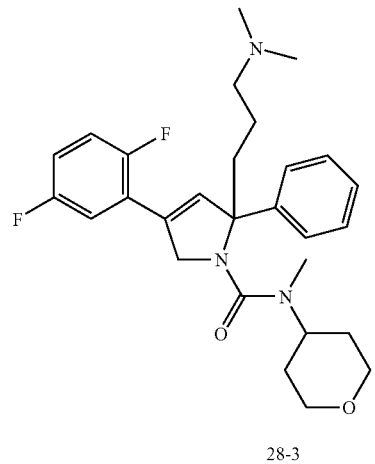

Step 1: 3-[4-(2,5-difluorophenyl)-2-phenyl-2,5-dihydro-1H-pyrrol-2-yl]-N,N-dimethylpropan-1-amine (28-1)

To 480 mg (1.1 mmol) of amine 4-4 in THF was added 3.5 mL (3.5 mmol) of lithium aluminum hydride (1M solution in THF). After stirring for 3 h at room temperature, the reaction was cooled to 0° C. and quenched by the addition of 130 μL of H₂O, 130 μL of 15% aqueous NaOH, and then 400 μL of H₂O. Celite was added, and the mixture was filtered through a pad of celite, the solids were rinsed with hot THF, and the filtrate was concentrated. The residue was purified by column chromatography on silica gel with EtOAc/hexanes and then 20:1:1 EtOH/NH₄OH/H₂O in EtOAc. The product was then purified by reverse phase HPLC to provide the bis-TFA salt of 28-1 as a colorless film. Data for 28-1: HRMS (ES) calc'd M+H for $C_{21}H_{24}F_2N_2$: 343.1981. Found: 343.1975.

Step 2: 4-(2,5-difluorophenyl)-2-[3-(dimethylamino)propyl]-N-methyl-2-phenyl-N-tetrahydro-2H-pyran-4-yl-2,5-dihydro-1H-pyrrole-1-carboxamide (28-3)

To 40 mg (0.12 mmol) of amine 28-1 in THF was added 33 μL (0.24 mmol) of triethylamine, followed by 17 mg (0.06 mmol) of triphosgene. After stirring for 1 h, an additional 66 μL of triethylamine was added, followed by 42 mg (0.28 mmol) of amine 28-2. After stirring for 8 h at 50° C., the reaction was cooled to room temperature, partitioned between EtOAc and saturated NaHCO₃, the organic phase was washed with H₂O, brine, dried over MgSO₄, and concentrated. The residue was then purified by reverse phase HPLC to provide the TFA salt of 28-3 as a white solid. Data for 28-3: ¹HNMR (500 MHz, CDCl3): δ 7.4-7.2 (m, 5H), 7.1-6.9 (m, 3H), 6.15 (s, 1H), 4.8 (m, 1H), 4.7 (m, 1H), 4.0 (m, 2H), 3.8-3.6 (m, 3H), 3.4 (m, 2H), 3.1 (m, 3H), 2.9-2.7 (m, 9H), 1.9-1.5 (m, 5H) ppm. HRMS (ES) calc'd M+H for $C_{28}H_{35}F_2N_3O_2$: 484.2770. Found: 484.2767.

SCHEME 29

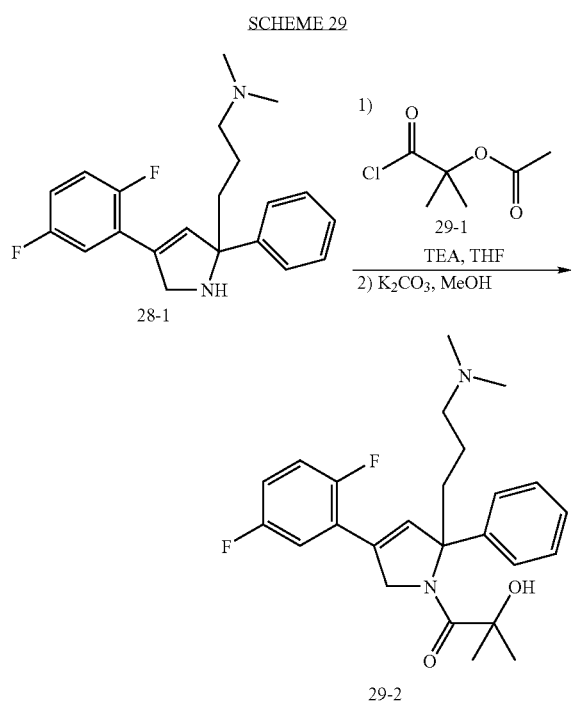

1-{4-(2,5-difluorophenyl)-2-[3-(dimethylamino)propyl]-2-phenyl-2,5-dihydro-1-pyrrol-1-yl}-2-methyl-1-oxopropan-2-ol (29-2)

To 40 mg (0.12 mmol) of amine 28-1 in THF was added 33 µL (0.24 mmol) of triethylamine, followed by 25 µL (0.18 mmol) of acyl chloride 29-1. After stirring overnight, the reaction was partitioned between EtOAc and saturated NaHCO$_3$, the organic phase was washed with H$_2$O, brine, dried over MgSO$_4$, and concentrated. The residue was dissolved in MeOH and 32 mg (0.24 mmol) of K$_2$CO$_3$ was added, and the mixture was stirred for 7 h. The reaction was partitioned between EtOAc and saturated NaHCO$_3$, the organic phase was washed with H$_2$O, brine, dried over MgSO$_4$, and concentrated. The residue was purified by reverse phase HPLC to provide 29-2 as a colorless film. Data for 29-2: $^1$HNMR (500 MHz, CDCl$_3$): δ 7.4-7.2 (m, 5H), 7.1-6.9 (m, 3H), 6.1 (s, 1H), 5.2 (m, 2H), 3.0 (m, 1H), 2.5-2.2 (m, 1H), 1.56 (s, 3H), 1.53 (s, 3H) ppm. HRMS (ES) calc'd M+H for C$_{25}$H$_{30}$F$_2$N$_2$O$_2$: 429.2348. Found: 429.2351.

SCHEME 30

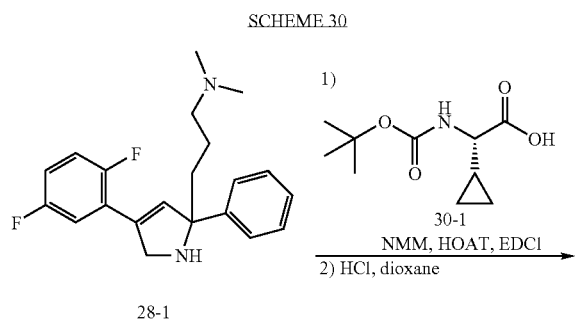

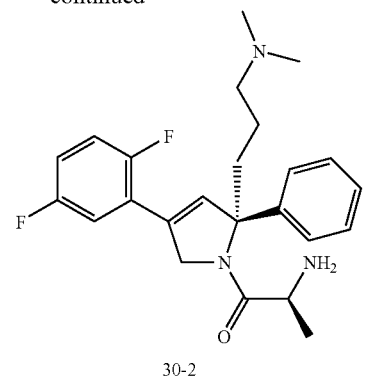

3-[(2S)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine (30-2) and 3-[(2R)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine To 70 mg (0.20 mmol) of amine 28-1 in DMF was added 44 mg (0.20 mmol) of acid 30-1, 31 mg (0.22 mmol) of HOAT, 51 mg (0.26 mmol) of EDCI and 67 µL (0.61 mmol) of N-methylmorpholine. After stirring overnight, the reaction was partitioned between EtOAc and saturated NaHCO$_3$, the organic phase was washed with H$_2$O, 10% KHSO$_4$, brine, dried over MgSO$_4$, and concentrated. The residue was purified by column chromatography on silica gel with EtOAc/hexanes and then 20:1:1 EtOH/NH$_4$OH/H$_2$O in EtOAc to provide a yellow oil. The residue was dissolved in 1:1 CH$_2$Cl$_2$/4M HCl in dioxane and the mixture was stirred for 8 h at 0° C. The reaction was concentrated and the residue was purified by reverse phase HPLC to provide both diastereomers of the bis-TFA salts of title compound as white solids—the second one to elute being most active. Data for 30-2 (second isomer to elute): $^1$HNMR (500 MHz, CD$_3$OD): δ 7.5-7.1 (m, 8H), 6.3 (s, 1H), 5.1 (m, 1H), 5.0 (m, 1H), 4.05 (m, 1H), 3.2 (m, 2H), 3.1 (m, 1H), 2.85 (m, 6H), 2.3 (m, 1H), 1.9-1.7 (m, 2H), 1.2 (m, 1H), 0.9-0.7 (m, 3H), 0.5 (m, 1H) ppm. HRMS (ES) calc'd M+H for C$_{26}$H$_{31}$F$_2$N$_3$O: 440.2508. Found: 440.2489.

The following compounds were prepared by simple modifications of the above procedure.

| Structure | HRMS (calculated) | HRMS (found) |
|---|---|---|
| 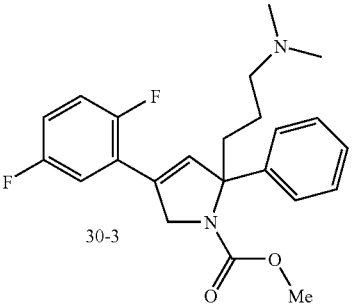 | 343.1981 | 343.1975 |

| Structure | HRMS (calculated) | HRMS (found) |
|---|---|---|
| 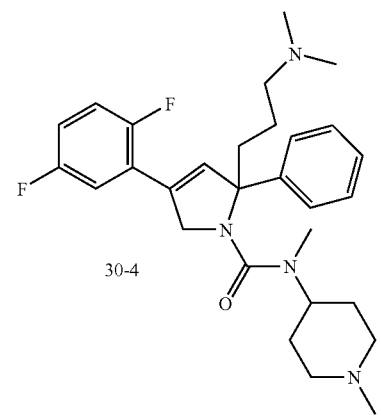 (30-4) (isolated as bis-TFA salt) | 401.2035 | 401.2025 |

SCHEME 31

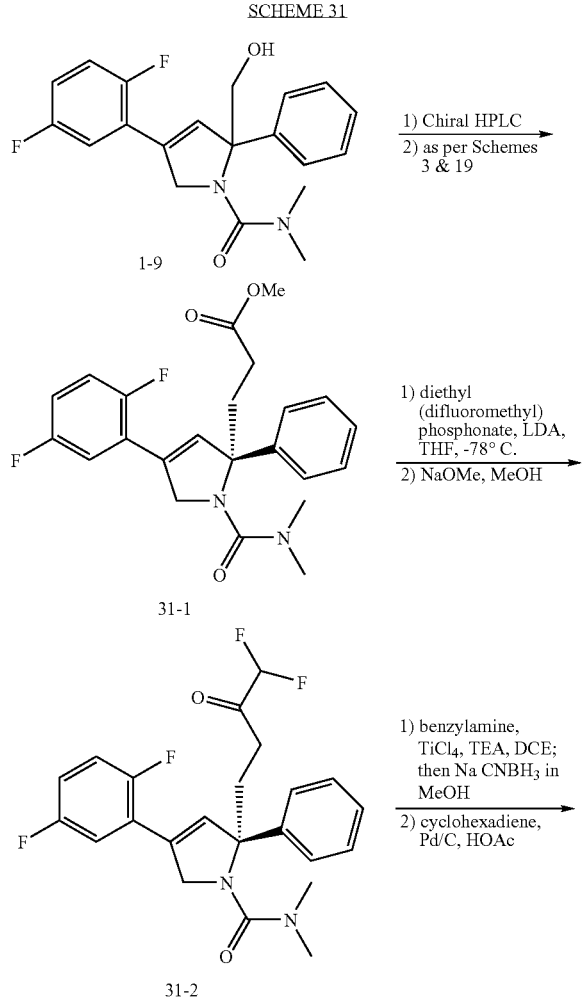

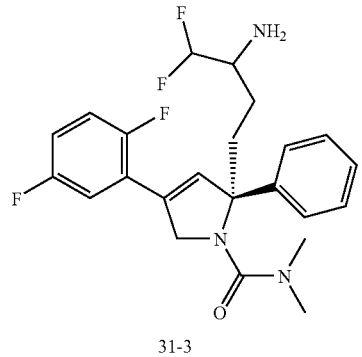

Step 1: methyl 3-{(2S)-4-(2,5-difluorophenyl)-1-[(dimethylamino)carbonyl]-2-phenyl-2,5-dihydro-1H-pyrrol-2-yl}propanoate (31-1)

Resolution of the enantiomers of 1-9 was carried out chromatographically using a Chiralpak AD© 10×50 cm column with 15% ethanol in hexanes (with 0.1% diethylamine) at 150 mL/min. Analytical HPLC analysis of the eluent on a 4×250 mm Chiralpak AD® column with 15% ethanol in hexanes (with 0.1% diethylamine) at 1 mL/min indicated that inactive enantiomer has $R_t$=8.0 min and the active enantiomer has $R_t$=9.1 min. The second isomer was then advanced to 31-1 as previously described in Schemes 3 and 19.

Step 2: (2S)-2-(4,4-difluoro-3-oxobutyl)-4-(2,5-difluorophenyl)-N,N-methyl-2-phenyl-2,5-dihydro-1H-pyrrole-1-carboxamide (31-2)

To 110 μL (0.72 mmol) of diethyl (difluoromethyl)phosphonate in THF at −78° C. was added 400 μL (0.72 mmol) of LDA (1.8M solution in heptane/THF/ethylbenzene). After stirring for 30 min, a solution of 250 mg (0.60 mmol) of ester 31-1 in THF was added dropwise, and the resulting solution was stirred for 2 h at −78° C. After quenching the reaction with 2 drops of HOAc, it was partitioned between EtOAc and saturated $NH_4Cl$, the organic phase was washed with brine, dried over $Na_2SO_4$, and concentrated by rotary evaporation. The residue was purified by column chromatography on silica gel with EtOAc/hexanes to provide 250 mg (0.44 mmol) of a colorless oil. This material was dissolved in MeOH, 12 mg (0.22 mmol) of NaOMe was added and the solution was stirred at room temperature for 3 h. The reaction was then partitioned between $CH_2Cl_2$ and water, the aqueous layer was extracted 3 more times with $CH_2Cl_2$, the combined organic phase was washed with water, dried over $Na_2SO_4$, and concentrated to provide crude difluoroketone 31-2 as a colorless oil. Data for 31-2: HRMS (ES) calc'd M+H for $C_{23}H_{22}F_4N_2O_2$: 435.1690. Found: 435.1668.

Step 3: (2S)-2-(3-amino-4,4-difluorobutyl)-4-(2,5-difluorophenyl)-N,N-dimethyl-2-phenyl-2,5-dihydro-1H-pyrrole-1-carboxamide (31-3)

To 100 mg (0.23 mmol) of ketone 31-2 in 1,2-dichloroethane was added 38 μL (0.35 mmol) of benzylamine, 96 μL (0.69 mmol) of triethylamine, and 120 μL (0.12 mmol) of $TiCl_4$ solution (1M in $CH_2Cl_2$). After stirring for 15 h, a solution of 44 mg (0.69 mmol) of $NaCNBH_3$ in MeOH was added and the mixture stirred for an additional 1 h. The reaction was then partitioned between EtOAc and saturated NaHCO$_3$, the organic phase was washed with H$_2$O, brine, dried over MgSO$_4$, and concentrated. The residue was purified by column chromatography on silica gel with EtOAc/hexanes to provide the separable benzylamine diastereomers. The first diastereomer to elute was then carried on as follows: To 40 mg (0.076 mmol) of this material in HOAc was added ~20 mg of 10% palladium on carbon, 72 µL (0.76 mmol) of 1,4-cyclohexadiene, and the reaction was heated at 60° C. for 3 h. After cooling to room temperature, the reaction was filtered through Celite, concentrated by rotary evaporation, and the residue was purified by column chromatography on silica gel with EtOAc/hexanes to provide 31-3 as a colorless gum. Data for 31-3: $^1$HNMR (500 MHz, CDCl$_3$) δ 7.4-7.2 (m, 5H), 7.1-6.9 (m, 3H), 6.2 (s, 1H), 5.6 (m, 1H), 4.85 (m, 1H), 4.7 (m, 1H), 3.0 (m, 2H), 2.8 (s, 6H), 2.4 (m, 1H), 1.4-1.2 (m, 2H) ppm. HRMS (ES) calc'd M+H for C$_{23}$H$_{25}$F$_4$N$_3$O: 436.2007. Found: 436.1998.

What is claimed is:
1. A compound of Formula I:

or a pharmaceutically acceptable salt or stereoisomer thereof,
wherein:
a is 0 or 1;
b is 0 or 1;
m is 0, 1, or 2;
n is 0;
r is 0 or 1;
s is 0 or 1;
R$^1$ is selected from:
  1) (C$_1$-C$_6$-alkylene)$_n$(C=O)C$_1$-C$_{10}$ alkyl, and
  7) (C$_1$-C$_6$-alkylene)$_n$(C=O)NR$^c$R$^{c'}$,
said alkyl, is optionally substituted with one or more substituents selected from R$^{10}$;
R$^2$ and R$^6$ are independently selected from:
  1) aryl,
said aryl is optionally substituted with one or more substituents selected from R$^{10}$;
R$^3$ is selected from:
  1) C$_1$-C$_{10}$ alkyl-O—R$^g$,
  2) C$_1$-C$_{10}$ alkyl-(C=O)$_b$—NR$^f$R$^{f'}$,
said alkyl is optionally substituted with one or more substituents selected from R$^{10}$;
R$^4$ is selected from:
  1) H, and
  2) C$_1$-C$_{10}$ alkyl,
said alkyl is optionally substituted with one or more substituents selected from R$^{10}$;
R$^5$ and R$^7$ are independently selected from:
  1) H, and
  2) C$_1$-C$_{10}$ alkyl,
said alkyl is optionally substituted with one or more substituents selected from R$^{10}$;
R$^{10}$ is independently selected from:
  1) (C=O)$_a$O$_b$C$_1$-C$_{10}$ alkyl,
  2) (C=O)$_a$O$_b$aryl,
  3) C$_2$-C$_{10}$ alkenyl,
  4) C$_2$-C$_{10}$ alkynyl,
  5) (C=O)$_a$O$_b$ heterocyclyl,
  6) CO$_2$H,
  7) halo,
  8) CN,
  9) OH,
  10) O$_b$C$_1$-C$_6$ perfluoroalkyl,
  11) O$_a$(C=O)$_b$NR$^{12}$R$^{13}$,
  12) S(O)$_m$R$^a$, 13) $S(O)_2NR^{12}R^{13}$,
14) oxo,
15) CHO,
16) $(N=O)R^{12}R^{13}$, or
17) $(C=O)_aO_bC_3-C_8$ cycloalkyl, said alkyl, aryl, alkenyl, alkynyl, heterocyclyl, and cycloalkyl optionally substituted with one, two or three substituents selected from $R^{11}$;

$R^{11}$ is selected from:
1) $(C=O)_rO_s(C_1-C_{10})$alkyl,
2) $O_r(C_1-C_3)$perfluoroalkyl,
3) oxo,
4) OH,
5) halo,
6) CN,
7) $(C_2-C_{10})$alkenyl,
8) $(C_2-C_{10})$alkynyl,
9) $(C=O)_rO_s(C_3-C_6)$cycloalkyl,
10) $(C=O)_rO_s(C_0-C_6)$alkylene-aryl,
11) $(C=O)_rO_s(C_0-C_6)$alkylene-heterocyclyl,
12) $(C=O)_rO_s(C_0-C_6)$alkylene-$N(R^b)_2$,
13) $C(O)R^a$,
14) $(C_0-C_6)$alkylene-$CO_2R^a$,
15) $C(O)H$,
16) $(C_0-C_6)$alkylene-$CO_2H$, and
17) $C(O)N(R^b)_2$,
18) $S(O)_mR^a$, and
19) $S(O)_2N(R^b)_2$;

said alkyl, alkenyl, alkynyl, cycloalkyl, aryl, alkylene and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $NO_2$ and $N(R^b)_2$;

$R^{12}$ and $R^{13}$ are independently selected from:
1) H,
2) $(C=O)O_bC_1-C_{10}$ alkyl,
3) $(C=O)O_bC_3-C_8$ cycloalkyl,
4) $(C=O)O_b$aryl,
5) $(C=O)O_b$heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl,
12) $SO_2R^a$, and
13) $(C=O)NR^b_2$, said alkyl, cycloalkyl, aryl, heterocylyl, alkenyl, and alkynyl is optionally substituted with one, two or three substituents selected from $R^{11}$, or $R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^a$ is independently selected from: $(C_1-C_6)$alkyl, $(C_3-C_6)$ cycloalkyl, aryl, or heterocyclyl, optionally substituted with one, two or three substituents selected from $R^{11}$;

$R^b$ is independently selected from: H, $(C_1-C_6)$alkyl, aryl, heterocyclyl, $(C_3-C_6)$cycloalkyl, $(C=O)OC_1-C_6$ alkyl, $(C=O)C_1-C_6$ alkyl, $(C=O)$aryl, $(C=O)$heterocyclyl, $(C=O)NR^fR^{f'}$ or $S(O)_2R^a$, optionally substituted with one, two or three substituents selected from $R^{11}$;

$R^c$ and $R^{c'}$ are independently selected from: H, $(C_1-C_6)$ alkyl, heterocyclyl and $(C_3-C_6)$cycloalkyl, optionally substituted with one, two or three substituents selected from $R^{11}$; or $R^c$ and $R^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^d$ and $R^{d'}$ are independently selected from: $(C_1-C_6)$alkyl, $(C_1-C_6)$alkoxy and $NR^b_2$, or $R^d$ and $R^{d'}$ can be taken together with the phosphorous to which they are attached to form a monocyclic heterocycle with 3-7 members the ring and optionally containing, in addition to the phosphorous, one or two additional heteroatoms selected from $NR^e$, O and S, said monocyclic heterocycle optionally substituted with one, two or three substituents selected from $R^{11}$; and $R^e$ is selected from: H and $(C_1-C_6)$alkyl, optionally substituted with one, two or three substituents selected from $R^{11}$;

$R^f$ and $R^{f'}$ are independently selected from: H, $(C_1-C_6)$ alkyl, aryl, $NH_2$, OH, $OR^a$, —$(C_1-C_6)$alkyl-OH, —$(C_1-C_6)$alkyl-O—$(C_1-C_6)$alkyl, $(C=O)OC_1-C_6$ alkyl, $(C=O)C_1-C_6$ alkyl, $(C=O)$aryl, $(C=O)$heterocyclyl, $(C=O)NR^fR^{f'}$, $S(O)_2R^a$ and —$(C_1-C_6)$alkyl-$N(R^b)_2$, wherein the alkyl is optionally substituted with one, two or three substituents selected from $R^{11}$; or $R^f$ and $R^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^g$ is selected from: H, $(C_1-C_6)$alkyl, —$(C_1-C_6)$alkyl-OH, —$(C_1-C_6)$alkyl-O—$(C_1-C_6)$alkyl and —$(C_1-C_6)$alkyl-$N(R^b)_2$.

2. The compound according to claim 1 of Formula I:

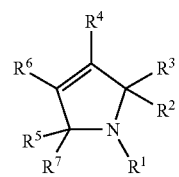

or a pharmaceutically acceptable salt or stereoisomer thereof,
wherein:
a is 0 or 1;
b is 0 or 1;
m is 0, 1, or 2;
n is 0;
r is 0 or 1;
s is 0 or 1;
$R^1$ is selected from:
1) $(C_1-C_6$-alkylene$)_n(C=O)C_1-C_{10}$ alkyl,
2) $(C_1-C_6$-alkylene$)_n(C=O)NR^cR^{c'}$, said alkyl is optionally substituted with one or more substituents selected from $R^{10}$;

$R^2$ and $R^6$ are independently selected from:
1) aryl, said aryl, is optionally substituted with one or more substituents selected from $R^{10}$;

$R^3$ is selected from:
1) $C_1$-$C_{10}$ alkyl-O—$R^g$,
2) $C_1$-$C_{10}$ alkyl-(C=O)$_b$—NR$^f$R$^{f'}$, said alkyl is optionally substituted with one or more substituents selected from $R^{10}$;

$R^4$ is selected from:
1) H,
2) $C_1$-$C_{10}$ alkyl, said alkyl is optionally substituted with one or more substituents selected from $R^{10}$;

$R^5$ and $R^7$ are independently selected from:
1) H,
2) $C_1$-$C_{10}$ alkyl, said alkyl is optionally substituted with one or more substituents selected from $R^{10}$;

$R^{10}$ is independently selected from:
1) (C=O)$_a$O$_b$$C_1$-$C_{10}$ alkyl,
2) (C=O)$_a$O$_b$aryl,
3) $C_2$-$C_{10}$ alkenyl,
4) $C_2$-$C_{10}$ alkynyl,
5) (C=O)$_a$O$_b$ heterocyclyl,
6) $CO_2H$,
7) halo,
8) CN,
9) OH,
10) O$_b$$C_1$-$C_6$ perfluoroalkyl,
11) O$_a$(C=O)$_b$NR$^{12}$R$^{13}$,
12) S(O)$_m$R$^a$,
13) S(O)$_2$NR$^{12}$R$^{13}$,
14) oxo,
15) CHO,
16) (N=O)R$^{12}$R$^{13}$, or
17) (C=O)$_a$O$_b$$C_3$-$C_8$ cycloalkyl, said alkyl, aryl, alkenyl, alkynyl, heterocyclyl, and cycloalkyl optionally substituted with one, two or three substituents selected from $R^{11}$;

$R^{11}$ is selected from:
1) (C=O)$_r$O$_s$($C_1$-$C_{10}$)alkyl,
2) O$_r$($C_1$-$C_3$)perfluoroalkyl,
3) oxo,
4) OH,
5) halo,
6) CN,
7) ($C_2$-$C_{10}$)alkenyl,
8) ($C_2$-$C_{10}$)alkynyl,
9) (C=O)$_r$O$_s$($C_3$-$C_6$)cycloalkyl,
10) (C=O)$_r$O$_s$($C_0$-$C_6$)alkylene-aryl,
11) (C=O)$_r$O$_s$($C_0$-$C_6$)alkylene-heterocyclyl,
12) (C=O)$_r$O$_s$($C_0$-$C_6$)alkylene-N(R$^b$)$_2$,
13) C(O)R$^a$,
14) ($C_0$-$C_6$)alkylene-$CO_2$R$^a$,
15) C(O)H,
16) ($C_0$-$C_6$)alkylene-$CO_2$H, and
17) C(O)N(R$^b$)$_2$,
18) S(O)$_m$R$^a$, and
19) S(O)$_2$N(R$^b$)$_2$;

said alkyl, alkenyl, alkynyl, cycloalkyl, aryl, alkylene and heterocyclyl is optionally substituted with up to three substituents selected from R$^b$, OH, ($C_1$-$C_6$)alkoxy, halogen, $CO_2H$, CN, O(C=O)$C_1$-$C_6$ alkyl, oxo, and N(R$^b$)$_2$;

$R^{12}$ and $R^{13}$ are independently selected from:
1) H,
2) (C=O)O$_b$$C_1$-$C_{10}$ alkyl,
3) (C=O)O$_b$$C_3$-$C_8$ cycloalkyl,
4) (C=O)O$_b$aryl,
5) (C=O)O$_b$heterocyclyl,
6) $C_1$-$C_{10}$ alkyl,
7) aryl,
8) $C_2$-$C_{10}$ alkenyl,
9) $C_2$-$C_{10}$ alkynyl,
10) heterocyclyl,
11) $C_3$-$C_8$ cycloalkyl,
12) SO$_2$R$^a$, and
13) (C=O)NR$^b$$_2$, said alkyl, cycloalkyl, aryl, heterocylyl, alkenyl, and alkynyl is optionally substituted with one, two or three substituents selected from $R^{11}$, or $R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

R$^a$ is independently selected from: ($C_1$-$C_6$)alkyl, ($C_3$-$C_6$)cycloalkyl, aryl, or heterocyclyl, optionally substituted with one, two or three substituents selected from $R^{11}$;

R$^b$ is independently selected from: H, ($C_1$-$C_6$)alkyl, aryl, heterocyclyl, ($C_3$-$C_6$)cycloalkyl, (C=O)OC$_1$-$C_6$ alkyl, (C=O)$C_1$-$C_6$ alkyl, (C=O)aryl, (C=O)heterocyclyl, (C=O)NR$^f$R$^{f'}$ or S(O)$_2$R$^a$, optionally substituted with one, two or three substituents selected from $R^{11}$;

R$^c$ and R$^{c'}$ are independently selected from: H, ($C_1$-$C_6$) alkyl, heterocyclyl and ($C_3$-$C_6$)cycloalkyl, optionally substituted with one, two or three substituents selected from $R^{11}$; or R$^c$ and R$^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

R$^d$ and R$^{d'}$ are independently selected from: ($C_1$-$C_6$)alkyl, ($C_1$-$C_6$)alkoxy and NR$^b$$_2$, or R$^d$ and R$^{d'}$ can be taken together with the phosphorous to which they are attached to form a monocyclic heterocycle with 3-7 members the ring and optionally containing, in addition to the phosphorous, one or two additional heteroatoms selected from NR$^e$, O and S, said monocyclic heterocycle optionally substituted with one, two or three substituents selected from $R^{11}$; and R$^e$ is selected from: H and ($C_1$-$C_6$)alkyl, optionally substituted with one, two or three substituents selected from $R^{11}$;

R$^f$ and R$^{f'}$ are independently selected from: H, ($C_1$-$C_6$) alkyl, —($C_1$-$C_6$)alkyl-OH, —($C_1$-$C_6$)alkyl-O—($C_1$-$C_6$)alkyl and —($C_1$-$C_6$)alkyl-N(R$^b$)$_2$, or R$^f$ and R$^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^g$ is selected from: H, $(C_1-C_6)$alkyl, —$(C_1-C_6)$alkyl-OH, —$(C_1-C_6)$alkyl-O—$(C_1-C_6)$alkyl and —$(C_1-C_6)$alkyl-$N(R^b)_2$.

3. The compound according to claim 2 of Formula II:

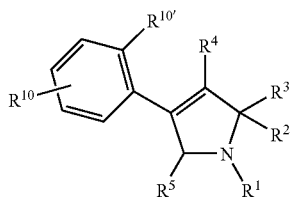

or a pharmaceutically acceptable salt or stereoisomer thereof, wherein
a is 0 or 1;
b is 0 or 1;
m is 0, 1, or 2;
r is 0 or 1;
s is 0 or 1;
$R^1$ is selected from:
  1) (C=O)$C_1-C_{10}$ alkyl, and
  7) (C=O)NR$^c$R$^{c'}$,
said alkyl is optionally substituted with one or more substituents selected from $R^{10}$;
$R^2$ is selected from:
  1) aryl,
said aryl is optionally substituted with one or more substituents selected from $R^{10}$;
$R^3$ is selected from:
  1) $C_1-C_{10}$ alkyl-O—$R^g$,
  2) $C_1-C_{10}$ alkyl-NR$^f$R$^{f'}$,
said alkyl is optionally substituted with one or more substituents selected from $R^{10}$;
$R^4$ and $R^5$ are independently selected from:
  1) H, and
  2) $C_1-C_{10}$ alkyl,
said alkyl is optionally substituted with one or more substituents selected from $R^{10}$;
$R^{10}$ is independently selected from:
  1) (C=O)$_a$O$_b$C$_1$-C$_{10}$ alkyl,
  2) (C=O)$_a$O$_b$aryl,
  3) $C_2-C_{10}$ alkenyl,
  4) $C_2-C_{10}$ alkynyl,
  5) (C=O)$_a$O$_b$ heterocyclyl,
  6) CO$_2$H,
  7) halo,
  8) CN,
  9) OH,
  10) O$_b$C$_1$-C$_6$ perfluoroalkyl,
  11) O$_a$(C=O)$_b$NR$^{12}$R$^{13}$,
  12) S(O)$_m$R$^a$,
  13) S(O)$_2$NR$^{12}$R$^{13}$,
  14) oxo,
  15) CHO,
  16) (N=O)R$^{12}$R$^{13}$, or
  17) (C=O)$_a$O$_b$C$_3$-C$_8$ cycloalkyl,
said alkyl, aryl, alkenyl, alkynyl, heterocyclyl, and cycloalkyl optionally substituted with one, two or three substituents selected from $R^{11}$;
$R^{10'}$ is halogen;

$R^{11}$ is selected from:
  1) (C=O)$_r$O$_s$(C$_1$-C$_{10}$)alkyl,
  2) O$_r$(C$_1$-C$_3$)perfluoroalkyl,
  3) oxo,
  4) OH,
  5) halo,
  6) CN,
  7) (C$_2$-C$_{10}$)alkenyl,
  8) (C$_2$-C$_{10}$)alkynyl,
  9) (C=O)$_r$O$_s$(C$_3$-C$_6$)cycloalkyl,
  10) (C=O)$_r$O$_s$(C$_0$-C$_6$)alkylene-aryl,
  11) (C=O)$_r$O$_s$(C$_0$-C$_6$)alkylene-heterocyclyl,
  12) (C=O)$_r$O$_s$(C$_0$-C$_6$)alkylene-N(R$^b$)$_2$,
  13) C(O)R$^a$,
  14) (C$_0$-C$_6$)alkylene-CO$_2$R$^a$,
  15) C(O)H,
  16) (C$_0$-C$_6$)alkylene-CO$_2$H, and
  17) C(O)N(R$^b$)$_2$,
  18) S(O)$_m$R$^a$, and
  19) S(O)$_2$N(R$^b$)$_2$;
said alkyl, alkenyl, alkynyl, cycloalkyl, aryl, and heterocyclyl is optionally substituted with up to three substituents selected from $R^b$, OH, $(C_1-C_6)$alkoxy, halogen, CO$_2$H, CN, O(C=O)C$_1$-C$_6$ alkyl, oxo, and N(R$^b$)$_2$;

$R^{12}$ and $R^{13}$ are independently selected from:
  1) H,
  2) (C=O)O$_b$C$_1$-C$_{10}$ alkyl,
  3) (C=O)O$_b$C$_3$-C$_8$ cycloalkyl,
  4) (C=O)O$_b$aryl,
  5) (C=O)O$_b$heterocyclyl,
  6) C$_1$-C$_{10}$ alkyl,
  7) aryl,
  8) C$_2$-C$_{10}$ alkenyl,
  9) C$_2$-C$_{10}$ alkynyl,
  10) heterocyclyl,
  11) C$_3$-C$_8$ cycloalkyl,
  12) SO$_2$R$^a$, and
  13) (C=O)NR$^b_2$,
said alkyl, cycloalkyl, aryl, heterocylyl, alkenyl, and alkynyl is optionally substituted with one, two or three substituents selected from $R^{11}$, or
$R^{12}$ and $R^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;
$R^a$ is independently selected from: $(C_1-C_6)$alkyl, $(C_3-C_6)$cycloalkyl, aryl, or heterocyclyl, optionally substituted with one, two or three substituents selected from $R^{11}$;
$R^b$ is independently selected from: H, $(C_1-C_6)$alkyl, aryl, heterocyclyl, $(C_3-C_6)$cycloalkyl, (C=O)OC$_1$-C$_6$ alkyl, (C=O)C$_1$-C$_6$ alkyl, (C=O)aryl, (C=O)heterocyclyl, (C=O)NR$^f$R$^{f'}$ or S(O)$_2$R$^a$, optionally substituted with one, two or three substituents selected from $R^{11}$;
$R^c$ and $R^{c'}$ are independently selected from: H, $(C_1-C_6)$ alkyl, heterocyclyl and $(C_3-C_6)$cycloalkyl, optionally substituted with one, two or three substituents selected from $R^{11}$; or
$R^c$ and $R^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^d$ and $R^{d'}$ are independently selected from: $(C_1-C_6)$alkyl, $(C_1-C_6)$alkoxy and $NR^b{}_2$, or $R^d$ and $R^{d'}$ can be taken together with the phosphorous to which they are attached to form a monocyclic heterocycle with 3-7 members the ring and optionally containing, in addition to the phosphorous, one or two additional heteroatoms selected from $NR^e$, O and S, said monocyclic heterocycle optionally substituted with one, two or three substituents selected from $R^{11}$;

$R^e$ is selected from: H and $(C_1-C_6)$alkyl, optionally substituted with one, two or three substituents selected from $R^{11}$;

$R^f$ and $R^{f'}$ are independently selected from: H, $(C_1-C_6)$alkyl, $-(C_1-C_6)$alkyl-OH, $-(C_1-C_6)$alkyl-O—$(C_1-C_6)$alkyl and $-(C_1-C_6)$alkyl-N$(R^b)_2$, or $R^f$ and $R^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from $R^{11}$;

$R^g$ is selected from: H, $(C_1-C_6)$alkyl, $-(C_1-C_6)$alkyl-OH, $-(C_1-C_6)$alkyl-O—$(C_1-C_6)$alkyl and $-(C_1-C_6)$alkyl-N$(R^b)_2$.

4. The compound according to claim 3 of the Formula II, or a pharmaceutically acceptable salt or stereoisomer thereof, wherein $R^2$ is phenyl, optionally substituted with one or two substituents selected from $R^{10}$.

5. The compound according to claim 1 of the formula II:

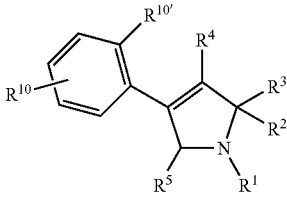

II or a pharmaceutically acceptable salt or stereoisomer thereof, wherein
a is 0 or 1;
b is 0 or 1;
m is 0, 1, or 2;
r is 0 or 1;
s is 0 or 1;
$R^1$ is selected from:
 1) $(C=O)C_1-C_{10}$ alkyl, and
 2) $(C=O)NR^cR^{c'}$,
said alkyl is optionally substituted with one or more substituents selected from $R^{10}$;
$R^2$ is phenyl, optionally substituted with one or more substituents selected from $R^{10}$;
$R^3$ is selected from:
 1) $C_1-C_{10}$ alkyl-O—$R^g$,
 2) $C_1-C_{10}$ alkyl-NR$^f$R$^{f'}$,
said alkyl is optionally substituted with one or more substituents selected from $R^{10}$;
$R^4$ and $R^5$ are independently selected from:
 1) H, and
 2) $C_1-C_{10}$ alkyl,
said alkyl is optionally substituted with one or more substituents selected from $R^{10}$;
$R^{10}$ is independently selected from:
 1) $(C=O)_aO_bC_1-C_{10}$ alkyl,
 2) $(C=O)_aO_b$aryl,
 3) $C_2-C_{10}$ alkenyl,
 4) $C_2-C_{10}$ alkynyl,
 5) $(C=O)_aO_b$ heterocyclyl,
 6) $CO_2H$,
 7) halo,
 8) CN,
 9) OH,
 10) $O_bC_1-C_6$ perfluoroalkyl,
 11) $O_a(C=O)_bNR^{12}R^{13}$,
 12) $S(O)_mR^a$,
 13) $S(O)_2NR^{12}R^{13}$,
 14) oxo,
 15) CHO,
 16) $(N=O)R^{12}R^{13}$, or
 17) $(C=O)_aO_bC_3-C_8$ cycloalkyl,
said alkyl, aryl, alkenyl, alkynyl, heterocyclyl, and cycloalkyl optionally substituted with one, two or three substituents selected from $R^{11}$;
$R^{10'}$ is halogen;
$R^{11}$ is selected from:
 1) $(C=O)_rO_s(C_1-C_{10})$alkyl,
 2) $O_r(C_1-C_3)$perfluoroalkyl,
 3) oxo,
 4) OH,
 5) halo,
 6) CN,
 7) $(C_2-C_{10})$alkenyl,
 8) $(C_2-C_{10})$alkynyl,
 9) $(C=O)_rO_s(C_3-C_6)$cycloalkyl,
 10) $(C=O)_rO_s(C_0-C_6)$alkylene-aryl,
 11) $(C=O)_rO_s(C_0-C_6)$alkylene-heterocyclyl,
 12) $(C=O)_rO_s(C_0-C_6)$alkylene-N$(R^b)_2$,
 13) $C(O)R^a$,
 14) $(C_0-C_6)$alkylene-$CO_2R^a$,
 15) $C(O)H$,
 16) $(C_0-C_6)$alkylene-$CO_2H$, and
 17) $C(O)N(R^b)_2$,
 18) $S(O)_mR^a$, and
 19) $S(O)_2N(R^b)_2$;
said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;
$R^{12}$ and $R^{13}$ are independently selected from:
 1) H,
 2) $(C=O)O_bC_1-C_{10}$ alkyl,
 3) $(C=O)O_bC_3-C_8$ cycloalkyl,
 4) $(C=O)O_b$aryl,
 5) $(C=O)O_b$heterocyclyl,
 6) $C_1-C_{10}$ alkyl,
 7) aryl,
 8) $C_2-C_{10}$ alkenyl,
 9) $C_2-C_{10}$ alkynyl,
 10) heterocyclyl,
 11) $C_3-C_8$ cycloalkyl,
 12) $SO_2R^a$, and
 13) $(C=O)NR^b{}_2$,
said alkyl, cycloalkyl, aryl, heterocylyl, alkenyl, and alkynyl is optionally substituted with one, two or three substituents selected from $R^{11}$, or R$^{12}$ and R$^{13}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^a$ is independently selected from: (C$_1$-C$_6$)alkyl, (C$_3$-C$_6$) cycloalkyl, aryl, or heterocyclyl, optionally substituted with one, two or three substituents selected from R$^{11}$;

R$^b$ is independently selected from: H, (C$_1$-C$_6$)alkyl, aryl, heterocyclyl, (C$_3$-C$_6$)cycloalkyl, (C=O)OC$_1$-C$_6$ alkyl, (C=O)C$_1$-C$_6$ alkyl, (C=O)aryl, (C=O)heterocyclyl, (C=O)NR$^{c}$R$^{c'}$ or S(O)$_2$R$^a$, optionally substituted with one, two or three substituents selected from R$^{11}$;

R$^c$ and R$^{c'}$ are independently selected from: H, (C$_1$-C$_6$) alkyl, heterocyclyl and (C$_3$-C$_6$)cycloalkyl, optionally substituted with one, two or three substituents selected from R$^{11}$; or R$^c$ and R$^{c'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^d$ and R$^{d'}$ are independently selected from: (C$_1$-C$_6$)alkyl, (C$_1$-C$_6$)alkoxy and NR$^b{}_2$, or R$^d$ and R$^{d'}$ can be taken together with the phosphorous to which they are attached to form a monocyclic heterocycle with 3-7 members the ring and optionally containing, in addition to the phosphorous, one or two additional heteroatoms selected from NR$^e$, O and S, said monocyclic heterocycle optionally substituted with one, two or three substituents selected from R$^{11}$;

R$^e$ is selected from: H and (C$_1$-C$_6$)alkyl, optionally substituted with one, two or three substituents selected from R$^{11}$;

R$^f$ and R$^{f'}$ are independently selected from: H, (C$_1$-C$_6$) alkyl, —(C$_1$-C$_6$)alkyl-OH, —(C$_1$-C$_6$)alkyl-O—(C$_1$-C$_6$)alkyl and —(C$_1$-C$_6$)alkyl-N(R$^b$)$_2$, or R$^f$ and R$^{f'}$ can be taken together with the nitrogen to which they are attached to form a monocyclic or bicyclic heterocycle with 3-7 members in each ring and optionally containing, in addition to the nitrogen, one or two additional heteroatoms selected from N, O and S, said monocyclic or bicyclic heterocycle optionally substituted with one, two or three substituents selected from R$^{11}$;

R$^g$ is selected from: H, (C$_1$-C$_6$)alkyl, —(C$_1$-C$_6$)alkyl-OH, —(C$_1$-C$_6$)alkyl-O—(C$_1$-C$_6$)alkyl and —(C$_1$-C$_6$)alkyl-N(R$^b$)$_2$.

6. A compound selected from:

4-(2,5-Difluorophenyl)-2-(hydroxymethyl)-N,N-dimethyl-2-phenyl-2,5-dihydro-1H-pyrrole-1-carboxamide;

4-(2,5-Difluorophenyl)-2-(hydroxymethyl)-N-methyl-N-(1-methylpiperidin-4-yl)-2-phenyl-2,5-dihydro-1H-pyrrole-1-carboxamide;

4-(2,5-Difluorophenyl)-2-(methoxymethyl)-N,N-dimethyl-2-phenyl-2,5-dihydro-1H-pyrrole-1-carboxamide;

4-(2,5-Difluorophenyl)-2-[(2-hydroxyethoxy)methyl]-N,N-dimethyl-2-phenyl-2,5-dihydro-1H-pyrrole-1-carboxamide;

2-[(2-Aminoethoxy)methyl]-4-(2,5-difluorophenyl)-N,N-dimethyl-2-phenyl-2,5-dihydro-1H-pyrrole-1-carboxamide;

4-(2,5-Difluorophenyl)-2-({[2-(dimethylamino)ethyl]amino}methyl)-N,N-dimethyl-2-phenyl-2,5-dihydro-1H-pyrrole-1-carboxamide;

3-{4-(2,5-Difluorophenyl)-1-[(dimethylamino)carbonyl]-2-phenyl-2,5-dihydro-1H-pyrrol-2-yl}prop-2-en-1-amine;

2-(3-Hydroxypropyl)-4-(2,5-difluorophenyl)-N,N-dimethyl-2-phenyl-2,5-dihydro-1H-pyrrole-1-carboxamide;

2-(3-Aminopropyl)-4-(2,5-difluorophenyl)-N,N-dimethyl-2-phenyl-2,5-dihydro-1H-pyrrole-1-carboxamide;

4-(2,5-Difluorophenyl)-2-[3-(dimethylamino)propyl]-N,N-dimethyl-2-phenyl-2,5-dihydro-1H-pyrrole-1-carboxamide;

4-(2,5-difluorophenyl)-2-(1-hydroxyethyl)-N,N-dimethyl-2-phenyl-2,5-dihydro-1H-pyrrole-1-carboxamide;

[4-(2,5-difluorophenyl)-2-phenyl-1-(piperidin-1-ylcarbonyl)-2,5-dihydro-1H-pyrrol-2-yl]methanol;

2-({[tert-butyl(dimethyl)silyl]oxy}methyl)-4-(2,5-difluorophenyl)-N-methyl-2-phenyl-N-piperidin-4-yl-2,5-dihydro-1H-pyrrole-1-carboxamide;

4-(2,5-difluorophenyl)-N-[1-(N,N-dimethylglycyl)piperidin-4-yl]-2-(hydroxymethyl)-N-methyl-2-phenyl-2,5-dihydro-1H-pyrrole-1-carboxamide;

4-(2,5-difluorophenyl)-2-(hydroxymethyl)-N-methyl-N-[1-(morpholin-4-ylacetyl)piperidin-4-yl]-2-phenyl-2,5-dihydro-1H-pyrrole-1-carboxamide;

4-(2,5-difluorophenyl)-2-(hydroxymethyl)-N-methyl-2-phenyl-N-piperidin-3-yl-2,5-dihydro-1H-pyrrole-1-carboxamide;

N-[1-(2,2-difluoroethyl)piperidin-4-yl]-4-(2,5-difluorophenyl)-2-(hydroxymethyl)-N-methyl-2-phenyl-2,5-dihydro-1H-pyrrole-1-carboxamide;

4-(2,5-difluorophenyl)-N-[1-(2-hydroxyethyl)piperidin-4-yl]-2-(hydroxymethyl)-N-methyl-2-phenyl-2,5-dihydro-1H-pyrrole-1-carboxamide;

(2S)-4-(2,5-difluorophenyl)-N-[1-(2-fluoroethyl)piperidin-4-yl]-2-(hydroxymethyl)-N-methyl-2-phenyl-2,5-dihydro-1H-pyrrole-1-carboxamide;

4-(2,5-difluorophenyl)-2-(hydroxymethyl)-N-methyl-N-{1-[(methylsulfonyl)methyl]piperidin-4-yl}-2-phenyl-2,5-dihydro-1H-pyrrole-1-carboxamide;

4-(2,5-difluorophenyl)-N-{1-[2-fluoro-1-(fluoromethyl)ethyl]piperidin-4-yl}-2-(hydroxymethyl)-N-methyl-2-phenyl-2,5-dihydro-1H-pyrrole-1-carboxamide;

(2S)-N-(1-cyclopropylpiperidin-4-yl)-4-(2,5-difluorophenyl)-2-(hydroxymethyl)-N-methyl-2-phenyl-2,5-dihydro-1H-pyrrole-1-carboxamide;

benzyl {4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetate;

{4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetic acid;

methyl {4-[{[4-(2,5-difluorophenyl)-2-(hydroxymethyl)-2-phenyl-2,5-dihydro-1H-pyrrol-1-yl]carbonyl}(methyl)amino]piperidin-1-yl}acetate;

4-(2,5-difluorophenyl)-2-(methoxymethyl)-N-methyl-N-(1-methylpiperidin-4-yl)-2-phenyl-2,5-dihydro-1H-pyrrole-1-carboxamide;

4-(2,5-difluorophenyl)-2-(3-hydroxypropyl)-N,N-dimethyl-2-phenyl-2,5-dihydro-1H-pyrrole-1-carboxamide;

2-{3-[(2,2-difluoroethyl)amino]propyl}-4-(2,5-difluorophenyl)-N,N-dimethyl-2-phenyl-2,5-dihydro-1H-pyrrole-1-carboxamide;

2-{3-[(2,2-difluoroethyl)(methyl)amino]propyl}-4-(2,5-difluorophenyl)-N,N-dimethyl-2-phenyl-2,5-dihydro-1H-pyrrole-1-carboxamide;

2-(3-aminopropyl)-4-(5-chloro-2-fluorophenyl)-N,N-dimethyl-2-phenyl-2,5-dihydro-1H-pyrrole-1-carboxamide;

2-[3-(acetylamino)propyl]-4-(5-chloro-2-fluorophenyl)-N,N-dimethyl-2-phenyl-2,5-dihydro-1H-pyrrole-1-carboxamide;

4-(5-chloro-2-fluorophenyl)-N,N-dimethyl-2-{3-[(methylsulfonyl)amino]propyl}-2-phenyl-2,5-dihydro-1H-pyrrole-1-carboxamide;

methyl 3-{4-(5-chloro-2-fluorophenyl)-1-[(dimethylamino)carbonyl]-2-phenyl-2,5-dihydro-1H-pyrrol-2-yl}propylcarbamate;

2-{3-[(aminocarbonyl)amino]propyl}-4-(5-chloro-2-fluorophenyl)-N,N-dimethyl-2-phenyl-2,5-dihydro-1H-pyrrole-1-carboxamide;

3-{4-(2,5-difluorophenyl)-1-[(dimethylamino)carbonyl]-2-phenyl-2,5-dihydro-1H-pyrrol-2-yl}propanoic acid;

2-(3-anilino-3-oxopropyl)-4-(2,5-difluorophenyl)-N,N-dimethyl-2-phenyl-2,5-dihydro-1H-pyrrole-1-carboxamide;

4-(2,5-difluorophenyl)-2-(3-hydrazino-3-oxopropyl)-N,N-dimethyl-2-phenyl-2,5-dihydro-1H-pyrrole-1-carboxamide;

4-(2,5-difluorophenyl)-2-[3-(hydroxyamino)-3-oxopropyl]-N,N-dimethyl-2-phenyl-2,5-dihydro-1H-pyrrole-1-carboxamide;

2-(2,2-difluoro-3-hydroxypropyl)-4-(2,5-difluorophenyl)-N,N-dimethyl-2-phenyl-2,5-dihydro-1H-pyrrole-1-carboxamide;

2-(3-amino-2,2-difluoropropyl)-4-(2,5-difluorophenyl)-N,N-dimethyl-2-phenyl-2,5-dihydro-1H-pyrrole-1-carboxamide;

4-(2,5-difluorophenyl)-2-[3-(dimethylamino)propyl]-N-methyl-2-phenyl-N-tetrahydro-2H-pyran-4-yl-2,5-dihydro-1H-pyrrole-1-carboxamide;

1-{4-(2,5-difluorophenyl)-2-[3-(dimethylamino)propyl]-2-phenyl-2,5-dihydro-1H-pyrrol-1-yl}-2-methyl-1-oxopropan-2-ol;

3-[(2S)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine; and (2S)-2-(3-amino-4,4-difluorobutyl)-4-(2,5-difluorophenyl)-N,N-dimethyl-2-phenyl-2,5-dihydro-1H-pyrrole-1-carboxamide;

or a pharmaceutically acceptable salt or stereoisomer thereof.

7. The compound according to claim 6 which is selected from:

4-(2,5-Difluorophenyl)-2-(hydroxymethyl)-N-methyl-N-(1-methylpiperidin-4-yl)-2-phenyl-2,5-dihydro-1H-pyrrole-1-carboxamide;

2-[(2-Aminoethoxy)methyl]-4-(2,5-difluorophenyl)-N,N-dimethyl-2-phenyl-2,5-dihydro-1H-pyrrole-1-carboxamide;

2-(3-Aminopropyl)-4-(2,5-difluorophenyl)-N,N-dimethyl-2-phenyl-2,5-dihydro-1H-pyrrole-1-carboxamide;

4-(2,5-Difluorophenyl)-2-[3-(dimethylamino)propyl]-N,N-dimethyl-2-phenyl-2,5-dihydro-1H-pyrrole-1-carboxamide;

or a pharmaceutically acceptable salt or stereoisomer thereof.

8. The compound according to claim 1 selected from:

2-[(2-Aminoethoxy)methyl]-4-(2,5-difluorophenyl)-N,N-dimethyl-2-phenyl-2,5-dihydro-1H-pyrrole-1-carboxamide hydrochloride salt;

4-(2,5-Difluorophenyl)-2-({[2-(dimethylamino)ethyl]amino}methyl)-N,N-dimethyl-2-phenyl-2,5-dihydro-1H-pyrrole-1-carboxamide bis TFA salt;

2-(3-Aminopropyl)-4-(2,5-difluorophenyl)-N,N-dimethyl-2-phenyl-2,5-dihydro-1H-pyrrole-1-carboxamide hydrochloride salt;

4-(2,5-Difluorophenyl)-2-[3-(dimethylamino)propyl]-N,N-dimethyl-2-phenyl-2,5-dihydro-1H-pyrrole-1-carboxamide TFA salt;

4-(2,5-difluorophenyl)-N-[1-(glycyl)piperidin-4-yl]-2-(hydroxymethyl)-N-methyl-2-phenyl-2,5-dihydro-1H-pyrrole-1-carboxamide TFA salt;

3-[(2S)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine bis-TFA salt;

3-[(2R)-1-[(2S)-2-amino-2-cyclopropylethanoyl]-4-(2,5-difluorophenyl)-2-phenyl-2,5-dihydro-1H-pyrrol-2-yl]-N,N-dimethylpropan-1-amine bis-TFA salt;

4-(2,5-difluorophenyl)-2-[3-(dimethylamino)propyl]-N-methyl-N-(1-methylpiperidin-4-yl)-2-phenyl-2,5-dihydro-1H-pyrrole-1-carboxamide bis-TFA salt;

4-(2,5-difluorophenyl)-2-[3-(ethylamino)propyl]-N,N-dimethyl-2-phenyl-2,5-dihydro-1H-pyrrole-1-carboxamide TFA salt;

4-(2,5-difluorophenyl)-N,N-dimethyl-2-phenyl-2-{3-[(pyridin-4-ylmethyl)amino]propyl}-2,5-dihydro-1H-pyrrole-1-carboxamide bis-TFA salt; and 4-(2,5-difluorophenyl)-N,N-dimethyl-2-(3-{[(4-methyl-1H-imidazol-2-yl)methyl]amino}propyl)-2-phenyl-2,5-dihydro-1H-pyrrole-1-carboxamide bis-TFA salt.

9. A pharmaceutical composition that is comprised of a compound in accordance with claim 1 and a pharmaceutically acceptable carrier.

* * * * *